(12) United States Patent
Gopalakrishnakone et al.

(10) Patent No.: US 7,094,575 B2
(45) Date of Patent: Aug. 22, 2006

(54) THERAPEUTIC AND PROPHYLACTIC AGENTS AND METHODS OF USING SAME

(75) Inventors: Ponnampalam Gopalakrishnakone, Singapore (SG); Maung-Maung Thwin, Singapore (SG); Kandiah Jeyaseelan, Melbourne (AU); Arunmozhiarasi Armugam, Singapore (SG)

(73) Assignee: National University of Singapore, Singapore (SG)

( * ) Notice: Subject to any disclaimer, the term of this patent is extended or adjusted under 35 U.S.C. 154(b) by 390 days.

(21) Appl. No.: 10/163,499

(22) Filed: Jun. 7, 2002

(65) Prior Publication Data

US 2003/0027764 A1 Feb. 6, 2003

Related U.S. Application Data

(63) Continuation of application No. PCT/SG00/00201, filed on Dec. 7, 2000.

(30) Foreign Application Priority Data

Dec. 8, 1999 (SG) ................................. 9906237-4

(51) Int. Cl.
C12N 15/09 (2006.01)
(52) U.S. Cl. .................. 435/69.2; 435/325; 435/320.1; 536/23.5
(58) Field of Classification Search ............... 435/69.2, 435/325, 320.1; 536/23.5
See application file for complete search history.

(56) References Cited

U.S. PATENT DOCUMENTS 5,663,059 A * 9/1997 Hawkins et al. ........... 435/69.2

FOREIGN PATENT DOCUMENTS

EP 0501779 A1 9/1992

WO WO 97/44454 11/1997

OTHER PUBLICATIONS

Thwin et al., Biochemistry, 39, 9604-9611 (2000).
Thwin et al., Toxicon, 34, 314 (1996). XP-001024650.
Thwin et al., Toxicon, 36, 1471-1482 (1998).
Thwin et al., Toxicon, 37, 1465 (1999). XP-001024668.
Thwin et al., Toxicon, 39, 152 (2001). XP-001024667.

* cited by examiner

*Primary Examiner*—Bruce R. Campell
*Assistant Examiner*—Roy Teller
(74) *Attorney, Agent, or Firm*—Birch, Stewart, Kolasch & Birch, LLP

(57) ABSTRACT

A phospholipase $A_2$ inhibitor protein designated "Phospholipase Inhibitor from Python" (PIP)—formerly designated "Python Antitoxic Factor" (PAF)—is given by SEQ ID NO:2. The partial amino acid sequence for PIP was initially determined from the native protein purified from the blood serum of a non-venomous snake, *Python reticulatus*. The complete PIP polynucleotide sequence was obtained from a cDNA clone encoding PIP, given by SEQ ID NO:1, along with the full amino acid sequence deduced from it. Also disclosed is a recombinant protein PIP, which shows strong lethal toxin neutralizing activity similar to the native PIP, and has potent anti-inflammatory activity. Both the native and the functionally equivalent recombinant PIP are useful for the prevention or treatment of conditions such as snakebites, insect stings, and inflammatory diseases. Also, phospholipase $A_2$ ($PLA_2$) inhibitory polypeptides designated P-0029, P-0009, and P-0006, the sequences of which are given as SEQ ID NO:10, SEQ ID NO:11, and SEQ ID NO:12, respectively, are disclosed. Those polypeptides, and their synthetic chemical analogues and polypeptide variants that inhibit $PLA_2$ activity and alleviate inflammation, may also be used in the diagnosis, study, prevention, and treatment of $PLA_2$-related human inflammatory diseases.

14 Claims, 10 Drawing Sheets

Figure 1:
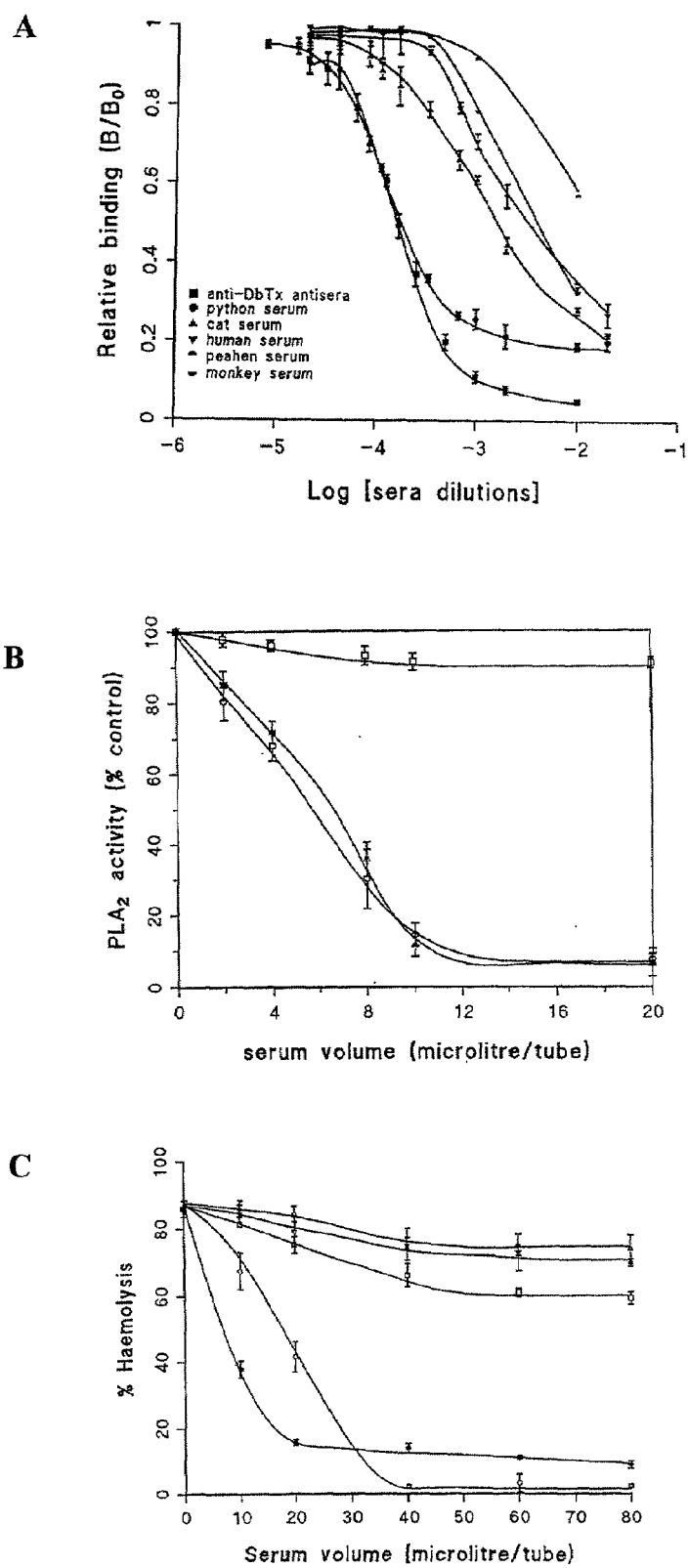

(3 of 10 Drawing Sheet(s) Filed in Color)

```
          1         10        20        30        40        50        60
DKCEICHGEGDDCDGYQEE-CPSPEDRCGKILIDIALAEVSFRATHKNCFSSSICKLGRVD  (1)
RSCDYCHNIGKDCDGYEHE-CSSPEDVCGKVFLEISSASLSVRTVHKNCFSSSVCKLGHFD  (2)
RSCDFCHNIGKDCDGYEEE-CSSPEDVCGKVLLEISSASLSVRTVHKNCFSSSICKLGQFD  (3)
RSCDFCHNIGADCEGFQHE-CSPEDECGKVFLEISSASLSVRTVHKNCFSSSVCKLRHFD   (4)
RSCEICHNVGNDCGYDYVEECHSPEDQCGKVLLEISSAPLSIRSSHRNCFSSSLCKLEHFD  (5)
RSCEICHNFGKDCEGGETEECASPEDQCGTVLMEVSTAPISFRSIHRNCFSSSLCKLERFD  (6)
HSCELCHNLGRDCETEEAEECASPEDQCGTVLMEVSSAPISFRSIHRNCFSSSLCKLERFD  (7)
HSCEICRNFGKDCESEEAEECASPEDQCGTVLLEISSAPISFRSIHRNCFSSSLCKLEHFD  (8)

70        80        90        100       110       120
IHVWDGVYIRGRTNCCDNDQCEDQPLPGLPLSLQNGLYCPGAFGIFTEDSTEHEVKCRGTE  (1)
INIGHHSYIRGRINCCEKEPCEDQPFPGLPLSQPNGYYCPGALGLFTEDSTEYEAICKGTE  (2)
VNIGHHSYIRGRINCCEKELCEDQPFPGLPLSKPNGYYCPGAIGLFTKDSTEYEAICKGTE  (3)
VNIGHDSYIRGRINCCEKEPCEDQSFPGLPLSQPNGYYCPGSLGLFTKDSTEFEAICKGTE  (4)
VNTGQETYLRGRIHCCDEKKCEGREFPGLPLSHPNGYVCPGVLGLFSEDSSESEAACKGDE  (5)
INIGHDSFLRGRIHCCDEARCEAQQFPGLPLSFPNGYHCPGILGLFSVDSSEHEAICRGTE  (6)
INIGHDSYLRGRIHCCDEARCEAQQFPGLPLSFPNGYHCPGILGVFSVDSSEHEAICRGTE  (7)
INIGHDSYVRGRIHCCDEERCEAQQFPGLPLSFPNGYHCPGILGAFSVDSSEHEAICRGTE  (8)

130       140       150       160       170       180
EMCLDLVGYRQESYAGNITYNIKGCVSSCPLVTLSERGHEGRKNDLKKVECREALKPASSD  (1)
TKCINIVGHRHENYPGDISYNLKGCVSSCPLLSLSNSTHEENRNYLEKVECKDAFKIASH-  (2)
TKCINIVGHRYEQFPGDISYNLKGCVSSCPLLSLSNATHEQNRNYLEKVECKDAIRLASL- (3)
TKCINIVGHRYEHYPGDIAYNLKGCISSCPLLSLSNATHEENRNYLEKVECKDALQFEKQ- (4)
TKCINIVGYRKERFPGDIAYNIKGCVSSCPELRLSNRTHEERRNDLIKVECRDAVKITPSE (5)
TKCINLAGFRRERFPGDIAYNIKGCTSSCPELRLSNRTHEEHRNDLIKVECTEASKNTPSE (6)
TKCINLAGFRKERFPGDIGYNIKGCTSSCPELRLSNRTHEEDRNDLIKVECTDASKITPSE (7)
TKCINLAGFRKERYPVDIAYNIKGCTSSCPELKLSNRTHEERRNDLITLECTDASKIAPSE (8)
```

Fig. 6

| | Amino acid sequence | Inhibitor Name | Sequence Identity |
|---|---|---|---|
| | 85                    112 | | |
| (1) | PLPGLPLSLQNGLYCPGAFGIFTEDSTE | Python reticulatus PIP | 100 |
| (2) | PFPGLPLSQPNGYYCPGALGLFTEDSTE | Agkistrodon b. siniticus PLIγ-A | 79 |
| (3) | PFPGLPLSKPNGYYCPGAIGLFTKDSTE | Crotalus d. terrificus CNF | 75 |
| (4) | SFPGLPLSQPNGYYCPGSLGLFTKDSTE | Protobothrops flavoviridis PLI-I | 68 |
| (5) | PFPGLPLSHPNGYVCPGVLGLFSEDSSE | Elaphe quadrivirgata PLIγ-A | 64 |
| (6) | QFPGLPLSFPNGYHCPGILGLFSVDSSE | Notechis ater α-subunit NAI-3A | 57 |
| (7) | QFPGLPLSFPNGYHCPGILGVFSVDSSE | Notechis scutellatus α-chain iii | 57 |
| (8) | QFPGLPLSFPNGYHCPGILGAFSVDSSE | Oxyuranus scutellatus α-subunit OSI-1A | 57 |
| (9) | QFPGLPLSLPNGYYCPGILGLFTVDSSE | Laticauda semifasciaata PLIγ-A | 68 |

Fig. 7

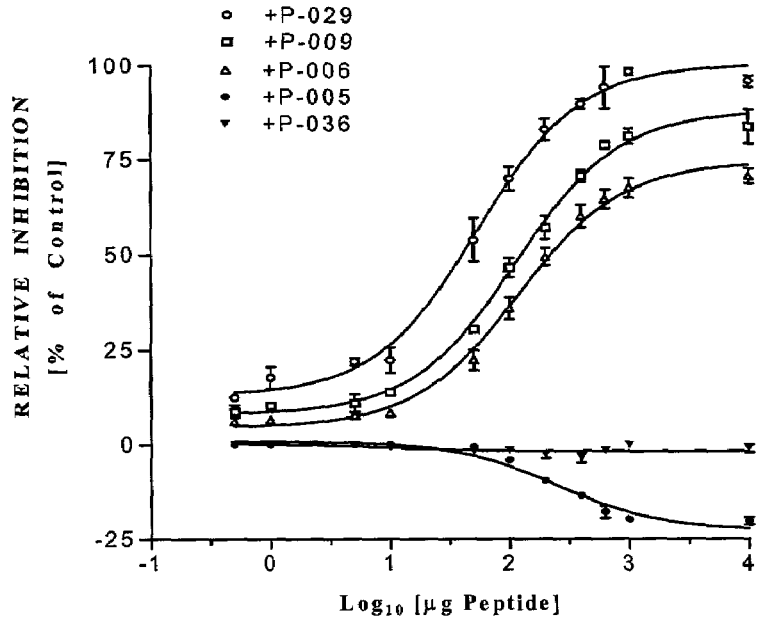
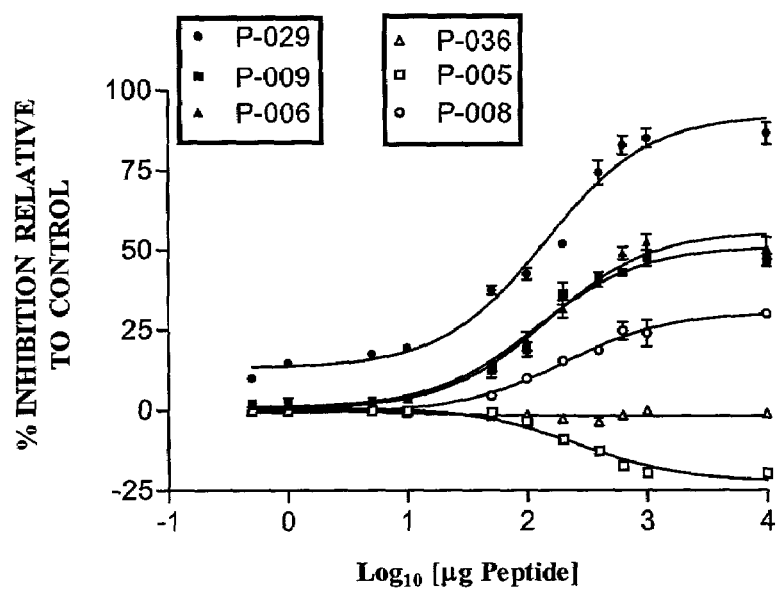
Fig. 8

ADHESION GRADE 4
ADHESION GRADE 3
ADHESION GRADE 2
ADHESION GRADE 1
Fig. 9

SEQUENCE LISTING

```
<160> NUMBER OF SEQ ID NOS: 33

<210> SEQ ID NO 1
<211> LENGTH: 816
<212> TYPE: DNA
<213> ORGANISM: Python reticulatus
<220> FEATURE:
<221> NAME/KEY: 5'UTR
<222> LOCATION: (1)..(53)
<220> FEATURE:
<221> NAME/KEY: CDS
<222> LOCATION: (54)..(656)
<220> FEATURE:
<221> NAME/KEY: 3'UTR
<222> LOCATION: (657)..(816)
<220> FEATURE:
<221> NAME/KEY: sig_peptide
<222> LOCATION: (54)..(110)
<220> FEATURE:
```

```
<221> NAME/KEY: mat_peptide
<222> LOCATION: (111)..(656)

<400> SEQUENCE: 1
attcaacata tccaatccag ctctgatctt taccagagaa gacatcttga gcc atg          56
                                                             Met aaa tcc cta cag acc att tgc ctt ctt ttc att ttt ata gct aga gga        104
Lys Ser Leu Gln Thr Ile Cys Leu Leu Phe Ile Phe Ile Ala Arg Gly
        -15                 -10                 -5 acc tct gac aaa tgt gaa att tgt cat ggc ttt gga gat gac tgt gat        152
Thr Ser Asp Lys Cys Glu Ile Cys His Gly Phe Gly Asp Asp Cys Asp
    -1  1               5                  10 ggt tat cag gag gaa tgt ccc tct cca gaa gac cga tgt ggc aag att        200
Gly Tyr Gln Glu Glu Cys Pro Ser Pro Glu Asp Arg Cys Gly Lys Ile
 15              20                  25                  30 ctg ata gac atc gca tta gca cca gtt tca ttc aga gcc acg cat aag        248
Leu Ile Asp Ile Ala Leu Ala Pro Val Ser Phe Arg Ala Thr His Lys
             35                  40                  45 aat tgt ttc tca tcc agc atc tgt aaa ctt ggc cgt gtt gac ata cat        296
Asn Cys Phe Ser Ser Ser Ile Cys Lys Leu Gly Arg Val Asp Ile His
         50                  55                  60 gtt tgg gat gga gtg tat ata aga gga aga aca aat tgc tgt gat aat        344
Val Trp Asp Gly Val Tyr Ile Arg Gly Arg Thr Asn Cys Cys Asp Asn
     65                  70                  75 gat cag tgt gaa gac caa cca ctt cct gga ttg ccc ctc tcc ctc cag        392
Asp Gln Cys Glu Asp Gln Pro Leu Pro Gly Leu Pro Leu Ser Leu Gln
 80                  85                  90 aat ggg ctc tat tgt cct ggt gct ttt ggt att ttt acc gag gac agc        440
Asn Gly Leu Tyr Cys Pro Gly Ala Phe Gly Ile Phe Thr Glu Asp Ser
 95                 100                 105                 110 act gaa cat gaa gtt aaa tgc aga gga act gaa act atg tgc ctt gat        488
Thr Glu His Glu Val Lys Cys Arg Gly Thr Glu Thr Met Cys Leu Asp
                 115                 120                 125 ctt gtg gga tac aga caa gaa agt tat gct gga aac atc act tat aat        536
Leu Val Gly Tyr Arg Gln Glu Ser Tyr Ala Gly Asn Ile Thr Tyr Asn
             130                 135                 140 atc aaa ggc tgt gtt tct tcc tgt ccc ttg gta act ttg agt gaa aga        584
Ile Lys Gly Cys Val Ser Ser Cys Pro Leu Val Thr Leu Ser Glu Arg
         145                 150                 155 ggt cat gaa gga cgc aaa aat gat ctg aag aag gtt gaa tgt agg gaa        632
Gly His Glu Gly Arg Lys Asn Asp Leu Lys Lys Val Glu Cys Arg Glu
     160                 165                 170 gcc ttg aaa cct gca tcc tct gat taatactgga atcattctgg aatctgaatg       686
Ala Leu Lys Pro Ala Ser Ser Asp
 175                 180 tcttcaccag gtagaacctg cctcatcaga atgactctga atggaaactt acatttttaa      746
gttgtggctc ttcctgctga ttaattttta aaaattaaaa aaaaagcaaa taaagaagt       806 caaagtgaat                                                              816

<210> SEQ ID NO 2
<211> LENGTH: 201
<212> TYPE: PRT
<213> ORGANISM: Python reticulatus

<400> SEQUENCE: 2

Met Lys Ser Leu Gln Thr Ile Cys Leu Leu Phe Ile Phe Ile Ala Arg
                 -15                 -10                 -5

Gly Thr Ser Asp Lys Cys Glu Ile Cys His Gly Phe Gly Asp Asp Cys
        -1  1               5                  10
```

-continued

```
Asp Gly Tyr Gln Glu Glu Cys Pro Ser Pro Glu Asp Arg Cys Gly Lys
    15                  20                  25

Ile Leu Ile Asp Ile Ala Leu Ala Pro Val Ser Phe Arg Ala Thr His
30                  35                  40                  45

Lys Asn Cys Phe Ser Ser Ile Cys Lys Leu Gly Arg Val Asp Ile
                50                  55                  60

His Val Trp Asp Gly Val Tyr Ile Arg Gly Arg Thr Asn Cys Cys Asp
            65                  70                  75

Asn Asp Gln Cys Glu Asp Gln Pro Leu Pro Gly Leu Pro Leu Ser Leu
        80                  85                  90

Gln Asn Gly Leu Tyr Cys Pro Gly Ala Phe Gly Ile Phe Thr Glu Asp
    95                  100                 105

Ser Thr Glu His Glu Val Lys Cys Arg Gly Thr Glu Thr Met Cys Leu
110                 115                 120                 125

Asp Leu Val Gly Tyr Arg Gln Glu Ser Tyr Ala Gly Asn Ile Thr Tyr
                130                 135                 140

Asn Ile Lys Gly Cys Val Ser Ser Cys Pro Leu Val Thr Leu Ser Glu
            145                 150                 155

Arg Gly His Glu Gly Arg Lys Asn Asp Leu Lys Lys Val Glu Cys Arg
        160                 165                 170

Glu Ala Leu Lys Pro Ala Ser Ser Asp
    175                 180

<210> SEQ ID NO 3
<211> LENGTH: 603
<212> TYPE: DNA
<213> ORGANISM: Python reticulatus
<220> FEATURE:
<221> NAME/KEY: CDS
<222> LOCATION: (1)..(603)

<400> SEQUENCE: 3 atg aaa tcc cta cag acc att tgc ctt ctt ttc att ttt ata gct aga        48
Met Lys Ser Leu Gln Thr Ile Cys Leu Leu Phe Ile Phe Ile Ala Arg
1               5                   10                  15 gga acc tct gac aaa tgt gaa att tgt cat ggc ttt gga gat gac tgt        96
Gly Thr Ser Asp Lys Cys Glu Ile Cys His Gly Phe Gly Asp Asp Cys
            20                  25                  30 gat ggt tat cag gag gaa tgt ccc tct cca gaa gac cga tgt ggc aag       144
Asp Gly Tyr Gln Glu Glu Cys Pro Ser Pro Glu Asp Arg Cys Gly Lys
        35                  40                  45 att ctg ata gac atc gca tta gca cca gtt tca ttc aga gcc acg cat       192
Ile Leu Ile Asp Ile Ala Leu Ala Pro Val Ser Phe Arg Ala Thr His
    50                  55                  60 aag aat tgt ttc tca tcc agc atc tgt aaa ctt ggc cgt gtt gac ata       240
Lys Asn Cys Phe Ser Ser Ser Ile Cys Lys Leu Gly Arg Val Asp Ile
65                  70                  75                  80 cat gtt tgg gat gga gtg tat ata aga gga aga aca aat tgc tgt gat       288
His Val Trp Asp Gly Val Tyr Ile Arg Gly Arg Thr Asn Cys Cys Asp
                85                  90                  95 aat gat cag tgt gaa gac caa cca ctt cct gga ttg ccc ctc tcc ctc       336
Asn Asp Gln Cys Glu Asp Gln Pro Leu Pro Gly Leu Pro Leu Ser Leu
            100                 105                 110 cag aat ggg ctc tat tgt cct ggt gct ttt ggt att ttt acc gag gac       384
Gln Asn Gly Leu Tyr Cys Pro Gly Ala Phe Gly Ile Phe Thr Glu Asp
        115                 120                 125 agc act gaa cat gaa gtt aaa tgc aga gga act gaa act atg tgc ctt       432
Ser Thr Glu His Glu Val Lys Cys Arg Gly Thr Glu Thr Met Cys Leu
```

|  |  |  |  |  |  |  |  |  |  |  |  |  |  |  |  |
|---|---|---|---|---|---|---|---|---|---|---|---|---|---|---|---|
|  | 130 |  |  |  | 135 |  |  |  | 140 |  |  |  |  |  |  |
| gat | ctt | gtg | gga | tac | aga | caa | gaa | agt | tat | gct | gga | aac | atc | act | tat | 480 |
| Asp | Leu | Val | Gly | Tyr | Arg | Gln | Glu | Ser | Tyr | Ala | Gly | Asn | Ile | Thr | Tyr |
| 145 |  |  |  |  | 150 |  |  |  | 155 |  |  |  |  | 160 |  |
| aat | atc | aaa | ggc | tgt | gtt | tct | tcc | tgt | ccc | ttg | gta | act | ttg | agt | gaa | 528 |
| Asn | Ile | Lys | Gly | Cys | Val | Ser | Ser | Cys | Pro | Leu | Val | Thr | Leu | Ser | Glu |
|  |  |  |  | 165 |  |  |  |  | 170 |  |  |  |  | 175 |  |
| aga | ggt | cat | gaa | gga | cgc | aaa | aat | gat | ctg | aag | aag | gtt | gaa | tgt | agg | 576 |
| Arg | Gly | His | Glu | Gly | Arg | Lys | Asn | Asp | Leu | Lys | Lys | Val | Glu | Cys | Arg |
|  |  |  | 180 |  |  |  |  | 185 |  |  |  |  | 190 |  |  |
| gaa | gcc | ttg | aaa | cct | gca | tcc | tct | gat |  |  |  |  |  |  |  | 603 |
| Glu | Ala | Leu | Lys | Pro | Ala | Ser | Ser | Asp |  |  |  |  |  |  |  |
|  |  | 195 |  |  |  |  | 200 |  |  |  |  |  |  |  |  |

<210> SEQ ID NO 4
<211> LENGTH: 201
<212> TYPE: PRT
<213> ORGANISM: Python reticulatus

<400> SEQUENCE: 4

Met Lys Ser Leu Gln Thr Ile Cys Leu Leu Phe Ile Phe Ile Ala Arg
1               5                   10                  15

Gly Thr Ser Asp Lys Cys Glu Ile Cys His Gly Phe Gly Asp Asp Cys
            20                  25                  30

Asp Gly Tyr Gln Glu Glu Cys Pro Ser Pro Glu Asp Arg Cys Gly Lys
        35                  40                  45

Ile Leu Ile Asp Ile Ala Leu Ala Pro Val Ser Phe Arg Ala Thr His
    50                  55                  60

Lys Asn Cys Phe Ser Ser Ile Cys Lys Leu Gly Arg Val Asp Ile
65                  70                  75                  80

His Val Trp Asp Gly Val Tyr Ile Arg Gly Arg Thr Asn Cys Cys Asp
                85                  90                  95

Asn Asp Gln Cys Glu Asp Gln Pro Leu Pro Gly Leu Pro Leu Ser Leu
            100                 105                 110

Gln Asn Gly Leu Tyr Cys Pro Gly Ala Phe Gly Ile Phe Thr Glu Asp
        115                 120                 125

Ser Thr Glu His Glu Val Lys Cys Arg Gly Thr Glu Thr Met Cys Leu
    130                 135                 140

Asp Leu Val Gly Tyr Arg Gln Glu Ser Tyr Ala Gly Asn Ile Thr Tyr
145                 150                 155                 160

Asn Ile Lys Gly Cys Val Ser Ser Cys Pro Leu Val Thr Leu Ser Glu
                165                 170                 175

Arg Gly His Glu Gly Arg Lys Asn Asp Leu Lys Lys Val Glu Cys Arg
            180                 185                 190

Glu Ala Leu Lys Pro Ala Ser Ser Asp
        195                 200

<210> SEQ ID NO 5
<211> LENGTH: 546
<212> TYPE: DNA
<213> ORGANISM: Python reticulatus
<220> FEATURE:
<221> NAME/KEY: CDS
<222> LOCATION: (1)..(546)
<220> FEATURE:
<221> NAME/KEY: mat_peptide
<222> LOCATION: (1)..(546)

<400> SEQUENCE: 5

| | | |
|---|---|---|
| gac aaa tgt gaa att tgt cat ggc ttt gga gat gac tgt gat ggt tat<br>Asp Lys Cys Glu Ile Cys His Gly Phe Gly Asp Asp Cys Asp Gly Tyr<br>1                    5                         10                       15 | 48 |
| cag gag gaa tgt ccc tct cca gaa gac cga tgt ggc aag att ctg ata<br>Gln Glu Glu Cys Pro Ser Pro Glu Asp Arg Cys Gly Lys Ile Leu Ile<br>                  20                        25                       30 | 96 |
| gac atc gca tta gca cca gtt tca ttc aga gcc acg cat aag aat tgt<br>Asp Ile Ala Leu Ala Pro Val Ser Phe Arg Ala Thr His Lys Asn Cys<br>              35                       40                       45 | 144 |
| ttc tca tcc agc atc tgt aaa ctt ggc cgt gtt gac ata cat gtt tgg<br>Phe Ser Ser Ser Ile Cys Lys Leu Gly Arg Val Asp Ile His Val Trp<br>    50                       55                       60 | 192 |
| gat gga gtg tat ata aga gga aga aca aat tgc tgt gat aat gat cag<br>Asp Gly Val Tyr Ile Arg Gly Arg Thr Asn Cys Cys Asp Asn Asp Gln<br>65                    70                       75                       80 | 240 |
| tgt gaa gac caa cca ctt cct gga ttg ccc ctc tcc ctc cag aat ggg<br>Cys Glu Asp Gln Pro Leu Pro Gly Leu Pro Leu Ser Leu Gln Asn Gly<br>                      85                       90                       95 | 288 |
| ctc tat tgt cct ggt gct ttt ggt att ttt acc gag gac agc act gaa<br>Leu Tyr Cys Pro Gly Ala Phe Gly Ile Phe Thr Glu Asp Ser Thr Glu<br>                  100                     105                   110 | 336 |
| cat gaa gtt aaa tgc aga gga act gaa act atg tgc ctt gat ctt gtg<br>His Glu Val Lys Cys Arg Gly Thr Glu Thr Met Cys Leu Asp Leu Val<br>            115                       120                   125 | 384 |
| gga tac aga caa gaa agt tat gct gga aac atc act tat aat atc aaa<br>Gly Tyr Arg Gln Glu Ser Tyr Ala Gly Asn Ile Thr Tyr Asn Ile Lys<br>130                   135                     140 | 432 |
| ggc tgt gtt tct tcc tgt ccc ttg gta act ttg agt gaa aga ggt cat<br>Gly Cys Val Ser Ser Cys Pro Leu Val Thr Leu Ser Glu Arg Gly His<br>145                    150                     155                   160 | 480 |
| gaa gga cgc aaa aat gat ctg aag aag gtt gaa tgt agg gaa gcc ttg<br>Glu Gly Arg Lys Asn Asp Leu Lys Lys Val Glu Cys Arg Glu Ala Leu<br>                  165                     170                   175 | 528 |
| aaa cct gca tcc tct gat<br>Lys Pro Ala Ser Ser Asp<br>                  180 | 546 |

<210> SEQ ID NO 6
<211> LENGTH: 182
<212> TYPE: PRT
<213> ORGANISM: Python reticulatus

<400> SEQUENCE: 6

Asp Lys Cys Glu Ile Cys His Gly Phe Gly Asp Asp Cys Asp Gly Tyr
1               5                   10                  15

Gln Glu Glu Cys Pro Ser Pro Glu Asp Arg Cys Gly Lys Ile Leu Ile
            20                  25                  30

Asp Ile Ala Leu Ala Pro Val Ser Phe Arg Ala Thr His Lys Asn Cys
        35                  40                  45

Phe Ser Ser Ser Ile Cys Lys Leu Gly Arg Val Asp Ile His Val Trp
    50                  55                  60

Asp Gly Val Tyr Ile Arg Gly Arg Thr Asn Cys Cys Asp Asn Asp Gln
65                  70                  75                  80

Cys Glu Asp Gln Pro Leu Pro Gly Leu Pro Leu Ser Leu Gln Asn Gly
                85                  90                  95

Leu Tyr Cys Pro Gly Ala Phe Gly Ile Phe Thr Glu Asp Ser Thr Glu
            100                 105                 110

His Glu Val Lys Cys Arg Gly Thr Glu Thr Met Cys Leu Asp Leu Val
        115                 120                 125

-continued

Gly Tyr Arg Gln Glu Ser Tyr Ala Gly Asn Ile Thr Tyr Asn Ile Lys
        130                 135                 140

Gly Cys Val Ser Ser Cys Pro Leu Val Thr Leu Ser Glu Arg Gly His
145                 150                 155                 160

Glu Gly Arg Lys Asn Asp Leu Lys Lys Val Glu Cys Arg Glu Ala Leu
                165                 170                 175

Lys Pro Ala Ser Ser Asp
            180

<210> SEQ ID NO 7
<211> LENGTH: 57
<212> TYPE: DNA
<213> ORGANISM: Python reticulatus
<220> FEATURE:
<221> NAME/KEY: CDS
<222> LOCATION: (1)..(57)
<220> FEATURE:
<221> NAME/KEY: sig_peptide
<222> LOCATION: (1)..(57)

<400> SEQUENCE: 7 atg aaa tcc cta cag acc att tgc ctt ctt ttc att ttt ata gct aga    48
Met Lys Ser Leu Gln Thr Ile Cys Leu Leu Phe Ile Phe Ile Ala Arg
1               5                   10                  15 gga acc tct                                                        57
Gly Thr Ser <210> SEQ ID NO 8
<211> LENGTH: 19
<212> TYPE: PRT
<213> ORGANISM: Python reticulatus

<400> SEQUENCE: 8

Met Lys Ser Leu Gln Thr Ile Cys Leu Leu Phe Ile Phe Ile Ala Arg
1               5                   10                  15

Gly Thr Ser

<210> SEQ ID NO 9
<211> LENGTH: 32
<212> TYPE: PRT
<213> ORGANISM: Python reticulatus

<400> SEQUENCE: 9

Asp Lys Cys Glu Ile Cys His Gly Phe Gly Asp Asp Cys Cys Gly Tyr
1               5                   10                  15

Gln Glu Glu Cys Pro Ser Pro Glu Asp Arg Cys Gly Lys Ile Leu Ile
            20                  25                  30

<210> SEQ ID NO 10
<211> LENGTH: 10
<212> TYPE: PRT
<213> ORGANISM: Artificial Sequence
<220> FEATURE:
<223> OTHER INFORMATION: Decapeptide designated P-0029: Synthetic peptide
      derived from the proline-rich domain; Original source organism:
      Python reticulatus; Custom-synthesized at Biotechnology Processing
      Centre (BTC), NUS

<400> SEQUENCE: 10

Pro Gly Leu Pro Leu Ser Leu Gln Asn Gly
1               5                   10

<210> SEQ ID NO 11

-continued

```
<211> LENGTH: 10
<212> TYPE: PRT
<213> ORGANISM: Artificial Sequence
<220> FEATURE:
<223> OTHER INFORMATION: Decapeptide designated P-0009:
      Synthetic peptide derived from the proline-rich domain; Original
      source organism: Python reticulatus; Custom-synthesized at
      Biotechnology Processing Centre (BTC), NUS

<400> SEQUENCE: 11

Pro Leu Pro Gly Leu Pro Leu Ser Lys Pro
1               5                   10

<210> SEQ ID NO 12
<211> LENGTH: 9
<212> TYPE: PRT
<213> ORGANISM: Artificial Sequence
<220> FEATURE:
<223> OTHER INFORMATION: Nonapeptide designated P-0006:
      Synthetic peptide derived from the proline-rich domain; Original
      source organism: Python reticulatus; Custom-synthesized at
      Biotechnology Processing Centre (BTC), NUS

<400> SEQUENCE: 12

Leu Ser Leu Gln Asn Gly Leu Tyr Lys
1               5

<210> SEQ ID NO 13
<211> LENGTH: 182
<212> TYPE: PRT
<213> ORGANISM: Python reticulatus

<400> SEQUENCE: 13

Asp Lys Cys Glu Ile Cys His Gly Phe Gly Asp Asp Cys Asp Gly Tyr
1               5                   10                  15

Gln Glu Glu Cys Pro Ser Pro Glu Asp Arg Cys Gly Lys Ile Leu Ile
                20                  25                  30

Asp Ile Ala Leu Ala Pro Val Ser Phe Arg Ala Thr His Lys Asn Cys
            35                  40                  45

Phe Ser Ser Ile Cys Lys Leu Gly Arg Val Asp Ile His Val Trp
    50                  55                  60

Asp Gly Val Tyr Ile Arg Gly Arg Thr Asn Cys Cys Asp Asn Asp Gln
65                  70                  75                  80

Cys Glu Asp Gln Pro Leu Pro Gly Leu Pro Leu Ser Leu Gln Asn Gly
                85                  90                  95

Leu Tyr Cys Pro Gly Ala Phe Gly Ile Phe Thr Glu Asp Ser Thr Glu
                100                 105                 110

His Glu Val Lys Cys Arg Gly Thr Glu Thr Met Cys Leu Asp Leu Val
            115                 120                 125

Gly Tyr Arg Gln Glu Ser Tyr Ala Gly Asn Ile Thr Tyr Asn Ile Lys
        130                 135                 140

Gly Cys Val Ser Ser Cys Pro Leu Val Thr Leu Ser Glu Arg Gly His
145                 150                 155                 160

Glu Gly Arg Lys Asn Asp Leu Lys Lys Val Glu Cys Arg Glu Ala Leu
                165                 170                 175

Lys Pro Ala Ser Ser Asp
            180

<210> SEQ ID NO 14
<211> LENGTH: 181
<212> TYPE: PRT
<213> ORGANISM: Agkistrodon blomhoffii siniticus
```

```
<400> SEQUENCE: 14

Arg Ser Cys Asp Tyr Cys His Asn Ile Gly Lys Asp Cys Asp Gly Tyr
 1               5                  10                  15

Glu His Glu Cys Ser Ser Pro Glu Asp Val Cys Gly Lys Val Phe Leu
            20                  25                  30

Glu Ile Ser Ser Ala Ser Leu Ser Val Arg Thr Val His Lys Asn Cys
        35                  40                  45

Phe Ser Ser Val Cys Lys Leu Gly His Phe Asp Ile Asn Ile Gly
    50                  55                  60

His His Ser Tyr Ile Arg Gly Arg Ile Asn Cys Glu Lys Glu Pro
65                  70                  75                  80

Cys Glu Asp Gln Pro Phe Pro Gly Leu Pro Leu Ser Gln Pro Asn Gly
                85                  90                  95

Tyr Tyr Cys Pro Gly Ala Leu Gly Leu Phe Thr Glu Asp Ser Thr Glu
                100                 105                 110

Tyr Glu Ala Ile Cys Lys Gly Thr Glu Thr Lys Cys Ile Asn Ile Val
                115                 120                 125

Gly His Arg His Glu Asn Tyr Pro Gly Asp Ile Ser Tyr Asn Leu Lys
    130                 135                 140

Gly Cys Val Ser Ser Cys Pro Leu Leu Ser Leu Ser Asn Ser Thr His
145                 150                 155                 160

Glu Glu Asn Arg Asn Tyr Leu Glu Lys Val Glu Cys Lys Asp Ala Phe
                165                 170                 175

Lys Ile Ala Ser His
            180

<210> SEQ ID NO 15
<211> LENGTH: 181
<212> TYPE: PRT
<213> ORGANISM: Crotalus d. terrificus

<400> SEQUENCE: 15

Arg Ser Cys Asp Phe Cys His Asn Ile Gly Lys Asp Cys Asp Gly Tyr
 1               5                  10                  15

Glu Glu Glu Cys Ser Ser Pro Glu Asp Val Cys Gly Lys Val Leu Leu
            20                  25                  30

Glu Ile Ser Ser Ala Ser Leu Ser Val Arg Thr Val His Lys Asn Cys
        35                  40                  45

Phe Ser Ser Ser Ile Cys Lys Leu Gly Gln Phe Asp Val Asn Ile Gly
    50                  55                  60

His His Ser Tyr Ile Arg Gly Arg Ile Asn Cys Cys Glu Lys Glu Leu
65                  70                  75                  80

Cys Glu Asp Gln Pro Phe Pro Gly Leu Pro Leu Ser Lys Pro Asn Gly
                85                  90                  95

Tyr Tyr Cys Pro Gly Ala Ile Gly Leu Phe Thr Lys Asp Ser Thr Glu
                100                 105                 110

Tyr Glu Ala Ile Cys Lys Gly Thr Glu Thr Lys Cys Ile Asn Ile Val
                115                 120                 125

Gly His Arg Tyr Glu Gln Phe Pro Gly Asp Ile Ser Tyr Asn Leu Lys
    130                 135                 140

Gly Cys Val Ser Ser Cys Pro Leu Leu Ser Leu Ser Asn Ala Thr Phe
145                 150                 155                 160

Glu Gln Asn Arg Asn Tyr Leu Glu Lys Val Glu Cys Lys Asp Ala Ile
                165                 170                 175
```

Arg Leu Ala Ser Leu
              180

<210> SEQ ID NO 16
<211> LENGTH: 181
<212> TYPE: PRT
<213> ORGANISM: Protobothrops flavoviridis

<400> SEQUENCE: 16

Arg Ser Cys Asp Phe Cys His Asn Ile Gly Ala Asp Cys Glu Gly Phe
1               5                   10                  15

Gln His Glu Cys Ser Ser Pro Glu Asp Cys Gly Lys Val Phe Leu
            20                  25                  30

Glu Ile Ser Ser Ala Ser Leu Ser Val Arg Thr Val His Lys Asn Cys
        35                  40                  45

Phe Ser Ser Val Cys Lys Leu Arg His Phe Asp Val Asn Ile Gly
    50                  55                  60

His Asp Ser Tyr Ile Arg Gly Arg Ile Asn Cys Cys Glu Lys Glu Pro
65                  70                  75                  80

Cys Glu Asp Gln Ser Phe Pro Gly Leu Pro Leu Ser Gln Pro Asn Gly
                85                  90                  95

Tyr Tyr Cys Pro Gly Ser Leu Gly Leu Phe Thr Lys Asp Ser Thr Glu
            100                 105                 110

Phe Glu Ala Ile Cys Lys Gly Thr Glu Thr Lys Cys Ile Asn Ile Val
        115                 120                 125

Gly His Arg Tyr Glu His Tyr Pro Gly Asp Ile Ala Tyr Asn Leu Lys
    130                 135                 140

Gly Cys Ile Ser Ser Cys Pro Leu Leu Ser Leu Ser Asn Ala Thr His
145                 150                 155                 160

Glu Glu Asn Arg Asn Tyr Leu Glu Lys Val Glu Cys Lys Asp Ala Leu
                165                 170                 175

Gln Phe Glu Lys Gln
            180

<210> SEQ ID NO 17
<211> LENGTH: 183
<212> TYPE: PRT
<213> ORGANISM: Elaphe quadrivirgata

<400> SEQUENCE: 17

Arg Ser Cys Glu Ile Cys His Asn Val Gly Asn Asp Cys Gly Tyr Asp
1               5                   10                  15

Tyr Val Glu Glu Cys His Ser Pro Glu Asp Gln Cys Gly Lys Val Leu
            20                  25                  30

Leu Glu Ile Ser Ser Ala Pro Leu Ser Ile Arg Ser Ser His Arg Asn
        35                  40                  45

Cys Phe Ser Ser Leu Cys Lys Leu Glu His Phe Asp Val Asn Thr
    50                  55                  60

Gly Gln Glu Thr Tyr Leu Arg Gly Arg Ile His Cys Cys Asp Glu Lys
65                  70                  75                  80

Lys Cys Glu Gly Arg Pro Phe Pro Gly Leu Pro Leu Ser His Pro Asn
                85                  90                  95

Gly Tyr Val Cys Pro Gly Val Leu Gly Leu Phe Ser Glu Asp Ser Ser
            100                 105                 110

Glu Ser Glu Ala Ala Cys Lys Gly Asp Glu Thr Lys Cys Ile Asn Ile
        115                 120                 125

```
Val Gly Tyr Arg Lys Glu Arg Phe Pro Gly Asp Ile Ala Tyr Asn Ile
        130                 135                 140

Lys Gly Cys Val Ser Ser Cys Pro Glu Leu Arg Leu Ser Asn Arg Thr
145                 150                 155                 160

His Glu Glu Arg Arg Asn Asp Leu Ile Lys Val Glu Cys Arg Asp Ala
                165                 170                 175

Val Lys Ile Thr Pro Ser Glu
            180

<210> SEQ ID NO 18
<211> LENGTH: 183
<212> TYPE: PRT
<213> ORGANISM: Notechis ater

<400> SEQUENCE: 18

Arg Ser Cys Glu Ile Cys His Asn Phe Gly Lys Asp Cys Gly Gly Gly
1               5                   10                  15

Glu Thr Glu Glu Cys Ala Ser Pro Glu Asp Gln Cys Gly Thr Val Leu
            20                  25                  30

Met Glu Val Ser Thr Ala Pro Ile Ser Phe Arg Ser Ile His Arg Asn
        35                  40                  45

Cys Phe Ser Ser Leu Cys Lys Leu Glu Arg Phe Asp Ile Asn Ile
    50                  55                  60

Gly His Asp Ser Phe Leu Arg Gly Arg Ile His Cys Cys Asp Glu Ala
65                  70                  75                  80

Arg Cys Glu Ala Gln Gln Phe Pro Gly Leu Pro Leu Ser Phe Pro Asn
                85                  90                  95

Gly Tyr His Cys Pro Gly Ile Leu Gly Leu Phe Ser Val Asp Ser Ser
            100                 105                 110

Glu His Glu Ala Ile Cys Arg Gly Thr Glu Thr Lys Cys Ile Asn Leu
        115                 120                 125

Ala Gly Phe Arg Arg Glu Arg Phe Pro Gly Asp Ile Ala Tyr Asn Ile
    130                 135                 140

Lys Gly Cys Thr Ser Ser Cys Pro Glu Leu Arg Leu Ser Asn Arg Thr
145                 150                 155                 160

His Glu Glu His Arg Asn Asp Leu Ile Lys Val Glu Cys Thr Glu Ala
                165                 170                 175

Ser Lys Asn Thr Pro Ser Glu
            180

<210> SEQ ID NO 19
<211> LENGTH: 183
<212> TYPE: PRT
<213> ORGANISM: Notechis scutellatus

<400> SE

Arg Cys Glu Ala Gln Gln Phe Pro Gly Leu Pro Leu Ser Phe Pro Asn
                85                  90                  95

Gly Tyr His Cys Pro Gly Ile Leu Gly Val Phe Ser Val Asp Ser Ser
            100                 105                 110

Glu His Glu Ala Ile Cys Arg Gly Thr Glu Thr Lys Cys Ile Asn Leu
        115                 120                 125

Ala Gly Phe Arg Lys Glu Arg Phe Pro Gly Asp Ile Gly Tyr Asn Ile
    130                 135                 140

Lys Gly Cys Thr Ser Ser Cys Pro Glu Leu Arg Leu Ser Asn Arg Thr
145                 150                 155                 160

His Glu Glu Asp Arg Asn Asp Leu Ile Lys Val Glu Cys Thr Asp Ala
                165                 170                 175

Ser Lys Ile Thr Pro Ser Glu
            180

<210> SEQ ID NO 20
<211> LENGTH: 183
<212> TYPE: PRT
<213> ORGANISM: Oxyuranus scutellatus

<400> SEQUENCE

```
<210> SEQ ID NO 22
<211> LENGTH: 28
<212> TYPE: PRT
<213> ORGANISM: Agkistrodon b. siniticus

<400> SEQUENCE: 22

Pro Phe Pro Gly Leu Pro Leu Ser Gln Pro Asn Gly Tyr Tyr Cys Pro
1               5                   10                  15

Gly Ala Leu Gly Leu Phe Thr Glu Asp Ser Thr Glu
            20                  25

<210> SEQ ID NO 23
<211> LENGTH: 28
<212> TYPE: PRT
<213> ORGANISM: Crotalus d. terrificus

<400> SEQUENCE: 23

Pro Phe Pro Gly Leu Pro Leu Ser Lys Pro Asn Gly Tyr Tyr Cys Pro
1               5                   10                  15

Gly Ala Ile Gly Leu Phe Thr Lys Asp Ser Thr Glu
            20                  25

<210> SEQ ID NO 24
<211> LENGTH: 28
<212> TYPE: PRT
<213> ORGANISM: Protobothrops flavoviridis

<400> SEQUENCE: 24

Ser Phe Pro Gly Leu Pro Leu Ser Gln Pro Asn Gly Tyr Tyr Cys Pro
1               5                   10                  15

Gly Ser Leu Gly Leu Phe Thr Lys Asp Ser Thr Glu
            20                  25

<210> SEQ ID NO 25
<211> LENGTH: 28
<212> TYPE: PRT
<213> ORGANISM: Elaphe quadrivirgata

<400> SEQUENCE: 25

Pro Phe Pro Gly Leu Pro Leu Ser His Pro Asn Gly Tyr Val Cys Pro
1               5                   10                  15

Gly Val Leu Gly Leu Phe Ser Glu Asp Ser Ser Glu
            20                  25

<210> SEQ ID NO 26
<211> LENGTH: 28
<212> TYPE: PRT
<213> ORGANISM: Notechis ater

<400> SEQUENCE: 26

Gln Phe Pro Gly Leu Pro Leu Ser Phe Pro Asn Gly Tyr His Cys Pro
1               5                   10                  15

Gly Ile Leu Gly Leu Phe Ser Val Asp Ser Ser Glu
            20                  25

<210> SEQ ID NO 27
<211> LENGTH: 28
<212> TYPE: PRT
<213> ORGANISM: Notechis scutellatus

<400> SEQUENCE: 27
```

```
Gln Phe Pro Gly Leu Pro Leu Ser Phe Pro Asn Gly Tyr His Cys Pro
1               5                   10                  15

Gly Ile Leu Gly Val Phe Ser Val Asp Ser Ser Glu
            20                  25
```

<210> SEQ ID NO 28
<211> LENGTH: 28
<212> TYPE: PRT
<213> ORGANISM: Oxyuranus scutellatus

<400> SEQUENCE: 28

```
Gln Phe Pro Gly Leu Pro Leu Ser Phe Pro Asn Gly Tyr His Cys Pro
1               5                   10                  15

Gly Ile Leu Gly Ala Phe Ser Val Asp Ser Ser Glu
            20                  25
```

<210> SEQ ID NO 29
<211> LENGTH: 28
<212> TYPE: PRT
<213> ORGANISM: Laticauda semifasciaata

<400> SEQUENCE: 29

```
Gln Phe Pro Gly Leu Pro Leu Ser Leu Pro Asn Gly Tyr Tyr Cys Pro
1               5                   10                  15

Gly Ile Leu Gly Leu Phe Thr Val Asp Ser Ser Glu
            20                  25
```

<210> SEQ ID NO 30
<211> LENGTH: 22
<212> TYPE: PRT
<213> ORGANISM: Artificial Sequence
<220> FEATURE:
<223> OTHER INFORMATION: P-0036: Synthetic peptide derived from the
      proline-rich domain; Original source organism: Python reticulatus;
      Custom-synthesized at Biotechnology Processing Centre (BTC), NUS

<400> SEQUENCE: 30

```
Pro Leu Pro Gly Leu Pro Leu Ser Leu Gln Asn Gly Leu Tyr Cys Pro
1               5                   10                  15

Gly Ala Phe Gly Ile Phe
            20
```

<210> SEQ ID NO 31
<211> LENGTH: 15
<212> TYPE: PRT
<213> ORGANISM: Artificial Sequence
<220> FEATURE:
<223> OTHER INFORMATION: P-0008: Synthetic peptide derived from the
      proline-rich domain; Original source organism: Python reticulatus;
      Custom-synthesized at Biotechnology Processing Centre (BTC), NUS

<400> SEQUENCE: 31

```
Pro Leu Pro Gly Leu Pro Leu Ser Leu Gln Asn Gly Leu Tyr Lys
1               5                   10                  15
```

<210> SEQ ID NO 32
<211> LENGTH: 13
<212> TYPE: PRT
<213> ORGANISM: Artificial Sequence
<220> FEATURE:
<223> OTHER INFORMATION: P-0005: Synthetic peptide derived from the
      proline-rich domain; Original source organism: Python reticulatus;
      Custom-synthesized at Biotechnology Processing Centre (BTC), NUS

<400> SEQUENCE: 32

```
Gly Ala Phe Gly Ile Phe Thr Glu Asp Ser Thr Glu Lys
1               5                   10
```

<210> SEQ ID NO 33
<211> LENGTH: 6
<212> TYPE: DNA
<213> ORGANISM: Python reticulatus

<400> SEQUENCE: 33

```
aataaa                                                              6
```

US 7,094,575 B2

THERAPEUTIC AND PROPHYLACTIC AGENTS AND METHODS OF USING SAME

This application is a continuation of PCT/SG00/00201 filed Dec. 7, 2000.

FIELD OF THE INVENTION

This invention relates to novel anti-toxic/anti-inflammatory agents. In particular, the present invention relates to novel agents obtainable from nonvenomous snakes, particularly from *Python* species (especially *Python reticulatus*), for treating envenomation and for treating and preventing phospholipase $A_2$ ($PLA_2$) related inflammatory conditions. The invention also relates to polypeptides and polynucleotides encoding these novel agents and to methods for their manufacture. The invention also extends to pharmaceutical compositions comprising polypeptides encoding these novel agents and to the use of these pharmaceutical compositions for treating envenomation and for treating and preventing $PLA_2$ related inflammatory conditions. Finally, this invention relates to a synthetic decapeptide, and its synthetic chemical analogues or polypeptide variants, that inhibit $PLA_2$ activity and alleviate inflammation, in the diagnosis, study, prevention, and treatment of $PLA_2$ related inflammatory diseases.

BACKGROUND OF THE INVENTION

While lethal bites by Russell's viper (*Daboia russelli siamensis*) pose a serious medical problem in the developing countries of Southeast Asia, the situation is further aggravated by the limited effectiveness of antivenins in snakebite treatment (Warrell, D. A., 1992, *Recent Advances in Toxinology Research*, 1: 121–153, Gopalakrishnakone, P. and Tan, C. K., Eds.), National University of Singapore; Warrell, D. A. 1993 *Med. J. Austr.* 159: 773–779), and hypersensitivity to horse proteins in some patients during serotherapy. Treatment of snakebite, especially that of Russell's viper, would be greatly enhanced, if an antidote could be found which would overcome the aforementioned problems associated with use of commercial antivenins.

Neutralising factors towards this end have been isolated and purified from sera of various mammals and snakes, including antihaemorrhagic factors (Catanese and Kress, 1992, *Biochemistry* 31: 410–418; Yamakawa and Omori-Satoh, 1992, *J. Biochem.* 122: 583–589; Qi, Z.-Q. et al., 1994, *Toxicon* 32: 1459–1469), $PLA_2$-inhibitors (Fortes-Dias et al., 1991, *Toxicon* 29, 997–1008; Perales et al., 1995, *Eur. J. Biochem.* 227: 19–26; Kogaki et al., 1989, *J. Biochem.* 106, 966–971; Ohkura et al., 1993, *J. Biochem.* 113, 413–419) and anti-myotoxic factor (Inoue et al., 1997, *Biochem. Mol. Bio. Inter.*, 49: 529–537). The high neutralising capacity against skin haemorrhage induced by several haemorrhagic venoms seems to be a common feature among the antihaemorrhagic factors, but their neutralising activity against venom toxins has not been tested properly and hence no claim has been made so far as to the use of antihaemorrhagic factor(s) for treating snakebite.

$PLA_2$ is a major component of snake venoms that contributes to different pathological effects of snakebite such as neurotoxicity and myotoxicity, haemostatic disturbance, haemolysis, cardiotoxicity and hypotension. Two antitoxic $PLA_2$ inhibitors, namely the crotalus neutralising factor (CNF) and crotoxin inhibitor from crotalus serum (CICS), have been purified and characterised from the serum of a South American rattlesnake, *Crotalus d. terrificus* (Fortes-Dias et al., supra; Perales et al., supra). Both are oligomeric glycoproteins with molecular weights in the range of 130–160 kDa and subunit molecular masses of around 23–25 kDa, and act specifically by neutralising crotoxin, the main toxic component with potent $PLA_2$ activity from the South American rattlesnake venom. Although CICS and CNF appear to be the most likely candidates for use as antidotes against *Crotalus* snake poisoning, their effectiveness against the lethal toxicity of heterologous venoms from viperid snakes like Russell's viper is yet to be tested.

Two more $PLA_2$ inhibitors with molecular weights of 100 kDa and 75 kDa, from crotalid snakes, *Trimeresurus flavoviridis* and *Agkistrodon b. siniticus*, respectively (Kogaki et al., supra; Ohkura et al., supra), and another 90-kDa $PLA_2$ inhibitor from an Elapidae, *Naja naja kaouthia* (Inoue et al., supra) have also been purified, but their capacity to inhibit the toxic effects of the venoms has not been reported. Recently, a $PLA_2$ inhibitor named *Bothrops asper* myotoxin inhibitor protein (BaMIP), which is an oligomer (molecular weight 120 kDa) composed of five 23–25 kDa subunits, has been purified from the blood plasma of *Bothrops asper* (Lizano et al., 1997, *Biochem. J.* 326: 853–859). Although it is active in inhibiting the in vitro $PLA_2$ catalytic activity and the myotoxic and oedematogenic activities of the *B. asper* myotoxin isoforms, its neutralising activity against the lethal or systemic action of snake venom or toxin has not been reported.

Despite the above advances, Russell's viper bite is still posing a major life-threatening health problem in the Southeast Asia region. Thousands of bites by this snake occur yearly, resulting in an annual mortality of more than 100 in Myanmar alone (Myint-Lwin et al., 1985 *Lancet* II 1259–1264). Clinical studies using Russell's viper antivenins produced from different sources have indicated that one product from one area of the region is clinically much less effective for treating bites by another subspecies of Russell's viper in a different locality (Phillips et al., 1988, *Quart, J. Med.* 68, 691–716). A cocktail of venoms from different Russell's viper subspecies would therefore be desirable to give a broad spectrum of protective antibodies, but this has yet to happen.

From the foregoing, an antivenin drug that will neutralise the toxicity of Russell's viper venoms from all subspecies will have enormous potential as an antidote for all Russell's viper bites, irrespective of subspecies differences. Moreover, a drug having neutralising activity not only for Russell's viper venoms but also for venoms of all major snake species will be a major breakthrough.

$PLA_2$ enzymes have been identified and purified from bovine, porcine, and human pancreas (Fleer et al., 1978, *Eur. J. Biochem.* 82: 261–269; Verheij et al., 1983, *Biochem. Biophys. Acta* 747: 93–99; Puijk et al., 1977, *Biochem. Biophys. Acta* 492: 254–259), and in human synovial fluid aspirates from rheumatoid and osteoarthritis patients (Parks et al., 1990, *Adv. Exp. Med. Biol.* 275: 55–81; Seilhames et al, 1989, *J. Biochem.* (Tokyo) 106: 38–42). Because of their implication in a range of diseases including rheumatoid and osteoarthritis, asthma, acute pancreatitis, septic shock, etc. (Vadas et al., 1986, *Lab. Invest.* 55: 391–404; Vadas et al., 1993, *J. Lipid Med.* 8: 1–30; Michaels et al., 1994, *Biochem. Pharmacol.* 48: 1–10), recent research has focused on the role of $PLA_2$-inhibitors (PLIs) as possible anti-inflammatory agents (Glaser, 1995, *Advances in Pharmaco.* 32: 31–66). A number of PLIs have thus been purified and characterized from a variety of sources, including plant, fungi, and bacteria (Cuellar et al., 1996, *J. Nat. Prod.* 59: 977–979; Matsumoto et al., 1995, *J. Antibiotics* 48: 106–112; Lindahl et al., 1997, *Inflammation* 21: 347–356). Additionally, PLIs that interact with PLA$_2$s and inhibit their enzymatic activity, have been purified almost entirely from the sera of venomous snakes belonging to Elapidae and Crotalidae families (Thwin et al., 1988, *Toxicon* 36: 1471–1482; Ohkura et al., 1999, *J. Biochem.* (Tokyo) 125: 375–382; Okumura et al., 1998, *J. Biol. Chem.* 273: 19469–19473; Hains et al., 2000, *J. Biol. Chem.* 275: 983–991). However, very little attempt has so far been made to produce recombinant proteins that are functionally active as the native inhibitors, nor to study the therapeutic relevance of the recombinant PLA$_2$ inhibitors. Recently, a PLI with potent antitoxic and anti-inflammatory activities has been purified for the first time by us, from the serum of the non-venomous snake *Python reticulatus* (Thwin et al., 1999, *Toxicon* 37: 1465). This PLI, initially termed PAF (Python Antitoxic Factor), and later renamed as PIP (Phospholipase Inhibitor from Python), has also been cloned, sequenced, and functionally expressed as fusion protein in *Escherichia coli* (Thwin et al., 2000, *Biochemistry* [accepted for publication]). A broad aspect of this invention concerns the potential therapeutic significance of this recombinant inhibitor protein as an antidote for snakebite and other PLA$_2$-related inflammatory conditions.

While the recombinant inhibitor protein can be used either alone or in combination with the neutralizing antibodies to improve the efficacy of commercial antivenins, we have noted that the structural information obtained from our previous study on the inhibitor protein can be effectively utilized to identify small molecular weight short peptides that may act as a surrogate for the larger molecule and be useful as potential anti-inflammatory agent. This will improve the therapeutic usefulness, and at the same time help to reduce the untoward effects commonly associated with the use of high molecular weight homologous or heterologous complexes like the recombinant protein. Short peptides called antiflammins that are synthesized based on the region of highest homology between uteroglobin and lipocortin I, have previously been shown to inhibit PLA$_2$ (Snyder et al., 1999, *J. Pharmacol. Exp. Ther.* 288: 1117–1124; Rodgers et al., 1997, *J. Invest. Surgery* 10: 31–36), although there are some reports suggesting that these antiflammins are devoid of PLA$_2$ inhibitory activity (Marastoni et al., 1993, *Drug Res.* 43: 997–1000; Hope et al., 1991, *Agents & Actions* 34: 77–80). Development of such small molecular weight peptide inhibitors has been the goal of researchers at many pharmaceutical companies. In this study, a family of oligopeptides corresponding to a region of high amino acid sequence similarity between PIP (Thwin et al., 2000, GENBANK Accession No. AF 232771) and other structurally related snake serum PLIs have been synthesized and examined for their anti-inflammatory activity. Thus another aspect of this invention relates to the synthetic decapeptide that shows potent in vitro PLA$_2$ inhibitory activity and striking anti-inflammatory effects in vivo.

SUMMARY OF THE INVENTION

The present invention in its broadest aspect arises from the unexpected discovery of an endogenous antitoxic agent in an extract obtained from the nonvenomous snake *Python reticulatus*. The inventors have shown that this novel agent abolishes the lethal toxicity of venoms from different Russell's viper subspecies with a potency superior to that of commercial antivenins. It also has been shown to have a generic capacity to neutralise lethal doses of venoms and PLA$_2$ toxins, not only from a variety of different snakes, including those belonging to the major snake families Crotalidae, Elapidae and Viperidae, but also from different insects including bees and scorpions. The inventors have also found that it possesses a strong anti-inflammatory activity and is thus useful for treating or preventing PLA$_2$-related inflammatory conditions.

Accordingly, in one aspect of the present invention, there is provided an isolated extract of a *Python* species, which extract ameliorates conditions associated with envenomation and/or inflammation.

Suitably, the extract is characterised in that it neutralises or inhibits a venom or toxin. Preferably, the venom or toxin comprises as an active component a phospholipase. Preferably the phospholipase is a phospholipase A$_2$.

Suitably, the extract is obtained from serum of the said species.

Preferably, the *Python* species is *P. reticulatus*.

Suitably, the extract comprises as an active component a polypeptide having a molecular mass of about 23-kDa.

Preferably, the polypeptide self associates to form an oligomer of about 140-kDa.

In a preferred aspect, the invention resides in an isolated polypeptide or a biologically active fragment thereof, or a variant or derivative of these, said polypeptide comprising the sequence set forth in SEQ ID NO: 6.

The polypeptide may comprise a leader peptide. Suitably, the leader peptide comprises the sequence of amino acids set forth in SEQ ID NO: 8, or a biologically-active fragment thereof, or variant or derivative of these.

In another aspect, the invention provides an isolated polynucleotide encoding a polypeptide, fragment, variant or derivative as broadly described above. Preferably, the polynucleotide comprises the sequence set forth in SEQ ID NO: 5, or a biologically active fragment thereof, or a polynucleotide variant of these.

The polynucleotide preferably comprises a nucleotide sequence encoding a leader peptide. Suitably, said nucleotide sequence comprises the sequence set forth in SEQ ID NO: 7 or a biologically active fragment thereof, or a polynucleotide variant of these.

Preferably, the variant is obtained from a species of *Python*. Suitably, the variant is obtained from the liver of said species.

In another aspect, the invention features an expression vector comprising a polynucleotide as broadly described above wherein the polynucleotide is operably linked to one or more regulatory nucleic acids.

In a further aspect, the invention provides a host cell containing a said expression vector.

The invention also contemplates a method of producing a polypeptide, fragment, variant or derivative as broadly described above, comprising:
 (a) culturing a host cell containing an expression vector as broadly described above such that said polypeptide, fragment, variant or derivative is expressed from said polynucleotide; and
 (b) isolating the said polypeptide, fragment, variant or derivative.

In a further aspect, the invention provides a method of producing a biologically active fragment as broadly described above, comprising:
 (a) producing a fragment of said polypeptide;
 (b) administering the fragment to an animal; and
 (c) challenging the animal with a dosage of a venom or toxin, which dosage in the absence of the fragment invokes lethality or disease in the animal;

wherein protection against lethality or disease in the animal is indicative of said fragment being a biologically active fragment.

In yet another aspect, the invention contemplates a method of producing a polypeptide variant of a parent polypeptide comprising the sequence set forth in SEQ ID NO: 2 or 6, or biologically active fragment thereof, comprising the steps of:
(a) replacing at least one amino acid of the parent polypeptide, with a different amino acid to produce a modified polypeptide;
(b) combining the modified polypeptide with a phospholipase $A_2$; and
(c) detecting the presence of a conjugate comprising the modified polypeptide and the phospholipase $A_2$, which is indicative of the modified polypeptide being said polypeptide variant.

According to another aspect of the invention, there is provided a method of producing a polypeptide variant of a parent polypeptide comprising the sequence set forth in SEQ ID NO: 2 or 6, or biologically active fragment thereof, comprising the steps of:
(a) replacing at least one amino acid of the parent polypeptide, with a different amino acid to produce a modified polypeptide;
(b) administering the modified polypeptide to an animal; and
(c) challenging the animal with a dosage of a venom or toxin, which dosage in the absence of the compound invokes lethality or disease in the animal;
wherein protection against lethality or disease in the animal is indicative of the modified polypeptide being said polypeptide variant.

In another aspect, the invention provides a composition for use in treating envenomation, comprising a polypeptide, biologically active fragment, variant or derivative as broadly described above, together with a pharmaceutically acceptable carrier.

In yet another aspect, the invention provides a composition for use in treating or preventing inflammatory conditions, comprising a polypeptide, biologically active fragment, variant or derivative as broadly described above, together with a pharmaceutically acceptable carrier.

According to a further aspect, the invention provides a method for treatment of envenomation, comprising administering to a patient in need of such treatment a therapeutically effective amount of a composition as broadly described above.

The invention, in another aspect, resides in a method for treatment or prophylaxis of an inflammatory condition, comprising administering to a patient in need of such treatment a therapeutically effective amount of a composition as broadly described above.

Preferably, the inflammatory condition is a phospholipase $A_2$ associated inflammatory condition. Suitably, the phospholipase $A_2$ associated inflammatory condition includes, but is not limited to, bacterial or fungal infections, osteoarthritis, rheumatoid arthritis, and osteoporosis.

In another aspect, the invention resides in the use of a polypeptide, fragment, variant or derivative according to the present invention to produce an antigen-binding molecule that binds to the said polypeptide, fragment, variant or derivative.

In yet another aspect, the invention provides antigen-binding molecules so produced.

According to another aspect of the invention, there is provided a method of detecting in a sample a polypeptide, fragment, variant or derivative as broadly described above, comprising:
(a) contacting the sample with an antigen-binding molecule as broadly described above; and
(b) detecting the presence of a complex comprising the said antigen-binding molecule and the said polypeptide, fragment, variant or derivative in said contacted sample.

In another aspect of the invention, there is provided a method of detecting a phospholipase $A_2$ in a biological sample of a patient, comprising:
(a) contacting the biological sample with a polypeptide, fragment, variant or derivative as broadly described above; and
(b) detecting the presence of a complex comprising the said polypeptide, fragment, variant or derivative and the phospholipase $A_2$ in said contacted sample.

The invention also features a method of diagnosing a condition associated with an aberrant concentration of a phospholipase $A_2$ in a biological sample of a patient, comprising:
(a) contacting the biological sample with a polypeptide, fragment, variant or derivative as broadly described above;
(b) measuring the concentration of a complex comprising the said polypeptide, fragment, variant or derivative and the phospholipase $A_2$ in said contacted sample; and
(c) relating said measured complex concentration to the concentration of phospholipase $A_2$ in said sample, wherein the presence of said aberrant concentration is indicative of said condition.

The invention also encompasses the use of the polypeptide, fragment, variant or derivative as broadly described above in the study, treatment and prevention of envenomation.

Preferably, the use is characterised in that said envenomation results from a snake, insect or fish.

In the case of snake envenomation, the snake is preferably a Russell's viper species.

In the case of insect envenomation, the insect is preferably a scorpion or a bee.

The invention also extends to the use of the polypeptide, fragment, variant or derivative according to the present invention in a kit for detecting and/or measuring a phospholipase $A_2$ in a biological sample.

Thus a preferred aspect of the present invention relates to the novel anti-inflammatory peptide derived from the amino acid sequence of a novel anti-toxic and anti-inflammatory protein, which was termed initially "Python Antitoxic Factor" (PAF) but was later renamed "Phospholipase Inhibitor from Python" (PIP). The nucleic acid and protein sequences of PAF or PIP are described in detail hereinbelow. PIP is a 140-kDa hexameric glycoprotein formed by six identical 23-kDa subunits of 182 amino acids each. Both the native PIP as well as its functional equivalent recombinant protein has proven anti-toxic and anti-inflammatory properties.

The phospholipase $A_2$ ($PLA_2$) inhibitory peptide which constitutes a preferred embodiment of the present invention was identified through a computer generated search for amino acid sequence alignments between PIP and database amino acid sequences of $PLA_2$ inhibitors from the sera of snakes, which have sequence identities around 60% and whose matches satisfy the pre-set E-value of 0.001. When a family of synthetic peptides corresponding to the highly conserved proline-rich hydrophobic region of PIP and database matched sequences are examined for their anti-inflammatory activity, a decapeptide (P-0029) proves the most potent of those tested in inhibiting in vitro $PLA_2$ catalytic activity and exhibits striking anti-inflammatory effects in vivo, in a mouse paw oedema model and also in a rat model of intraperitoneal adhesion formation. This decapeptide P-0029 provides nearly complete suppression of the inflammatory response in both in vivo model systems, indicating that the small molecular weight peptide retains almost all the anti-inflammatory activity of the parent PIP protein and can act as a surrogate for the larger inhibitory protein. Hence, the small molecular weight decapeptide P-0029, herein referred to as SEQ ID NO:10, will definitely improve the potential therapeutic usefulness for inflammatory conditions, with the possible benefit provided in reducing the side-effects usually associated with the use of high molecular weight native or recombinant protein inhibitor drugs.

The anti-inflammatory decapeptide P-0029 (SEQ ID NO:10) in particular, and those peptides with strong in vitro $PLA_2$-inhibitory activity in general, the amino acid sequences of which are herein referred to as SEQ ID NO:11 and SEQ ID NO:12 for the decapeptide P-0009 and the nonapeptide P-0006 respectively, and any other similar sequences or portions thereof, produced by means of synthetic chemistry or by recombinant DNA technology, are related to the present invention and can be used for the study, prevention and treatment of any diseases which are known to be related with $PLA_2$ activity.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 shows the inhibitory activity of crude python serum against the $PLA_2$ enzymatic activity and neurotoxicity of the $PLA_2$ toxin, DbTx, and against the indirect-haemolytic activity of Russell's viper venom: (A) inhibition profiles of $^{125}$I-DbTx specific binding to rat brain synaptosomes displayed by sera of *Python reticulatus* and other animals; (B) inhibitory effect of python serum (o) on $PLA_2$ activity of DbTx in comparison to that of control human serum (9) and of specific anti-DbTx immune serum (ϵ); (C) inhibitory activity of python serum ( ) and sera of little civet cat (~), peafowl (∈), monkey (∉ and Russell's viper anti-venin ( )on the indirect haemolytic activity of Russell's viper venom.

FIG. 2 shows the chromatographic profiles of samples obtained during the purification process: (A) FPLC profile of 45–80% ammonium sulphate precipitated python serum proteins obtained from anion exchange UNO Q1™ column eluted with 0.025M to 0.5M salt gradient in Tris-HCL buffer (pH 8.2). Fraction X represents active fraction with inhibitory activity against lethal and $PLA_2$ activity of Russell's viper venom; (B) FPLC profile of HiLoad™ 16/60 Superdex™ 75 preparative gel filtration chromatography under denaturing conditions using 8M urea-0.05M Tris-HCl buffer, pH 7.2 as eluant. Peak number X-I represents the purified PAF; (C) C18 Sephasil™ reverse phase HPLC profile of PAF eluted with a gradient of 0–60% of 80% acetonitrile/0.1% trifluoroacetic acid. Peak X-II represents the PAF monomer subunit with a molecular mass of 23-kDa that was used for N-terminal sequencing.

FIG. 3: (A) 12% SDS-PAGE electrophoretic profiles of PAF and its fractions obtained during the purification process. Lanes: (1) standard markers; (2) crude serum; (3) ammonium sulphate precipitated serum fraction; (4) fraction X-II; (5) fraction X-I; (6) fraction X; (B) immobilised semi-purified PAF (fraction X; lane 2) and purified PAF (fraction X-I; lane 3) on nitrocellulose membrane visualised for glycoprotein using the BioRad Immunoblot kit following SDS-PAGE and Western blot electrotransfer of the proteins. The positions of pre-stained (Blue) standard molecular weight markers (lane 1) are also indicated.

FIG. 4 shows Coomassie-stained 12% SDS-PAGE gel profiles of PAF recombinant protein from cleared *E. coli* cell lysates obtained under denaturing conditions. (A) Time course of expression of 6xHis-tagged PAF induced with 1 mM IPTG. Lane 1: pQE-30 expression vector without insert; lane 2: uninduced control; lanes 3–6: 1, 2, 3, 4 h post-induction; lane 7: markers. (B) Purification of recombinant PAF on Ni-NTA column. Lanes 1–8: flow-through, wash 1, wash 2, eluates corresponding to 100, 150, 200, 400, 800 mM imidazole; lane 9: mol. wt. marker; lane 10: native PAF.

FIG. 5 shows that the native or recombinant PAF is an oligomeric high molecular weight protein. (A) Aliquots of native PAF after cross-linking with varying concentrations of bis(sulfosuccinimidyl) substrate (lanes 1–6: 0, 0.25, 0.5, 1, 2.5, 5 mM cross-linker; lane 7: mol. wt. marker) and (B) Recombinant PAF after cross-linking (lanes 1–7: 0, 0.25, 0.5, 1, 2.5, 5, 10 mM bis(sulfosuccinimidyl) substrate; lane 8: marker), followed by SDS-PAGE (reducing) and Coomassie staining in both cases, showing formation of an oligomer with an apparent molecular mass of about 140-kDa.

FIG. 6 shows the alignment of the mature PIP monomer with the database sequences whose match satisfies the pre-set E-value of 0.001. The shaded boxes indicate residues identical to those of PIP. (1) *Python reticulatus* PIP (SEQ ID NO:13); (2) *Agkistrodon blomhoffii siniticus* PLIγ (SEQ ID NO:14); (3) *Crotalus d. terrificus* CNF (SEQ ID NO:15); (4) *Protobothrops flavoviridis* PLIγ (SEQ ID NO:16); (5) *Elaphe quadrivirgata* PLIγ (SEQ ID NO:17); (6) *Notechis ater* α subunit isoform NAI-3A (SEQ ID NO:18); (7) *Notechis scutatus* α chain iii (SEQ ID NO: 19); (8) *Oxyuranus scutellatus* α subunit isoform OSI-1A (SEQ ID NO:20).

FIG. 7 shows the high amino acid sequence homology between PIP (SEQ ID NO:21) and related snake serum PLI sequences (SEQ ID NO:22 through SEQ ID NO:29) that contain unique proline-rich peptide motifs. Residues identical to those of PIP are shown as shaded boxes.

FIG. 8 provides phospholipase $A_2$ inhibition curves for a family of synthetic peptides versus (A) daboiatoxin and (B) venom of the Viperid snake *Daboia russelli siamensis*. $IC_{50}$ values were graphically determined from the inhibition curve A, constructed on the basis of the in vitro results of $^3$H-labelled *E. coli* membrane assays. Results are expressed as mean±SD.

FIG. 9 illustrates the adhesion formed between the mesh and the caecum in the abdominal cavity of the sacrificed rats following 1 week after surgery in an in vivo incisional hernia model. The overall adhesion scores are graded from 1 to 4. Grade 1 and Grade 4 represent the minimal and maximal degree of adhesions, respectively.

FIG. 10 shows the pre- and post-operative tissue phospholipase $A_2$ activity of rats in the absence and presence of the active inhibitory decapeptide P-0029, designated in the figure as P1. In FIG. 10, * designates before operation vs after operation without the inhibitor P1 ($P<0.05$), and ** designates after operation without P1 vs after operation with P1 ($P<0.01$).

1. Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

"Amplification product" refers to a nucleic acid product generated by nucleic acid amplification techniques.

By "antigen-binding molecule" is meant a molecule that has binding affinity for a target antigen. It will be understood that this term extends to immunoglobulins, immunoglobulin fragments and non-immunoglobulin derived protein frameworks that exhibit antigen-binding activity.

The terminology "biologically active" is used herein in connection with various assay methods, including: inhibition of phospholipase $A_2$ activity and/or alleviation of inflammation or conditions associated with envenomation; protection against lethality and/or disease in an animal; and contacting brain cells or tissues with a compound to be tested, followed by contacting the cells or tissues with a venom-derived toxin which binds the cells or tissues in the absence of the compound, wherein inhibition of said binding is indicative that the compound is biologically active.

By "biologically active fragment" is meant a fragment of a full-length parent polypeptide which fragment retains the activity of the parent polypeptide. A biologically active fragment will therefore inhibit phospholipase $A_2$ activity and/or alleviate inflammation or conditions associated with envenomation. As used herein, the term "biologically active fragment" includes deletion mutants and small peptides, for example of at least 10, preferably at least 20 and more preferably at least 30 contiguous amino acids, which comprise the above activities. Peptides of this type may be obtained through the application of standard recombinant nucleic acid techniques or synthesised using conventional liquid or solid phase synthesis techniques. For example, reference may be made to solution synthesis or solid phase synthesis as described, for example, in Chapter 9 entitled "*Peptide Synthesis*" by Atherton and Shephard which is included in a publication entitled "*Synthetic Vaccines*" edited by Nicholson and published by Blackwell Scientific Publications. Alternatively, peptides can be produced by digestion of a polypeptide of the invention with proteinases such as endoLys-C, endoArg-C, endoGlu-C and staphylococcus V8-protease. The digested fragments can be purified by, for example, high performance liquid chromatographic (HPLC) techniques.

The term "biological sample" as used herein refers to a sample that may be extracted, untreated, treated, diluted or concentrated from a patient. Suitably, the biological sample is selected from the group consisting of whole blood, serum, plasma, saliva, urine, sweat, ascitic fluid, peritoneal fluid, synovial fluid, amniotic fluid, cerebrospinal fluid, skin biopsy, and the like.

By "condition associated with an aberrant concentration" is meant any condition including a healthy condition or an unhealthy condition that is associated with a concentration of phospholipase $A_2$ that deviates significantly from a corresponding normal concentration range. "Normal concentration range" is used herein to refer to $PLA_2$ levels in the biological fluids of normal subjects, which is generally from about 10 to 100 ng/ml of fluid. Suitably, the condition is associated with envenomation and/or inflammation.

By "corresponds to" or "corresponding to" is meant a polynucleotide (a) having a nucleotide sequence that is substantially identical or complementary to all or a portion of a reference polynucleotide sequence or (b) encoding an amino acid sequence identical to an amino acid sequence in a peptide or protein. This phrase also includes within its scope a peptide or polypeptide having an amino acid sequence that is substantially identical to a sequence of amino acids in a reference peptide or protein.

By "derivative" is meant a polypeptide that has been derived from the basic sequence by modification, for example by conjugation or complexing with other chemical moieties or by post-translational modification techniques as would be understood in the art. The term "derivative" also includes within its scope alterations that have been made to a parent sequence including additions, or deletions that provide for functionally equivalent molecules. Accordingly, the term derivative encompasses molecules that will inhibit phospholipase $A_2$ activity and/or ameliorate inflammation and conditions associated with envenomation.

"Homology" refers to the percentage number of amino acids that are identical or constitute conservative substitutions as defined in TABLE 1 infra. Homology may be determined using sequence comparison programs such as GAP (Deveraux et al. 1984, *Nucleic Acids Research* 12, 387–395). In this way, sequences of a similar or substantially different length to those cited herein might be compared by insertion of gaps into the alignment, such gaps being determined, for example, by the comparison algorithm used by GAP.

"Hybridisation" is used herein to denote the pairing of complementary nucleotide sequences to produce a DNA-DNA hybrid or a DNA-RNA hybrid. Complementary base sequences are those sequences that are related by the base-pairing rules. In DNA, A pairs with T and C pairs with G. In RNA U pairs with A and C pairs with G. In this regard, the terms "match" and "mismatch" as used herein refer to the hybridisation potential of paired nucleotides in complementary nucleic acid strands. Matched nucleotides hybridise efficiently, such as the classical A-T and G-C base pair mentioned above. Mismatches are other combinations of nucleotides that do not hybridise efficiently.

By "isolated" is meant material that is substantially or essentially free from components that normally accompany it in its native state. For example, an "isolated polynucleotide", as used herein, refers to a polynucleotide, which has been purified from the sequences which flank it in a naturally occurring state, e.g., a DNA fragment which has been removed from the sequences which are normally adjacent to the fragment.

By "obtained from" is meant that a sample such as, for example, a nucleic acid extract or polypeptide extract is isolated from, or derived from, a particular source of the host. For example, the extract may be obtained from a tissue or a biological fluid isolated directly from the host.

The term "oligonucleotide" as used herein refers to a polymer composed of a multiplicity of nucleotide units (deoxyribonucleotides or ribonucleotides, or related structural variants or synthetic analogues thereof) linked via phosphodiester bonds (or related structural variants or synthetic analogues thereof). Thus, while the term "oligonucleotide" typically refers to a nucleotide polymer in which the nucleotides and linkages between them are naturally occurring, it will be understood that the term also includes within its scope various analogues including, but not restricted to, peptide nucleic acids (PNAs), phosphoramidates, phosphorothioates, methyl phosphonates, 2-O-methyl ribonucleic acids, and the like. The exact size of the molecule may vary depending on the particular application. An oligonucleotide is typically rather short in length, generally from about 10 to 30 nucleotides, but the term can refer to molecules of any length, although the term "polynucleotide" or "nucleic acid" is typically used for large oligonucleotides.

By "operably linked" is meant that transcriptional and translational regulatory nucleic acids are positioned relative to a polypeptide-encoding polynucleotide in such a manner that the polynucleotide is transcribed and the polypeptide is translated.

The term "patient" refers to patients of human or other mamma and includes any individual it is desired to examine or treat using the methods of the invention. However, it will be understood that "patient" does not imply that symptoms are present. Suitable mammals that fall within the scope of the invention include, but are not restricted to, primates, livestock animals (eg. sheep, cows, horses, donkeys, pigs), laboratory test animals (eg. rabbits, mice, rats, guinea pigs, hamsters), companion animals (eg. cats, dogs) and captive wild animals (eg. foxes, deer, dingoes).

By "pharmaceutically-acceptable carrier" is meant a solid or liquid filler, diluent or encapsulating substance that may be safely used in topical or systemic administration.

The term "polynucleotide" or "nucleic acid" as used herein designates mRNA, RNA, cRNA, cDNA or DNA. The term typically refers to oligonucleotides greater than 30 nucleotides in length.

The terms "polynucleotide variant" and "variant" refer to polynucleotides displaying substantial sequence identity with a reference polynucleotide sequence or polynucleotides that hybridise with a reference sequence under stringent conditions that are defined hereinafter. These terms also encompasses polynucleotides in which one or more nucleotides have been added or deleted, or replaced with different nucleotides. In this regard, it is well understood in the art that certain alterations inclusive of mutations, additions, deletions and substitutions can be made to a reference polynucleotide whereby the altered polynucleotide retains the biological function or activity of the reference polynucleotide. The terms "polynucleotide variant" and "variant" also include naturally occurring allelic variants.

"Polypeptide", "peptide" and "protein" are used interchangeably herein to refer to a polymer of amino acid residues and to variants and synthetic analogues of the same. Thus, these terms apply to amino acid polymers in which one or more amino acid residues is a synthetic non-naturally occurring amino acid, such as a chemical analogue of a corresponding naturally occurring amino acid, as well as to naturally-occurring amino acid polymers.

The term "polypeptide variant" refers to polypeptides in which one or more amino acids have been replaced by different amino acids. It is well understood in the art that some amino acids may be changed to others with broadly similar properties without changing the nature of the activity of the polypeptide (conservative substitutions) as described hereinafter. Accordingly, polypeptide variants as used herein encompass polypeptides that will inhibit phospholipase $A_2$ activity and/or alleviate inflammation or conditions associated with envenomation.

By "primer" is meant an oligonucleotide which, when paired with a strand of DNA, is capable of initiating the synthesis of a primer extension product in the presence of a suitable polymerising agent. The primer is preferably single-stranded for maximum efficiency in amplification but may alternatively be double-stranded. A primer must be sufficiently long to prime the synthesis of extension products in the presence of the polymerisation agent. The length of the primer depends on many factors, including application, temperature to be employed, template reaction conditions, other reagents, and source of primers. For example, depending on the complexity of the target sequence, the oligonucleotide primer typically contains 15 to 35 or more nucleotides, although it may contain fewer nucleotides. Primers can be large polynucleotides, such as from about 200 nucleotides to several kilobases or more. Primers may be selected to be "substantially complementary" to the sequence on the template to which it is designed to hybridise and serve as a site for the initiation of synthesis. By "substantially complementary", it is meant that the primer is sufficiently complementary to hybridise with a target nucleotide sequence. Preferably, the primer contains no mismatches with the template to which it is designed to hybridise but this is not essential. For example, non-complementary nucleotides may be attached to the 5' end of the primer, with the remainder of the primer sequence being complementary to the template. Alternatively, non-complementary nucleotides or a stretch of non-complementary nucleotides can be interspersed into a primer, provided that the primer sequence has sufficient complementarity with the sequence of the template to hybridise therewith and thereby form a template for synthesis of the extension product of the primer.

"Probe" refers to a molecule that binds to a specific sequence or sub-sequence or other moiety of another molecule. Unless otherwise indicated, the term "probe" typically refers to a polynucleotide probe that binds to another nucleic acid, often called the "target nucleic acid", through complementary base pairing. Probes may bind target nucleic acids lacking complete sequence complementarity with the probe, depending on the stringency of the hybridisation conditions. Probes can be labelled directly or indirectly.

The term "recombinant polynucleotide" as used herein refers to a polynucleotide formed in vitro by the manipulation of nucleic acid into a form not normally found in nature. For example, the recombinant polynucleotide may be in the form of an expression vector. Generally, such expression vectors include transcriptional and translational regulatory nucleic acid operably linked to the nucleotide sequence.

By "recombinant polypeptide" is meant a polypeptide made using recombinant techniques, i.e., through the expression of a recombinant polynucleotide.

By "reporter molecule" as used in the present specification is meant a molecule that, by its chemical nature, provides an analytically identifiable signal that allows the detection of a complex comprising an antigen-binding molecule and its target antigen. The term "reporter molecule" also extends to use of cell agglutination or inhibition of agglutination such as red blood cells on latex beads, and the like.

Terms used to describe sequence relationships between two or more polynucleotides or polypeptides include "reference sequence", "comparison window", "sequence identity", "percentage of sequence identity" and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of typically 12 contiguous residues that is compared to a reference sequence. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerised implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., 1997, Nucl. Acids Res. 25:3389. A detailed discussion of sequence analysis can be found in Unit 19.3 of Ausubel et al., "Current Protocols in Molecular Biology", John Wiley & Sons Inc, 1994–1998, Chapter 15.

The term "sequence identity" as used herein refers to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. For the purposes of the present invention, "sequence identity" will be understood to mean the "match percentage" calculated by the DNASIS computer program (Version 2.5 for windows; available from Hitachi Software engineering Co., Ltd., South San Francisco, Calif., USA) using standard defaults as used in the reference manual accompanying the software.

"Stringency" as used herein, refers to the temperature and ionic strength conditions, and presence or absence of certain organic solvents, during hybridisation. The higher the stringency, the higher will be the degree of complementarity between immobilised nucleotide sequences and the labelled polynucleotide sequence.

"Stringent conditions" refers to temperature and ionic conditions under which only nucleotide sequences having a high frequency of complementary bases will hybridise. The stringency required is nucleotide sequence dependent and depends upon the various components present during hybridisation. Generally, stringent conditions are selected to be about 10 to 20° C. lower than the thermal melting point ($T_m$) for the specific sequence at a defined ionic strength and pH. The $T_m$ is the temperature (under defined ionic strength and pH) at which 50% of a target sequence hybridises to a complementary probe.

The term "substantially pure" as used herein describes a compound, e.g., a peptide that has been separated from components that naturally accompany it. Typically, a compound is substantially pure when at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides, by chromatography, gel electrophoresis or HPLC analysis. A compound, e.g., a polypeptide is also substantially purified when it is essentially free of naturally associated components when it is separated from the native contaminants which accompany it in its natural state.

By "therapeutically effective amount", in the context of the treatment of envenomation, inflammation or a condition associated with aberrant levels of phospholipase $A_2$ activity, is meant the administration of that amount to an individual in need of such treatment, either in a single dose or as part of a series, that is effective for treatment of that condition. The effective amount will vary depending upon the health and physical condition of the individual to be treated, the taxonomic group of individual to be treated, the formulation of the composition, the assessment of the medical situation, and other relevant factors. It is expected that the amount will fall in a relatively broad range that can be determined through routine trials.

By "vector" is meant a nucleic acid molecule, preferably a DNA molecule derived, for example, from a plasmid, bacteriophage, or plant virus, into which a nucleic acid sequence may be inserted or cloned. A vector preferably contains one or more unique restriction sites and may be capable of autonomous replication in a defined host cell including a target cell or tissue or a progenitor cell or tissue thereof, or be integrable with the genome of the defined host such that the cloned sequence is reproducible. Accordingly, the vector may be an autonomously replicating vector, i.e., a vector that exists as an extrachromosomal entity, the replication of which is independent of chromosomal replication, e.g., a linear or closed circular plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. A vector system may comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. The vector may also include a selection marker such as an antibiotic resistance gene that can be used for selection of suitable transformants. Examples of such resistance genes are well known to those of skill in the art.

2. Antitoxic Agents 2.1. Extracts Containing Antitoxic Activity

An extract comprising an endogenous antitoxic agent has been isolated from the nonvenomous snake *Python reticulatus*. This antitoxic agent has a generic capacity to neutralise lethal doses of venoms and $PLA_2$ toxins, not only from a variety of different snakes, including those belonging to the major snake families Crotalidae, Elapidae and Viperidae, but also from other animals including insects and fish. It is believed that antitoxic factors with similar activities may be obtained from other *Python* species.

Accordingly, the invention broadly resides in an isolated extract of a *Python* species, which extract ameliorates conditions associated with envenomation and/or inflammation.

Suitably, the extract is characterised in that it neutralises or inhibits a venom or toxin. The venom or toxin preferably comprises as an active component a phospholipase, more preferably a phospholipase $A_2$.

Neutralisation or inhibition of a venom or toxin may be tested in vivo by administering a sample of the extract to an animal and challenging the animal with a dosage of the venom or toxin that invokes lethality or disease in the absence of the extract, wherein protection against lethality or disease is indicative of the extract comprising said neutralising or inhibiting activity.

The disease is preferably characterised by neurotoxic symptoms including, but not limited to, hind limb paralysis and impaired body movement. Alternatively, the disease is characterised by oedematogenic, myotoxic or cardiotoxic symptoms, haemostatic disturbance, haemolysis or hypotension.

A venom or toxin may be obtained from any suitable venom- or toxin-producing animal including, but not restricted to, snakes, insects and fish. In one embodiment, the venom or toxin is obtained from a Russell's viper species. Preferably, the venom or toxin is obtained from *Daboia russelli*, and more preferably *Daboia russelli siamensis*, *Daboia russelli russelli* or *Daboia russelli pulchella*. Preferably, the toxin is daboiatoxin, the principal lethal component of Russell's viper venom.

In an alternate embodiment, the venom is obtained from a bee or scorpion.

Alternatively, neutralisation or inhibition of a venom or toxin may be tested in vitro by contacting a preparation of brain cells or tissues, preferably brain synaptosomes, with the extract, contacting the said preparation with a venom-derived toxin, preferably a daboiatoxin, which toxin binds the cells or tissues in the absence of the extract, wherein inhibition of said binding is indicative of the extract comprising said neutralising or inhibiting activity.

The extract may be isolated from any suitable species of *Python*, including *P. reticulatus*, *P. molurus*, *P. regius*, *P. sabae*, and *P. timoriensis*. Preferably, the species is *P. reticulatus*.

The extract may be obtained from any suitable biological fluid or tissue of the said species. Preferably, the extract is obtained from serum of the said species.

Preferably, the extract comprises as an active component a polypeptide having a molecular mass of about 23-kDa. Suitably, the polypeptide self associates to form an oligomer of about 140-kDa.

2.2. Antitoxic Polypeptides

The invention also features an isolated polypeptide comprising the sequence set forth in SEQ ID NO: 6, which corresponds to a mature polypeptide with a subunit molecular mass of about 23-kDa obtained from *Python reticulatus*, as described more fully hereinafter.

In one embodiment, the isolated polypeptide may include a leader peptide comprising the sequence set forth in SEQ ID NO: 8 or biologically active fragment thereof, or variant or derivative of these. Accordingly, the invention also provides an isolated precursor polypeptide according to SEQ ID NO: 2, which comprises a leader peptide according to SEQ ID NO: 8 fused in frame with a polypeptide according to SEQ ID NO: 6.

2.3. Identification of Biologically Active Fragments

Biologically active fragments may be identified according to any suitable procedure known in the art. For example, a suitable method may include producing a fragment of a polypeptide according to any one of SEQ ID NO: 2 or 6, administering the fragment to an animal and challenging the animal with a dosage of a venom or toxin, which dosage in the absence of the fragment invokes lethality or disease in the animal, wherein protection against lethality or disease in the animal is indicative of the fragment being a biologically active fragment. "Protection" refers to a result better than 75% survival after 24 hours of administering a double LD50 dose of venom or toxin. The term "LD50 dose" is defined as the concentration of the dose of venom or toxin that causes death by 50% within 24 hours of its administration.

Alternatively, a suitable fragment may be tested for biological activity by contacting a preparation of brain cells or tissues, preferably brain synaptosomes, with the fragment, contacting the said preparation with a venom-derived toxin, preferably a daboiatoxin, which toxin binds the cells or tissues in the absence of the fragment, wherein inhibition of said binding is indicative of the fragment being a biologically active fragment.

2.4. Polypeptide Variants

The invention also contemplates polypeptide variants of the antitoxic polypeptide of the invention wherein said variants neutralise or inhibit a venom or toxin. Suitable methods of testing such activity are provided in Section 2.1. In general, variants will be at least 75% homologous, more suitably at least 80%, preferably at least 85%, and more preferably at least 90% homologous to a polypeptide as for example shown in SEQ ID NO: 2 or 6.

Suitable polypeptide variants may be identified by replacing at least one amino acid of a parent polypeptide (e.g., a polypeptide according to SEQ ID NO: 2 or 6) with a different amino acid to produce a modified polypeptide, combining the modified polypeptide with a phospholipase $A_2$; and detecting the presence of a conjugate comprising the modified polypeptide and the phospholipase $A_2$. If a conjugate is formed comprising the modified polypeptide and the phospholipase $A_2$, this is indicative of the modified polypeptide being a variant of the parent polypeptide.

Polypeptide variants may also be identified by administering a modified polypeptide as defined above to an animal and subsequently challenging the animal with a dosage of a venom or toxin, which dosage in the absence of the modified polypeptide invokes lethality or disease in the animal. If modified polypeptide protects against lethality or disease in the animal, this is indicative of the modified polypeptide being a polypeptide variant according to the invention.

Alternatively, suitable variants may be obtained by combining a modified polypeptide as defined above with an antigen-binding molecule that binds to a parent polypeptide or biological fragment on which the modified polypeptide is based, and preferably to a domain of the parent polypeptide or fragment that binds a phospholipase $A_2$ molecule. If a conjugate is formed comprising the modified polypeptide and the phospholipase $A_2$, this may be indicative of the modified polypeptide being a variant of the parent polypeptide or fragment.

2.5. Methods of Producing Polypeptide Variants 2.5.1. Mutagenesis

Polypeptide variants according to the invention can be identified either rationally, or via established methods of mutagenesis (see, for example, Watson, J. D. et al., "MOLECULAR BIOLOGY OF THE GENE", Fourth Edition, Benjamin/Cummings, Menlo Park, Calif., 1987). Significantly, a random mutagenesis approach requires no a priori information about the gene sequence that is to be mutated. This approach has the advantage that it assesses the desirability of a particular mutant based on its function, and thus does not require an understanding of how or why the resultant mutant protein has adopted a particular conformation. Indeed, the random mutation of target gene sequences has been one approach used to obtain mutant proteins having desired characteristics (Leatherbarrow, R. 1986, *J. Prot. Eng.* 1: 7–16; Knowles, J. R., 1987, *Science* 236: 1252–1258; Shaw, W. V., 1987, *Biochem. J.* 246: 1–17; Gerit, J. A. 1987, *Chem. Rev.* 87: 1079–1105). Alternatively, where a particular sequence alteration is desired, methods of site-directed mutagenesis can be employed. Thus, such methods may be used to selectively alter only those amino acids of the protein that are believed to be important (Craik, C. S., 1985, *Science* 228: 291–297; Cronin, et al., 1988, *Biochem.* 27: 4572–4579; Wilks, et al., 1988, *Science* 242: 1541–1544).

Variant peptides or polypeptides, resulting from rational or established methods of mutagenesis or from combinatorial chemistries as hereinafter described, may comprise conservative amino acid substitutions. Exemplary conservative substitutions in an immuno-interactive polypeptide or polypeptide fragment according to the invention may be made according to the following TABLE A:

| Original Residue | Exemplary Substitutions |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile, |
| Phe | Met, Leu, Tyr |
| Ser | Thr |
| Thr | Ser |
| Trp | Tyr |
| Tyr | Trp, Phe |
| Val | Ile, Leu |

Substantial changes in function are made by selecting substitutions that are less conservative than those shown in TABLE A. Other replacements would be non-conservative substitutions and relatively fewer of these may be tolerated. Generally, the substitutions which are likely to produce the greatest changes in a polypeptide's properties are those in which (a) a hydrophilic residue (eg, Ser or Thr) is substituted for, or by, a hydrophobic residue (eg, Ala, Leu, Ile, Phe or Val); (b) a cysteine or proline is substituted for, or by, any other residue; (c) a residue having an electropositive side chain (eg, Arg, His or Lys) is substituted for, or by, an electronegative residue (eg, Glu or Asp) or (d) a residue having a bulky side chain (eg, Phe or Trp) is substituted for, or by, one having a smaller side chain (eg, Ala, Ser)or no side chain (eg, Gly).

What constitutes suitable variants may be determined by conventional techniques. For example, nucleic acids encoding a polypeptide according to SEQ ID NO: 2 or 6 can be mutated using either random mutagenesis for example using transposon mutagenesis, or site-directed mutagenesis as described, for example, in Section 3.2 infra.

2.5.2. Peptide Libraries Produced by Combinatorial Chemistry

A number of facile combinatorial technologies can be utilised to synthesise molecular libraries of immense diversity. In the present case, variants of a polypeptide, or preferably a polypeptide fragment according to the invention, can be synthesised using such technologies. Variants can be screened subsequently using the methods described in Section 2.4.

Preferably, soluble synthetic peptide combinatorial libraries (SPCLs) are produced which offer the advantage of working with free peptides in solution, thus permitting adjustment of peptide concentration to accommodate a particular assay system. SPCLs are suitably prepared as hexamers. In this regard, a majority of binding sites is known to involve four to six residues. Cysteine is preferably excluded from the mixture positions to avoid the formation of disulfides and more difficult-to-define polymers. Exemplary methods of producing SPCLs are disclosed by Houghten et al. (1991, *Nature* 354: 84–86; 1992, *BioTechniques* 13: 412–421), Appel et al. (1992, *Immunomethods* 1: 17–23), and Pinilla et al. (1992, *BioTechniques* 13: 901–905; 1993, *Gene* 128: 71–76).

Preparation of combinatorial synthetic peptide libraries may employ either t-butyloxycarbonyl (t-Boc) or 9-fluorenylmethyloxycarbonyl (Fmoc) chemistries (see Chapter 9.1, of Coligan et al., supra; Stewart and Young, 1984, Solid Phase Peptide Synthesis, 2nd ed. Pierce Chemical Co., Rockford, Ill.; and Atherton and Sheppard, 1989, Solid Phase Peptide Synthesis: A Practical Approach. IRL Press, Oxford) preferably, but not exclusively, using one of two different approaches. The first of these approaches, suitably termed the "split-process-recombine" or "split synthesis" method, was described first by Furka et al. (1988, *14th Int. Congr. Biochem.*, Prague, Czechoslovakia 5: 47; 1991, *Int. J. Pept. Protein Res.* 37: 487–493) and Lam et al. (1991, *Nature* 354: 82–84), and reviewed later by Eichler et al. (1995, *Medicinal Research Reviews* 15(6): 481–496) and Balkenhohl et al. (1996, *Angew. Chem. Int. Ed. Engl.* 35: 2288–2337). Briefly, the split synthesis method involves dividing a plurality of solid supports such as polymer beads into n equal fractions representative of the number of available amino acids for each step of the synthesis (e.g., 20 L-amino acids), coupling a single respective amino acid to each polymer bead of a corresponding fraction, and then thoroughly mixing the polymer beads of all the fractions together. This process is repeated for a total of x cycles to produce a stochastic collection of up to $N^x$ different compounds. The peptide library so produced may be screened for example with a suitably labelled phospholipase $A_2$. Upon detection, some of the positive beads are selected for sequencing to identify the active peptide. Such peptide may be subsequently cleaved from the beads, and assayed using the same phospholipase $A_2$ to identify the most active peptide sequence.

The second approach, the chemical ratio method, prepares mixed peptide resins using a specific ratio of amino acids empirically defined to give equimolar incorporation of each amino acid at each coupling step. Each resin bead contains a mixture of peptides. Approximate equimolar representation can be confirmed by amino acid analysis (Dooley and Houghten, 1993, *Proc. Natl. Acad. Sci. U.S.A.* 90: 10811–10815; Eichler and Houghten, 1993, *Biochemistry* 32: 11035–11041). Preferably, the synthetic peptide library is produced on polyethylene rods, or pins, as a solid support, as for example disclosed by Geysen et al. (1986, *Mol. Immunol.* 23: 709–715). An exemplary peptide library of this type may consist of octapeptides in which the third and fourth position are defined with each of the 20 amino acids, whereas the remaining six positions are present as mixtures. This peptide library can be represented by the formula Ac-XXO$_1$O$_2$XXXX-S$_s$, where S$_s$ is the solid support. Peptide mixtures remain on the pins when assayed against a soluble receptor molecule. For example, the peptide library of Geysen (1986, *Immun. Today* 364–369; and Geysen et al., Ibid), comprising for example dipeptides, is first screened for the ability to bind to a target molecule. The most active dipeptides are then selected for an additional round of testing comprising linking, to the starting dipeptide, an additional residue (or by internally modifying the components of the original starting dipeptide) and then screening this set of candidates for the desired activity. This process is reiterated until the binding partner having the desired properties is identified.

2.5.3. Alanine Scanning Mutagenesis

In one embodiment, the invention herein utilises a systematic analysis of an a polypeptide or polypeptide fragment according to the invention to determine the residues in the polypeptide or fragment that are involved in the interaction with phospholipase $A_2$. Such analysis is conveniently performed using recombinant DNA technology. In general, a DNA sequence encoding the polypeptide or fragment is cloned and manipulated so that it may be expressed in a convenient host. DNA encoding the polypeptide or fragment can be obtained from a genomic library, from cDNA derived from mRNA in cells expressing the said polypeptide or fragment, or by synthetically constructing the DNA sequence (Sambrook et al., supra; Ausubel et al., supra).

The wild-type DNA encoding the polypeptide or fragment is then inserted into an appropriate plasmid or vector as described herein. In particular, prokaryotes are preferred for cloning and expressing DNA sequences to produce variants of the polypeptide or fragment. For example, *E. coli* K12 strain 294 (ATCC No. 31446) may be used, as well as *E. coli* B, *E. coli* X1776 (ATCC No. 31537), and *E. coli* c600 and c600hfl, and *E. coli* W3110 ($F^-$, $\gamma^-$, prototrophic, ATCC No. 27325), bacilli such as *Bacillus subtilis*, and other enterobacteriaceae such as *Salmonella typhimurium* or *Serratia marcescens*, and various *Pseudomonas* species. A preferred prokaryote is *E. coli* W3110 (ATCC 27325).

Once the polypeptide or fragment is cloned, site-specific mutagenesis as for example described by Carter et al. (1986, *Nucl. Acids. Res.*, 13: 4331) or by Zoller et al. (1987, *Nucl. Acids Res.*, 10: 6487), cassette mutagenesis as for example described by Wells et al. (1985, *Gene*, 34: 315), restriction selection mutagenesis as for example described by Wells et al. (1986, *Philos. Trans. R. Soc. London SerA*, 317: 415), or other known techniques may be performed on the cloned DNA to produce the variant DNA that encodes for the changes in amino acid sequence defined by the residues being substituted. When operably linked to an appropriate expression vector, variants are obtained. In some cases, recovery of the variant may be facilitated by expressing and secreting such molecules from the expression host by use of an appropriate signal sequence operably linked to the DNA sequence encoding the variant. Such methods are well known to those skilled in the art. Of course, other methods may be employed to produce such polypeptides or fragments such as the in vitro chemical synthesis of the desired polypeptide variant (Barany et al. In *The Peptides*, eds. E. Gross and J. Meienhofer (Academic Press: N.Y. 1979), Vol. 2, pp. 3–254).

Once the different variants are produced, they are contacted with a phospholipase $A_2$ and the interaction, if any, between phospholipase $A_2$ and each variant is determined. These activities are compared to the activity of the parent polypeptide or fragment with the same phospholipase $A_2$ molecule to determine which of the amino acid residues in the active domain are involved in the interaction with the phospholipase $A_2$. The scanning amino acid used in such an analysis may be any different amino acid from that substituted, i.e., any of the 19 other naturally occurring amino acids.

The interaction between the phospholipase $A_2$, and parent and variant, respectively, can be measured by any convenient assay as for example described herein. While any number of analytical measurements may be used to compare activities, a convenient one for binding of phospholipase $A_2$ is the dissociation constant $K_d$ of the complex formed between the variant and phospholipase $A_2$ as compared to the $K_d$ for the parent polypeptide or fragment. Generally, a two-fold increase or decrease in $K_d$ per analogous residue substituted by the substitution indicates that the substituted residue(s) is active in the interaction of the parent polypeptide or fragment with the target phospholipase $A_2$.

When a suspected or known active amino acid residue is subjected to scanning amino acid analysis, the amino acid residues immediately adjacent thereto should be scanned. Three residue-substituted polypeptides can be made. One contains a scanning amino acid, preferably alanine, at position N that is the suspected or known active amino acid. The two others contain the scanning amino acid at position N+1 and N−1. If each substituted polypeptide or fragment causes a greater than about two-fold effect on $K_d$ for the receptor, the scanning amino acid is substituted at position N+2 and N−2. This is repeated until at least one, and preferably four, residues are identified in each direction which have less than about a two-fold effect on $K_d$ or either of the ends of the parent polypeptide or fragment are reached. In this manner, one or more amino acids along a continuous amino acid sequence that are involved in the interaction with the particular phospholipase $A_2$ molecule can be identified.

The active amino acid residue identified by amino acid scan is typically one that contacts the phospholipase $A_2$ directly. However, active amino acids may also indirectly contact the phospholipase $A_2$ through salt bridges formed with other residues or small molecules such as $H_2O$ or ionic species such as $Na^+$, $Ca^{+2}$, $Mg^{+2}$, or $Zn^{+2}$.

In some cases, the substitution of a scanning amino acid at one or more residues results in a residue-substituted polypeptide which is not expressed at levels that allow for the isolation of quantities sufficient to carry out analysis of its activity with the phospholipase $A_2$. In such cases, a different scanning amino acid, preferably an isosteric amino acid, can be used.

Among the preferred scanning amino acids are relatively small, neutral amino acids. Such amino acids include alanine, glycine, serine, and cysteine. Alanine is the preferred scanning amino acid among this group because it eliminates the side-chain beyond the beta-carbon and is less likely to alter the main-chain conformation of the variant. Alanine is also preferred because it is the most common amino acid. Further, it is frequently found in both buried and exposed positions (Creighton, *The Proteins*, W. H. Freeman & Co., N.Y.; Chothia, 1976, *J. Mol. Biol.,* 150: 1). If alanine substitution does not yield adequate amounts of variant, an isosteric amino acid can be used. Alternatively, the following amino acids in decreasing order of preference may be used: Ser, Asn, and Leu.

Once the active amino acid residues are identified, isosteric amino acids may be substituted. Such isosteric substitutions need not occur in all instances and may be performed before any active amino acid is identified. Such isosteric amino acid substitution is performed to minimise the potential disruptive effects on conformation that some substitutions can cause. Isosteric amino acids are shown in TABLE B below:

The method herein can be used to detect active amino acid residues within different domains of a polypeptide or fragment according to the invention. Once this identification is made, various modifications to the parent polypeptide or fragment may be made to modify the interaction between the parent polypeptide or fragment and phospholipase $A_2$.

| Polypeptide Amino Acid | Isosteric Scanning Amino Acid |
|---|---|
| Ala (A) | Ser, Gly |
| Glu (E) | Gln, Asp |
| Gln (Q) | Asn, Glu |
| Asp (D) | Asn, Glu |
| Asn (N) | Ala, Asp |
| Leu (L) | Met, Ile |
| Gly (G) | Pro, Ala |
| Lys (K) | Met, Arg |
| Ser (S) | Thr, Ala |
| Val (V) | Ile, Thr |
| Arg (R) | Lys, Met, Asn |
| Thr (T) | Ser, Val |
| Pro (P) | Gly |
| Ile (I) | Met, Leu, Val |
| Met (M) | Ile, Leu |
| Phe (F) | Tyr |
| Tyr (Y) | Phe |
| Cys (C) | Ser, Ala |
| Trp (W) | Phe |
| His (H) | Asn, Gln |

2.5.4. Polypeptide or Peptide Libraries Produced by Phage Display

The identification of variants can also be facilitated through the use of a phage (or phagemid) display protein ligand screening system as for example described by Lowman, et al. (1991, *Biochem.* 30: 10832–10838), Markland, et al. (1991, *Gene* 109: 13–19), Roberts, et al. (1992, *Proc. Natl. Acad. Sci.* (U.S.A.) 89: 2429–2433), Smith, G. P. (1985, *Science* 228: 1315–1317), Smith, et al. (1990, *Science* 248: 1126–1128) and Lardner et al. (U.S. Pat. No. 5,223,409). In general, this method involves expressing a fusion protein in which the desired protein ligand is fused to the N-terminus of a viral coat protein (such as the M13 Gene III coat protein, or a lambda coat protein).

In one embodiment, a library of phage is engineered to display novel peptides within the phage coat protein sequences. Novel peptide sequences are generated by random mutagenesis of gene fragments encoding an antitoxic polypeptide or biologically active fragment using error-prone PCR, or by in vivo mutation by *E. coli* mutator cells. The novel peptides displayed on the surface of the phage are placed in contact, with a phospholipase $A_2$ molecule. Phage that display coat protein having peptides that are capable of binding to phospholipase $A_2$ are immobilised by such treatment, whereas all other phage can be washed away. After the removal of unbound phage, the bound phage can be amplified, and the DNA encoding their coat proteins can be sequenced. In this manner, the amino acid sequence of the embedded peptide or polypeptide can be deduced.

In more detail, the method involves (a) constructing a replicable expression vector comprising a first gene encoding a polypeptide or fragment of the invention, a second gene encoding at least a portion of a natural or wild-type phage coat protein wherein the first and second genes are heterologous, and a transcription regulatory element operably linked to the first and second genes, thereby forming a gene fusion encoding a fusion protein; (b) mutating the vector at one or more selected positions within the first gene thereby forming a family of related plasmids; (c) transforming suitable host cells with the plasmids; (d) infecting the transformed host cells with a helper phage having a gene encoding the phage coat protein; (e) culturing the transformed infected host cells under conditions suitable for forming recombinant phagemid particles containing at least a portion of the plasmid and capable of transforming the host, the conditions adjusted so that no more than a minor amount of phagemid particles display more than one copy of the fusion protein on the surface of the particle; (f) contacting the phagemid particles with a phospholipase $A_2$ molecule that binds to the parent polypeptide or fragment so that at least a portion of the phagemid particles bind to the phospholipase $A_2$; and (g) separating the phagemid particles that bind from those that do not. Preferably, the method further comprises transforming suitable host cells with recombinant phagemid particles that bind to the phospholipase $A_2$ molecule and repeating steps (d) through (g) one or more times.

Preferably in this method the plasmid is under tight control of the transcription regulatory element, and the culturing conditions are adjusted so that the amount or number of phagemid particles displaying more than one copy of the fusion protein on the surface of the particle is less than about 1%. Also, preferably, the amount of phagemid particles displaying more than one copy of the fusion protein is less than 10% of the amount of phagemid particles displaying a single copy of the fusion protein. Most preferably, the amount is less than 20%.

Typically in this method, the expression vector will further contain a secretory signal sequence fused to the DNA encoding each subunit of the polypeptide and the transcription regulatory element will be a promoter system. Preferred promoter systems are selected from lac Z, $\lambda_{PL}$, tac, T7 polymerase, tryptophan, and alkaline phosphatase promoters and combinations thereof. Also, normally the method will employ a helper phage selected from M13K07, M13R408, M13-VCS, and Phi X 174. The preferred helper phage is M13K07, and the preferred coat protein is the M13 Phage gene III coat protein. The preferred host is *E. coli*, and protease-deficient strains of *E. coli*.

Repeated cycles of variant selection are used to select for higher and higher affinity binding by the phagemid selection of multiple amino acid changes that are selected by multiple selection cycles. Following a first round of phagemid selection, involving a first region or selection of amino acids in the ligand polypeptide, additional rounds of phagemid selection in other regions or amino acids of the ligand polypeptide are conducted. The cycles of phagemid selection are repeated until the desired affinity properties of the ligand polypeptide are achieved.

It will be appreciated that the amino acid residues that form the binding domain of the polypeptide or fragment may not be sequentially linked and may reside on different subunits of the polypeptide or fragment. That is, the binding domain tracks with the particular secondary structure at the binding site and not the primary structure. Thus, generally, mutations will be introduced into codons encoding amino acids within a particular secondary structure at sites directed away from the interior of the polypeptide so that they will have the potential to interact with the phospholipase $A_2$.

The phagemid-display method herein contemplates fusing a polynucleotide encoding the polypeptide or fragment (polynucleotide 1) to a second polynucleotide (polynucleotide 2) such that a fusion protein is generated during transcription. Polynucleotide 2 is typically a coat protein gene of a phage, and preferably it is the phage M13 gene III coat protein, or a fragment thereof. Fusion of polynucleotides 1 and 2 may be accomplished by inserting polynucleotide 2 into a particular site on a plasmid that contains polynucleotide 1, or by inserting polynucleotide 1 into a particular site on a plasmid that contains polynucleotide 2.

Between polynucleotide 1 and polynucleotide 2, DNA encoding a termination codon may be inserted, such termination codons being UAG (amber), UAA (ocher), and UGA (opel) (see for example, Davis et al., *Microbiology* (Harper and Row: New York, 1980), pages 237, 245–247, and 274). The termination codon expressed in a wild-type host cell results in the synthesis of the polynucleotide 1 protein product without the polynucleotide 2 protein attached. However, growth in a suppressor host cell results in the synthesis of detectable quantities of fused protein. Such suppressor host cells contain a tRNA modified to insert an amino acid in the termination codon position of the mRNA, thereby resulting in production of detectable amounts of the fusion protein. Suppressor host cells of this type are well known and described, such as *E. coli* suppressor strain (Bullock et al., 1987, *BioTechniques*, 5: 376–379). Any acceptable method may be used to place such a termination codon into the mRNA encoding the fusion polypeptide.

The suppressible codon may be inserted between the polynucleotide encoding the polypeptide or fragment and a second polynucleotide encoding at least a portion of a phage coat protein. Alternatively, the suppressible termination codon may be inserted adjacent to the fusion site by replacing the last amino acid triplet in the polypeptide/fragment or the first amino acid in the phage coat protein. When the phagemid containing the suppressible codon is grown in a suppressor host cell, it results in the detectable production of a fusion polypeptide containing the polypeptide or fragment and the coat protein. When the phagemid is grown in a non-suppressor host cell, the polypeptide or fragment is synthesised substantially without fusion to the phage coat protein due to termination at the inserted suppressible triplet encoding UAG, UAA, or UGA. In the non-suppressor cell the polypeptide is synthesised and secreted from the host cell due to the absence of the fused phage coat protein which otherwise anchored it to the host cell.

The polypeptide or fragment may be altered at one or more selected codons. An alteration is defined as a substitution, deletion, or insertion of one or more codons in the gene encoding the polypeptide or fragment that results in a change in the amino acid sequence as compared with the unaltered or native sequence of the said polypeptide or fragment. Preferably, the alterations will be by substitution of at least one amino acid with any other amino acid in one or more regions of the molecule. The alterations may be produced by a variety of methods known in the art. These methods include, but are not limited to, oligonucleotide-mediated mutagenesis and cassette mutagenesis as described for example herein.

For preparing the phospholipase $A_2$ molecule and binding it with the phagemid, the phospholipase $A_2$ molecule is attached to a suitable matrix such as agarose beads, acrylamide beads, glass beads, cellulose, various acrylic copolymers, hydroxyalkyl methacrylate gels, polyacrylic acid, polymethacrylic copolymers, nylon, neutral and ionic carriers, and the like. Attachment of the phospholipase $A_2$ molecule to the matrix may be accomplished by methods described in *Methods Enzymol.*, 44: (1976), or by other means known in the art.

After attachment of the phospholipase $A_2$ molecule to the matrix, the immobilised phospholipase $A_2$ is contacted with the library of phagemid particles under conditions suitable for binding of at least a portion of the phagemid particles with the immobilised phospholipase $A_2$ or target. Normally, the conditions, including pH, ionic strength, temperature, and the like will mimic physiological conditions.

Bound phagemid particles ("binders") having high affinity for the immobilised target are separated from those having a low affinity (and thus do not bind to the target) by washing. Binders may be dissociated from the immobilised target by a variety of methods. These methods include competitive dissociation using the wild-type ligand, altering pH and/or ionic strength, and methods known in the art.

Suitable host cells are infected with the binders and helper phage, and the host cells are cultured under conditions suitable for amplification of the phagemid particles. The phagemid particles are then collected and the selection process is repeated one or more times until binders having the desired affinity for the target molecule are selected.

2.5.5. Rational Drug Design

Variants of naturally occurring antitoxic polypeptides or polypeptide fragments according to the invention may also be obtained using the principles of conventional or of rational drug design as for example described by Andrews, et al. (In: "PROCEEDINGS OF THE ALFRED BENZON SYMPOSIUM", volume 28, pp. 145–165, Munksgaard, Copenhagen, 1990), McPherson, A. (1990, *Eur. J. Biochem.* 189: 1–24), Hol, et al. (In: "MOLECULAR RECOGNITION: CHEMICAL AND BIOCHEMICAL PROBLEMS", Roberts, S. M. (ed.); Royal Society of Chemistry; pp. 84–93, 1989), Hol, W. G. J. (1989, *Arzneim-Forsch.* 39: 1016–1018), Hol, W. G. J. (1986, *Agnew Chem. Int. Ed. Engl.* 25: 767–778).

In accordance with the methods of conventional drug design, the desired variant molecules are obtained by randomly testing molecules whose structures have an attribute in common with the structure of a "native" antitoxic polypeptide or biologically active fragment according to the invention. The quantitative contribution that results from a change in a particular group of a binding molecule can be determined by measuring the capacity of competition or cooperativity between the native polypeptide or polypeptide fragment and the candidate polypeptide variant.

In one embodiment of rational drug design, the polypeptide variant is designed to share an attribute of the most stable three-dimensional conformation of a polypeptide or polypeptide fragment according to the invention. Thus, the variant may be designed to possess chemical groups that are oriented in a way sufficient to cause ionic, hydrophobic, or van der Waals interactions that are similar to those exhibited by the immuno-interactive polypeptide or polypeptide fragment. In a second method of rational design, the capacity of a particular polypeptide or polypeptide fragment to undergo conformational "breathing" is exploited. Such "breathing"—the transient and reversible assumption of a different molecular conformation—is a well-appreciated phenomenon, and results from temperature, thermodynamic factors, and from the catalytic activity of the molecule. Knowledge of the 3-dimensional structure of the polypeptide or polypeptide fragment facilitates such an evaluation. An evaluation of the natural conformational changes of a polypeptide or polypeptide fragment facilitates the recognition of potential hinge sites, potential sites at which hydrogen bonding, ionic bonds or van der Waals bonds might form or might be eliminated due to the breathing of the molecule, etc. Such recognition permits the identification of the additional conformations that the polypeptide or polypeptide fragment could assume, and enables the rational design and production of mimetic polypeptide variants that share such conformations.

The preferred method for performing rational mimetic design employs a computer system capable of forming a representation of the three-dimensional structure of the polypeptide or polypeptide fragment (such as those obtained using RIBBON (Priestle, J., 1988, *J. Mol. Graphics* 21: 572), QUANTA (Polygen), InSite (Biosyn), or Nanovision (American Chemical Society)). Such analyses are exemplified by Hol, et al. (In: "MOLECULAR RECOGNITION: CHEMICAL AND BIOCHEMICAL PROBLEMS", supra, Hol, W. G. J. (1989, supra) and Hol, W. G. J., (1986, supra).

In lieu of such direct comparative evaluations of candidate polypeptide variants, screening assays may be used to identify such molecules. Such assays will preferably exploit the capacity of the variant to bind to phospholipase $A_2$ molecule as described in Section 2.4.

2.6. Polypeptide Derivatives

With reference to suitable derivatives of the invention, such derivatives include amino acid deletions and/or additions to a polypeptide, fragment or variant of the invention, wherein said derivatives neutralise or inhibit a venom or toxin. "Additions" of amino acids may include fusion of the polypeptides, fragments and polypeptide variants of the invention with other polypeptides or proteins. For example, it will be appreciated that said polypeptides, fragments or variants may be incorporated into larger polypeptides, and that such larger polypeptides may also be expected to neutralise or inhibit a venom or toxin.

The polypeptides, fragments or variants of the invention may be fused to a further protein, for example, which is not derived from the original host. The further protein may assist in the purification of the fusion protein. For instance, a polyhistidine tag or a maltose binding protein may be used in this respect as described in more detail below. Other possible fusion proteins are those which produce an immunomodulatory response. Particular examples of such proteins include Protein A or glutathione S-transferase (GST).

Other derivatives contemplated by the invention include, but are not limited to, modification to side chains, incorporation of unnatural amino acids and/or their derivatives during peptide, polypeptide or protein synthesis and the use of crosslinkers and other methods which impose conformational constraints on the polypeptides, fragments and variants of the invention.

Examples of side chain modifications contemplated by the present invention include modifications of amino groups such as by acylation with acetic anhydride; acylation of amino groups with succinic anhydride and tetrahydrophthalic anhydride; amidination with methylacetimidate; carbamoylation of amino groups with cyanate; pyridoxylation of lysine with pyridoxal-5-phosphate followed by reduction with $NaBH_4$; reductive alkylation by reaction with an aldehyde followed by reduction with $NaBH_4$; and trinitrobenzylation of amino groups with 2,4,6-trinitrobenzene sulphonic acid (TNBS).

The carboxyl group may be modified by carbodiimide activation via O-acylisourea formation followed by subsequent derivitisation, by way of example, to a corresponding amide.

The guanidine group of arginine residues may be modified by formation of heterocyclic condensation products with reagents such as 2,3-butanedione, phenylglyoxal and glyoxal.

Sulphydryl groups may be modified by methods such as performic acid oxidation to cysteic acid; formation of mercurial derivatives using 4-chloromercuriphenylsulphonic acid, 4-chloromercuribenzoate; 2-chloromercuri-4-nitrophenol, phenylmercury chloride, and other mercurials; formation of a mixed disulphides with other thiol compounds; reaction with maleimide, maleic anhydride or other substituted maleimide; carboxymethylation with iodoacetic acid or iodoacetamide; and carbamoylation with cyanate at alkaline pH.

Tryptophan residues may be modified, for example, by alkylation of the indole ring with 2-hydroxy-5-nitrobenzyl bromide or sulphonyl halides or by oxidation with N-bromosuccinimide.

Tyrosine residues may be modified by nitration with tetranitromethane to form a 3-nitrotyrosine derivative.

The imidazole ring of a histidine residue may be modified by N-carbethoxylation with diethylpyrocarbonate or by alkylation with iodoacetic acid derivatives.

Examples of incorporating unnatural amino acids and derivatives during peptide synthesis include but are not limited to, use of 4-amino butyric acid, 6-aminohexanoic acid, 4-amino-3-hydroxy-5-phenylpentanoic acid, 4-amino-3-hydroxy-6-methylheptanoic acid, t-butylglycine, norleucine, norvaline, phenylglycine, ornithine, sarcosine, 2-thienyl alanine and/or D-isomers of amino acids. A list of unnatural amino acids contemplated by the present invention is shown in TABLE C:

| Non-conventional amino acid | Non-conventional amino acid |
|---|---|
| α-aminobutyric acid | L-N-methylalanine |
| α-amino-α-methylbutyrate | L-N-methylarginine |
| aminocyclopropane-carboxylate | L-N-methylasparagine |
| aminoisobutyric acid | L-N-methylaspartic acid |
| aminonorbornyl-carboxylate | L-N-methylcysteine |
| cyclohexylalanine | L-N-methylglutamine |
| cyclopentylalanine | L-N-methylglutamic acid |
| L-N-methylisoleucine | L-N-methylhistidine |
| D-alanine | L-N-methylleucine |
| D-arginine | L-N-methyllysine |
| D-aspartic acid | L-N-methylmethionine |
| D-cysteine | L-N-methylnorleucine |
| D-glutamate | L-N-methylnorvaline |
| D-glutamic acid | L-N-methylornithine |
| D-histidine | L-N-methylphenylalanine |
| D-isoleucine | L-N-methylproline |
| D-leucine | L-N-medlylserine |
| D-lysine | L-N-methylthreonine |
| D-methionine | L-N-methyltryptophan |
| D-ornithine | L-N-methyltyrosine |
| D-phenylalanine | L-N-methylvaline |
| D-proline | L-N-methylethylglycine |
| D-serine | L-N-methyl-t-butylglycine |
| D-threonine | L-norleucine |
| D-tryptophan | L-norvaline |
| D-tyrosine | α-methyl-aminoisobutyrate |
| D-valine | α-methyl-γ-aminobutyrate |
| D-α-methylalanine | α-methylcyclohexylalanine |
| D-α-methylarginine | α-methylcylcopentylalanine |
| D-α-methylasparagine | α-methyl-α-napthylalanine |
| D-α-methylaspartate | α-methylpenicillamine |
| D-α-methylcysteine | N-(4-aminobutyl)glycine |
| D-α-methylglutamine | N-(2-aminoethyl)glycine |
| D-α-methylhistidine | N-(3-aminopropyl)glycine |
| D-α-methylisoleucine | N-amino-α-methylbutyrate |
| D-α-methylleucine | α-napthylalanine |
| D-α-methyllysine | N-benzylglycine |
| D-α-methylmethionine | N-(2-carbamylediyl)glycine |
| D-α-methylornithiine | N-(carbamylmethyl)glycine |
| D-α-methylphenylalanine | N-(2-carboxyethyl)glycine |
| D-α-methylproline | N-(carboxymethyl)glycine |
| D-α-methylserine | N-cyclobutylglycine |

-continued

| Non-conventional amino acid | Non-conventional amino acid |
|---|---|
| D-α-methylthreonine | N-cycloheptylglycine |
| D-α-methyltryptophan | N-cyclohexylglycine |
| D-α-methyltyrosine | N-cyclodecylglycine |
| L-α-methylleucine | L-α-methyllysine |
| L-α-methylmethionine | L-α-methylnorleucine |
| L-α-methylnorvatine | L-α-methylornithine |
| L-α-methylphenylalanine | L-α-methylproline |
| L-α-methylserine | L-α-methylthreonine |
| L-α-methyltryptophan | L-α-methyltyrosine |
| L-α-methylvaline | L-N-methylhomophenylalanine |
| N-N-(2,2-diphenylethyl carbamylmethyl) glycine | N-N-(3,3-diphenylpropyl carbamylmethyl) glycine |
| 1-carboxy-1-(2,2-diphenyl-ethyl amino) cyclopropane | |

Also contemplated is the use of crosslinkers, for example, to stabilise 3D conformations of the polypeptides, fragments or variants of the invention, using homo-bifunctional cross linkers such as bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety or carbodiimide. In addition, peptides can be conformationally constrained, for example, by introduction of double bonds between $C_\alpha$ and $C_\beta$ atoms of amino acids, by incorporation of $C_\alpha$ and $N_\alpha$-methylamino acids, and by formation of cyclic peptides or analogues by introducing covalent bonds such as forming an amide bond between the N and C termini between two side chains or between a side chain and the N or C terminus of the peptides or analogues. For example, reference may be made to: Marlowe (1993, *Biorganic & Medicinal Chemistry Letters* 3: 437–44) who describes peptide cyclisation on TFA resin using trimethylsilyl (TMSE) ester as an orthogonal protecting group; Pallin and Tam (1995, *J. Chem. Soc. Chem. Comm.* 2021–2022) who describe the cyclisation of unprotected peptides in aqueous solution by oxime formation; Algin et al (1994, *Tetrahedron Letters* 35: 9633–9636) who disclose solid-phase synthesis of head-to-tail cyclic peptides via lysine side-chain anchoring; Kates et al (1993, *Tetrahedron Letters* 34: 1549–1552) who describe the production of head-to-tail cyclic peptides by three-dimensional solid phase strategy; Tumelty et al (1994, *J. Chem. Soc. Chem. Comm.* 1067–1068) who describe the synthesis of cyclic peptides from an immobilised activated intermediate, wherein activation of the immobilised peptide is carried out with N-protecting group intact and subsequent removal leading to cyclisation; McMurray et al (1994, *Peptide Research* 7: 195–206) who disclose head-to-tail cyclisation of peptides attached to insoluble supports by means of the side chains of aspartic and glutamic acid; Hruby et al (1994, *Reactive Polymers* 22: 231–241) who teach an alternate method for cyclising peptides via solid supports; and Schmidt and Langer (1997, *J. Peptide Res.* 49: 67–73) who disclose a method for synthesising cyclotetrapeptides and cyclopentapeptides. The foregoing methods may be used to produce conformationally constrained polypeptides that neutralise or inhibit a venom or toxin.

The invention also contemplates polypeptides, fragments or variants of the invention that have been modified using ordinary molecular biological techniques so as to improve their resistance to proteolytic degradation or to optimise their solubility properties or to render them more suitable as an immunogenic agent.

2.7. Methods of Preparing the Polypeptides of the Invention

Polypeptides of the inventions may be prepared by any suitable procedure known to those of skill in the art. For example, the polypeptides may be prepared by a procedure including the steps of:

(a) preparing a recombinant polynucleotide comprising a nucleotide sequence encoding a polypeptide comprising the sequence set forth in SEQ ID NO: 2 or 6, or variant or derivative of these, which nucleotide sequence is operably linked to transcriptional and translational regulatory nucleic acid;

(b) introducing the recombinant polynucleotide into a suitable host cell;

(c) culturing the host cell to express recombinant polypeptide from said recombinant polynucleotide; and (d) isolating the recombinant polypeptide.

Suitably, said nucleotide sequence comprises the sequence set forth in any one of SEQ ID NO: 1 or 5.

The recombinant polynucleotide preferably comprises either an expression vector that may be a self-replicating extra-chromosomal vector such as a plasmid, or a vector that integrates into a host genome.

The transcriptional and translational regulatory nucleic acid will generally be appropriate for the host cell used for expression. Numerous types of appropriate expression vectors and suitable regulatory sequences are known in the art for a variety of host cells.

Typically, the transcriptional and translational regulatory nucleic acid may include, but is not limited to, promoter sequences, leader or signal sequences, ribosomal binding sites, transcriptional start and stop sequences, translational start and termination sequences, and enhancer or activator sequences.

Constitutive or inducible promoters as known in the art are contemplated by the invention. The promoters may be either naturally occurring promoters, or hybrid promoters that combine elements of more than one promoter.

In a preferred embodiment, the expression vector contains a selectable marker gene to allow the selection of transformed host cells. Selection genes are well known in the art and will vary with the host cell used.

The expression vector may also include a fusion partner (typically provided by the expression vector) so that the recombinant polypeptide of the invention is expressed as a fusion polypeptide with said fusion partner. The main advantage of fusion partners is that they assist identification and/or purification of said fusion polypeptide.

In order to express said fusion polypeptide, it is necessary to ligate a polynucleotide according to the invention into the expression vector so that the translational reading frames of the fusion partner and the polynucleotide coincide.

Well known examples of fusion partners include, but are not limited to, glutathione-S-transferase (GST), Fc potion of human IgG, maltose binding protein (MBP) and hexahistidine (HIS$_6$), which are particularly useful for isolation of the fusion polypeptide by affinity chromatography. For the purposes of fusion polypeptide purification by affinity chromatography, relevant matrices for affinity chromatography are glutathione-, amylose-, and nickel- or cobalt-conjugated resins respectively. Many such matrices are available in "kit" form, such as the QIAexpress™ system (Qiagen) useful with (HIS$_6$) fusion partners and the Pharmacia GST purification system. In a preferred embodiment, the recombinant polynucleotide is expressed in the commercial vector QIAexpress™ pQE-30 as described more fully hereinafter.

Another fusion partner well known in the art is green fluorescent protein (GFP). This fusion partner serves as a fluorescent "tag" which allows the fusion polypeptide of the invention to be identified by fluorescence microscopy or by flow cytometry. The GFP tag is useful when assessing subcellular localisation of the fusion polypeptide of the invention, or for isolating cells which express the fusion polypeptide of the invention. Flow cytometric methods such as fluorescence activated cell sorting (FACS) are particularly useful in this latter application.

Preferably, the fusion partners also have protease cleavage sites, such as for Factor $X_a$ or Thrombin, which allow the relevant protease to partially digest the fusion polypeptide of the invention and thereby liberate the recombinant polypeptide of the invention therefrom. The liberated polypeptide can then be isolated from the fusion partner by subsequent chromatographic separation.

Fusion partners according to the invention also include within their scope "epitope tags", which are usually short peptide sequences for which a specific antibody is available. Well known examples of epitope tags for which specific monoclonal antibodies are readily available include c-Myc, influenza virus, haemagglutinin and FLAG tags.

The step of introducing into the host cell the recombinant polynucleotide may be effected by any suitable method including transfection, and transformation, the choice of which will be dependent on the host cell employed. Such methods are well known to those of skill in the art.

Recombinant polypeptides of the invention may be produced by culturing a host cell transformed with an expression vector containing nucleic acid encoding an immuno-interactive fragment, variant or derivative according to the invention. The conditions appropriate for protein expression will vary with the choice of expression vector and the host cell. This is easily ascertained by one skilled in the art through routine experimentation.

Suitable host cells for expression may be prokaryotic or eukaryotic. One preferred host cell for expression of a polypeptide according to the invention is a bacterium. The bacterium used may be *Escherichia coli*. Alternatively, the host cell may be an insect cell such as, for example, SF9 cells that may be utilised with a baculovirus expression system.

The recombinant protein may be conveniently prepared by a person skilled in the art using standard protocols as for example described in Sambrook, et al., MOLECULAR CLONING. A LABORATORY MANUAL (Cold Spring Harbor Press, 1989), in particular Sections 16 and 17; Ausubel et al., CURRENT PROTOCOLS IN MOLECULAR BIOLOGY (John Wiley & Sons, Inc. 1994–1998), in particular Chapters 10 and 16; and Coligan et al., CURRENT PROTOCOLS IN PROTEIN SCIENCE (John Wiley & Sons, Inc. 1995–1997), in particular Chapters 1, 5 and 6.

In some cases, the recombinant polypeptide may require refolding. Methods of refolding are well known to those of skill in the art.

Alternatively, the polypeptide may be isolated by the steps of:
  (a) obtaining an extract from a *Python* species;
  (b) fractionating the extract into a plurality of fractions; and
  (c) identifying and isolating one or more the said fractions, which neutralises or inhibits:
    (i) a venom or toxin; or
    (ii) phospholipase $A_2$.

Preferably, the *Python* species is *P. reticulatus*. Suitably, the extract is serum.

The fractionating step may be further characterised by removing immunoglobulins from the extract to provide an immunoglobulin-free fraction. Suitably, the fractionation step is effected by ammonium sulphate precipitation.

Suitably, the above method further comprises the step of detoxifying the extract. The extract is preferably detoxified by heating, for example, at 56° C. for 30 min.

Alternatively, the polypeptide, fragments, variants or derivatives of the invention may be synthesised using solution synthesis or solid phase synthesis as described, for example, in Chapter 9 of Atherton and Shephard (supra) and in Roberge et al (1995, *Science* 269: 202).

3. Polynucleotides of the Invention 3.1. Polynucleotides Encoding Polypeptides of the Invention The invention further provides a polynucleotide that encodes a polypeptide, fragment, variant or derivative as defined above. Suitably, the polynucleotide comprises the entire sequence of nucleotides set forth in SEQ ID NO: 1. SEQ ID NO: 1 corresponds to an 816 bp cDNA sequence obtained by reverse transcriptase PCR amplification as will be more fully described hereinafter. This sequence defines: (1) a 5' untranslated region from nucleotide through nucleotide 53 of SEQ ID NO: 1; (2) an open reading frame from nucleotide 54 through nucleotide 657; and (3) a 3' untranslated region from nucleotide 658 through nucleotide 816. The aforementioned open reading frame encodes a precursor polypeptide comprising a leader peptide encoded by nucleotides 54 through 110, and a mature polypeptide encoded by nucleotides 111 through 654. Suitably, the polynucleotide comprises the sequence set forth in SEQ ID NO: 3. SEQ ID NO: 3 defines the aforementioned open reading frame and thus encodes the said precursor polypeptide. Preferably, the polynucleotide comprises the sequence set forth in SEQ ID NO: 5, which corresponds to nucleotide 111 through nucleotide 654 and thus encodes the said mature polypeptide. SEQ ID NO: 7 corresponds to nucleotide 54 through 110 of SEQ ID NO: 1 and thus encodes the leader polypeptide of the aforementioned precursor polypeptide.

3.2. Polynucleotides Variants

In general, polynucleotide variants according to the invention comprise regions that show at least 60%, more suitably at least 70%, preferably at least 80%, and most preferably at least 90%, 95%, 98%, and even 99% sequence identity over a reference polynucleotide sequence of identical size ("comparison window") or when compared to an aligned sequence in which the alignment is performed by a computer homology program known in the art. What constitutes suitable variants may be determined by conventional techniques. For example, a polynucleotide according to any one of SEQ ID NO: 1, 3, 5 or 7 can be mutated using random mutagenesis (e.g., transposon mutagenesis), oligonucleotide-mediated (or site-directed) mutagenesis, PCR mutagenesis and cassette mutagenesis of an earlier prepared variant or non-variant version of an isolated natural promoter according to the invention.

Oligonucleotide-mediated mutagenesis is a preferred method for preparing nucleotide substitution variants of a polynucleotide of the invention. This technique is well known in the art as, for example, described by Adelman et al. (1983, *DNA* 2:183). Briefly, a polynucleotide according to any one of SEQ ID NO: 1, 3, 5 or 7 is altered by hybridising an oligonucleotide encoding the desired mutation to a template DNA, wherein the template is the single-stranded form of a plasmid or bacteriophage containing the unaltered or parent DNA sequence. After hybridisation, a DNA polymerase is used to synthesise an entire second complementary strand of the template that will thus incorporate the oligonucleotide primer, and will code for the selected alteration in said parent DNA sequence.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridise properly to the single-stranded DNA template molecule.

The DNA template can be generated by those vectors that are either derived from bacteriophage M13 vectors, or those vectors that contain a single-stranded phage origin of replication as described by Viera et al. (1987, *Methods Enzymol.* 153:3). Thus, the DNA that is to be mutated may be inserted into one of the vectors to generate single-stranded template. Production of single-stranded template is described, for example, in Sections 4.21–4.41 of Sambrook et al. (1989, supra).

Alternatively, the single-stranded template may be generated by denaturing double-stranded plasmid (or other DNA) using standard techniques.

For alteration of the native DNA sequence, the oligonucleotide is hybridised to the single-stranded template under suitable hybridisation conditions. A DNA polymerising enzyme, usually the Klenow fragment of DNA polymerase I, is then added to synthesise the complementary strand of the template using the oligonucleotide as a primer for synthesis. A heteroduplex molecule is thus formed such that one strand of DNA encodes the mutated form of the polypeptide or fragment under test, and the other strand (the original template) encodes the native unaltered sequence of the polypeptide or fragment under test. This heteroduplex molecule is then transformed into a suitable host cell, usually a prokaryote such as *E. coli*. After the cells are grown, they are plated onto agarose plates and screened using the oligonucleotide primer having a detectable label to identify the bacterial colonies having the mutated DNA. The resultant mutated DNA fragments are then cloned into suitable expression hosts such as *E. coli* using conventional technology and clones that retain the desired antigenic activity are detected. Where the clones have been derived using random mutagenesis techniques, positive clones would have to be sequenced in order to detect the mutation.

Alternatively, linker-scanning mutagenesis of DNA may be used to introduce clusters of point mutations throughout a sequence of interest that has been cloned into a plasmid vector. For example, reference may be made to Ausubel et al., supra, (in particular, Chapter 8.4) which describes a first protocol that uses complementary oligonucleotides and requires a unique restriction site adjacent to the region that is to be mutagenised. A nested series of deletion mutations is first generated in the region. A pair of complementary oligonucleotides is synthesised to fill in the gap in the sequence of interest between the linker at the deletion endpoint and the nearby restriction site. The linker sequence actually provides the desired clusters of point mutations as it is moved or "scanned" across the region by its position at the varied endpoints of the deletion mutation series. An alternate protocol is also described by Ausubel et al., supra, which makes use of site directed mutagenesis procedures to introduce small clusters of point mutations throughout the target region. Briefly, mutations are introduced into a sequence by annealing a synthetic oligonucleotide containing one or more mismatches to the sequence of interest cloned into a single-stranded M13 vector. This template is grown in an *E. coli* dut⁻ ung⁻ strain, which allows the incorporation of uracil into the template strand. The oligonucleotide is annealed to the template and extended with T4 DNA polymerase to create a double-stranded heteroduplex. Finally, the heteroduplex is introduced into a wild-type *E. coli* strain, which will prevent replication of the template strand due to the presence of apurinic sites (generated where uracil is incorporated), thereby resulting in plaques containing only mutated DNA.

Region-specific mutagenesis and directed mutagenesis using PCR may also be employed to construct polynucleotide variants according to the invention. In this regard, reference may be made, for example, to Ausubel et al, supra, in particular Chapters 8.2A and 8.5.

Alternatively, suitable polynucleotide sequence variants of the invention may be prepared according to the following procedure:

(a) creating primers which are optionally degenerate wherein each comprises a portion of a reference polynucleotide encoding a reference polypeptide or fragment of the invention, preferably encoding the sequence set forth in any one of SEQ ID NO: 2, or 6;

(b) obtaining a nucleic acid extract from a different *Python* species from which said reference polynucleotide is derived; and (c) using said primers to amplify, via nucleic acid amplification techniques, at least one amplification product from said nucleic acid extract, wherein said amplification product corresponds to a polynucleotide variant.

Suitable nucleic acid amplification techniques are well known to the skilled addressee, and include polymerase chain reaction (PCR) as for example described in Ausubel et al. (supra); strand displacement amplification (SDA) as for example described in U.S. Pat. No. 5,422,252; rolling circle replication (RCR) as for example described in Liu et al., (1996, *J. Am. Chem. Soc.* 118:1587–1594 and International application WO 92/01813) and Lizardi et al., (International Application WO 97/19193); nucleic acid sequence-based amplification (NASBA) as for example described by Sooknanan et al., (1994, *Biotechniques* 17:1077–1080); and Q-β replicase amplification as for example described by Tyagi et al., (1996, *Proc. Natl. Acad. Sci. USA* 93: 5395–5400).

Typically, polynucleotide variants that are substantially complementary to a reference polynucleotide are identified by blotting techniques that include a step whereby nucleic acids are immobilised on a matrix (preferably a synthetic membrane such as nitrocellulose), followed by a hybridisation step, and a detection step. Southern blotting is used to identify a complementary DNA sequence; northern blotting is used to identify a complementary RNA sequence. Dot blotting and slot blotting can be used to identify complementary DNA/DNA, DNA/RNA or RNA/RNA polynucleotide sequences. Such techniques are well known by those skilled in the art, and have been described in Ausubel et al. (1994–1998, supra) at pages 2.9.1 through 2.9.20.

According to such methods, Southern blotting involves separating DNA molecules according to size by gel electrophoresis, transferring the size-separated DNA to a synthetic membrane, and hybridising the membrane-bound DNA to a complementary nucleotide sequence labelled radioactively, enzymatically or fluorochromatically. In dot blotting and slot blotting, DNA samples are directly applied to a synthetic membrane prior to hybridisation as above.

An alternative blotting step is used when identifying complementary polynucleotides in a cDNA or genomic DNA library, such as through the process of plaque or colony hybridisation. A typical example of this procedure is described in Sambrook et al. ("Molecular Cloning. A Laboratory Manual", Cold Spring Harbour Press, 1989) Chapters 8–12.

Typically, the following general procedure can be used to determine hybridisation conditions. Polynucleotides are blotted/transferred to a synthetic membrane, as described above. A reference polynucleotide such as a polynucleotide of the invention is labelled as described above, and the ability of this labelled polynucleotide to hybridise with an immobilised polynucleotide is analysed.

A skilled addressee will recognise that a number of factors influence hybridisation. The specific activity of radioactively labelled polynucleotide sequence should typically be greater than or equal to about $10^8$ dpm/mg to provide a detectable signal. A radiolabelled nucleotide sequence of specific activity $10^8$ to $10^9$ dpm/mg can detect approximately 0.5 pg of DNA. It is well known in the art that sufficient DNA must be immobilised on the membrane to permit detection. It is desirable to have excess immobilised DNA, usually 10 µg. Adding an inert polymer such as 10% (w/v) dextran sulfate (MW 500,000) or polyethylene glycol 6000 during hybridisation can also increase the sensitivity of hybridisation (see Ausubel supra at 2.10.10).

To achieve meaningful results from hybridisation between a polynucleotide immobilised on a membrane and a labelled polynucleotide, a sufficient amount of the labelled polynucleotide must be hybridised to the immobilised polynucleotide following washing. Washing ensures that the labelled polynucleotide is hybridised only to the immobilised polynucleotide with a desired degree of complementarity to the labelled polynucleotide.

It will be understood that polynucleotide variants according to the invention will hybridise to a reference polynucleotide under at least low stringency conditions. Reference herein to low stringency conditions include and encompass from at least about 1% v/v to at least about 15% v/v formamide and from at least about 1 M to at least about 2 M salt for hybridisation at 42° C., and at least about 1 M to at least about 2 M salt for washing at 42° C. Low stringency conditions also may include 1% Bovine Serum Albumin (BSA), 1 mM EDTA, 0.5 M NaHPO$_4$ (pH 7.2), 7% SDS for hybridisation at 65° C., and (i) 2×SSC, 0.1% SDS; or (ii) 0.5% BSA, 1 mM EDTA, 40 mM NaHPO$_4$ (pH 7.2), 5% SDS for washing at room temperature.

Suitably, the polynucleotide variants hybridise to a reference polynucleotide under at least medium stringency conditions. Medium stringency conditions include and encompass from at least about 16% v/v to at least about 30% v/v formamide and from at least about 0.5 M to at least about 0.9 M salt for hybridisation at 42° C., and at least about 0.5 M to at least about 0.9 M salt for washing at 42° C. Medium stringency conditions also may include 1% Bovine Serum Albumin (BSA), 1 mM EDTA, 0.5 M NaHPO$_4$ (pH 7.2), 7% SDS for hybridisation at 65° C., and (i) 2×SSC, 0.1% SDS; or (ii) 0.5% BSA, 1 mM EDTA, 40 mM NaHPO$_4$ (pH 7.2), 5% SDS for washing at 42° C.

Preferably, the polynucleotide variants hybridise to a reference polynucleotide under high stringency conditions. High stringency conditions include and encompass from at least about 31% v/v to at least about 50% v/v formamide and from at least about 0.01 M to at least about 0.15 M salt for hybridisation at 42° C., and at least about 0.01 M to at least about 0.15 M salt for washing at 42° C. High stringency conditions also may include 1% BSA, 1 mM EDTA, 0.5 M NaHPO$_4$ (pH 7.2), 7% SDS for hybridisation at 65° C., and (i) 0.2×SSC, 0.1% SDS; or (ii) 0.5% BSA, 1 mM EDTA, 40 mM NaHPO$_4$ (pH 7.2), 1% SDS for washing at a temperature in excess of 65° C.

Other stringent conditions are well known in the art. A skilled addressee will recognise that various factors can be manipulated to optimise the specificity of the hybridisation. Optimisation of the stringency of the final washes can serve to ensure a high degree of hybridisation. For detailed examples, see Ausubel et al., supra at pages 2.10.1 to 2.10.16 and Sambrook et al. (1989, supra) at sections 1.101 to 1.104.

While stringent washes are typically carried out at temperatures from about 42° C. to 68° C., one skilled in the art will appreciate that other temperatures may be suitable for stringent conditions. Maximum hybridisation typically occurs at about 20° C. to 25° C. below the $T_m$ for formation of a DNA-DNA hybrid. It is well known in the art that the $T_m$ is the melting temperature, or temperature at which two complementary polynucleotide sequences dissociate. Methods for estimating $T_m$ are well known in the art (see Ausubel et al., supra at page 2.10.8).

In general, washing is carried out at T=69.3+0.41 (G+C) % −12° C. However, the $T_m$ of a duplex DNA decreases by 1° C. with every increase of 1% in the number of mismatched base pairs.

In a preferred hybridisation procedure, a membrane (e.g. a nitrocellulose membrane or a nylon membrane) containing immobilised DNA is hybridised overnight at 42° C. in a hybridisation buffer (50% deionised formamide, 5×SSC, 5× Denhardt's solution (0.1% ficoll, 0.1% polyvinylpyrollidone and 0.1% bovine serum albumin), 0.1% SDS and 200 mg/mL denatured salmon sperm DNA) containing labelled probe. The membrane is then subjected to two sequential medium stringency washes (i.e., 2×SSC/0.1% SDS for 15 min at 45° C., followed by 2×SSC/0.1% SDS for 15 min at 50° C.), followed by two sequential high stringency washes (i.e., 0.2×SSC/0.1% SDS for 12 min at 55° C. followed by 0.2×SSC and 0.1% SDS solution for 12 min).

Methods for detecting a labelled polynucleotide hybridised to an immobilised polynucleotide are well known to practitioners in the art. Such methods include autoradiography, phosphorimaging, and chemiluminescent, fluorescent and colorimetric detection.

4. Antigen-binding Molecules

The invention also contemplates antigen-binding molecules against the aforementioned polypeptides, fragments, variants and derivatives. For example, the antigen-binding molecules may comprise whole polyclonal antibodies. Such antibodies may be prepared, for example, by injecting a polypeptide, fragment, variant or derivative of the invention into a production species, which may include mice or rabbits, to obtain polyclonal antisera. Methods of producing polyclonal antibodies are well known to those skilled in the art. Exemplary protocols which may be used are described for example in Coligan et al., CURRENT PROTOCOLS IN IMMUNOLOGY, (John Wiley & Sons, Inc, 1991), and Ausubel et al., (1994–1998, supra), in particular Section III of Chapter 11.

In lieu of the polyclonal antisera obtained in the production species, monoclonal antibodies may be produced using the standard method as described, for example, by Köhler and Milstein (1975, *Nature* 256, 495–497), or by more recent modifications thereof as described, for example, in Coligan et al., (1991, supra) by immortalising spleen or other antibody producing cells derived from a production species which has been inoculated with one or more of the polypeptides, fragments, variants or derivatives of the invention.

The invention also contemplates as antigen-binding molecules Fv, Fab, Fab' and F(ab')$_2$ immunoglobulin fragments.

Alternatively, the antigen-binding molecule may comprise a synthetic stabilised Fv fragment. Exemplary fragments of this type include single chain Fv fragments (sFv, frequently termed scFv) in which a peptide linker is used to bridge the N terminus or C terminus of a $V_H$ domain with the C terminus or N-terminus, respectively, of a $V_L$ domain. ScFv lack all constant parts of whole antibodies and are not able to activate complement. Suitable peptide linkers for joining the $V_H$ and $V_L$ domains are those which allow the $V_H$ and $V_L$ domains to fold into a single polypeptide chain having an antigen binding site with a three dimensional structure similar to that of the antigen binding site of a whole antibody from which the Fv fragment is derived. Linkers having the desired properties may be obtained by the method disclosed in U.S. Pat. No. 4,946,778. However, in some cases a linker is absent. ScFvs may be prepared, for example, in accordance with methods outlined in Kreber et al (Krebber et al. 1997, *J. Immunol. Methods;* 201(1): 35–55). Alternatively, they may be prepared by methods described in U.S. Pat. No. 5,091,513, European Patent No 239,400 or the articles by Winter and Milstein (1991, *Nature* 349:293) and Plütckthun et al (1996, In *Antibody engineering: A practical approach.* 203–252).

Alternatively, the synthetic stabilised Fv fragment comprises a disulphide stabilised Fv (dsFv) in which cysteine residues are introduced into the $V_H$ and $V_L$ domains such that in the fully folded Fv molecule the two residues will form a disulphide bond therebetween. Suitable methods of producing dsFv are described for example in (Glockscuther et al. *Biochem.* 29: 1363–1367; Reiter et al. 1994, *J. Biol. Chem.* 269: 18327–18331; Reiter et al. 1994, *Biochem.* 33: 5451–5459; Reiter et al. 1994. *Cancer Res.* 54: 2714–2718; Webber et al. 1995, *Mol. Immunol.* 32: 249–258).

Also contemplated as antigen-binding molecules are single variable region domains (termed dAbs) as for example disclosed in (Ward et al. 1989, *Nature* 341: 544–546; Hamers-Casterman et al. 1993, *Nature.* 363: 446–48; Davies & Riechmann, 1994, *FEBS Lett.* 339: 285–290).

Alternatively, the antigen-binding molecule may comprise a "minibody". In this regard, minibodies are small versions of whole antibodies, which encode in a single chain the essential elements of a whole antibody. Suitably, the minibody is comprised of the $V_H$ and $V_L$ domains of a native antibody fused to the hinge region and CH3 domain of the immunoglobulin molecule as, for example, disclosed in U.S. Pat. No. 5,837,821.

In an alternate embodiment, the antigen binding molecule may comprise non-immunoglobulin derived, protein frameworks. For example, reference may be made to (Ku & Schultz, 1995, *Proc. Natl. Acad. Sci. USA,* 92: 652–6556) which discloses a four-helix bundle protein cytochrome b562 having two loops randomised to create complementarity determining regions (CDRs), which have been selected for antigen binding.

The antigen-binding molecule may be multivalent (i.e., having more than one antigen binding site). Such multivalent molecules may be specific for one or more antigens. Multivalent molecules of this type may be prepared by dimerisation of two antibody fragments through a cysteinyl-containing peptide as, for example disclosed by (Adams et al., 1993, *Cancer Res.* 53: 4026–4034; Cumber et al., 1992, *J. Immunol.* 149: 120–126). Alternatively, dimerisation may be facilitated by fusion of the antibody fragments to amphiphilic helices that naturally dimerise (Pack P. Plηnckthun, 1992, *Biochem.* 31: 1579–1584), or by use of domains (such as the leucine zippers jun and fos) that preferentially heterodimerise (Kostelny et al., 1992, *J. Immunol.* 148: 1547–1553). In an alternate embodiment, the multivalent molecule may comprise a multivalent single chain antibody (multi-scFv) comprising at least two scFvs linked together by a peptide linker. In this regard, non-covalently or covalently linked scFv dimers termed "diabodies" may be used. Multi-scFvs may be bispecific or greater depending on the number of scFvs employed having different antigen binding specificities. Multi-scFvs may be prepared for example by methods disclosed in U.S. Pat. No. 5,892,020.

The antigen-binding molecules of the invention may be used for affinity chromatography in isolating a natural or recombinant antitoxic polypeptide or biologically active fragment. For example reference may be made to immunoaffinity chromatographic procedures described in Chapter 9.5 of Coligan et al., (995–1997, supra).

The antigen-binding molecules can be used to screen expression libraries for variant polypeptides of the invention as described herein. They can also be used to detect antitoxic polypeptides, fragments, variants and derivatives as described hereinafter.

In addition, the antigen-binding molecules of the invention can be used to detect a phospholipase $A_2$ in biological sample, as described hereinafter.

5. Methods of Detection

5.1. Detection of Antitoxic Agents

The invention also extends to a method of detecting in a sample a polypeptide, fragment, variant or derivative as broadly described above, comprising contacting the sample with an antigen-binding molecule as described in Section 4 and detecting the presence of a complex comprising the said antigen-binding molecule and the said polypeptide, fragment, variant or derivative in said contacted sample.

Any suitable technique for determining formation of the complex may be used. For example, an antigen-binding molecule according to the invention, having a reporter molecule associated therewith may be utilised in immunoassays. Such immunoassays include, but are not limited to, radioimmunoassays (RIAs), enzyme-linked immunosorbent assays (ELISAs) and immunochromatographic techniques (ICTs), Western blotting which are well known those of skill in the art. For example, reference may be made to "CURRENT PROTOCOLS IN IMMUNOLOGY" (1994, supra) which discloses a variety of immunoassays that may be used in accordance with the present invention. Immunoassays may include competitive assays as understood in the art or as for example described infra. It will be understood that the present invention encompasses qualitative and quantitative immunoassays.

Suitable immunoassay techniques are described for example in U.S. Pat. Nos. 4,016,043, 4,424,279 and 4,018,653. These include both single-site and two-site assays of the non-competitive types, as well as the traditional competitive binding assays. These assays also include direct binding of a labelled antigen-binding molecule to a target antigen.

Two site assays are particularly favoured for use in the present invention. A number of variations of these assays exist, all of which are intended to be encompassed by the present invention. Briefly, in a typical forward assay, an unlabelled antigen-binding molecule such as an unlabelled antibody is immobilised on a solid substrate and the sample to be tested brought into contact with the bound molecule. After a suitable period of incubation, for a period of time sufficient to allow formation of an antibody-antigen complex, another antigen-binding molecule, suitably a second antibody specific to the antigen, labelled with a reporter molecule capable of producing a detectable signal is then added and incubated, allowing time sufficient for the formation of another complex of antibody-antigen-labelled antibody. Any unreacted material is washed away and the presence of the antigen is determined by observation of a signal produced by the reporter molecule. The results may be either qualitative, by simple observation of the visible signal, or may be quantitated by comparing with a control sample containing known amounts of antigen. Variations on the forward assay include a simultaneous assay, in which both sample and labelled antibody are added simultaneously to the bound antibody. These techniques are well known to those skilled in the art, including minor variations as will be readily apparent. In accordance with the present invention, the sample is one that might contain an antigen including serum, whole blood, and plasma or lymph fluid. The sample is, therefore, generally a circulatory sample comprising circulatory fluid.

In the typical forward assay, a first antibody having specificity for the antigen or antigenic parts thereof is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well known in the art and generally consist of cross-linking covalently binding or physically adsorbing, the polymer-antibody complex is washed in preparation for the test sample. An aliquot of the sample to be tested is then added to the solid phase complex and incubated for a period of time sufficient and under suitable conditions to allow binding of any antigen present to the antibody. Following the incubation period, the antigen-antibody complex is washed and dried and incubated with a second antibody specific for a portion of the antigen. The second antibody has generally a reporter molecule associated therewith that is used to indicate the binding of the second antibody to the antigen. The amount of labelled antibody that binds, as determined by the associated reporter molecule, is proportional to the amount of antigen bound to the immobilised first antibody.

An alternative method involves immobilising the antigen in the biological sample and then exposing the immobilised antigen to specific antibody that may or may not be labelled with a reporter molecule. Depending on the amount of target and the strength of the reporter molecule signal, a bound antigen may be detectable by direct labelling with the antibody. Alternatively, a second labelled antibody, specific to the first antibody is exposed to the target-first antibody complex to form a target-first antibody-second antibody tertiary complex. The complex is detected by the signal emitted by the reporter molecule.

From the foregoing, it will be appreciated that the reporter molecule associated with the antigen-binding molecule may include the following:

(a) direct attachment of the reporter molecule to the antigen-binding molecule;

(b) indirect attachment of the reporter molecule to the antigen-binding molecule; i.e., attachment of the reporter molecule to another assay reagent which subsequently binds to the antigen-binding molecule; and (c) attachment to a subsequent reaction product of the antigen-binding molecule.

The reporter molecule may be selected from a group including a chromogen, a catalyst, an enzyme, a fluorochrome, a chemiluminescent molecule, a lanthamide ion such as Europium ($Eu^{34}$), a radioisotope and a direct visual label.

In the case of a direct visual label, use may be made of a colloidal metallic or non-metallic particle, a dye particle, an enzyme or a substrate, an organic polymer, a latex particle, a liposome, or other vesicle containing a signal producing substance and the like.

A large number of enzymes suitable for use as reporter molecules is disclosed in United States Patent Specifications U.S. Pat. No. 4,366,241, U.S. Pat. No. 4,843,000, and U.S. Pat. No. 4,849,338. Suitable enzymes useful in the present invention include alkaline phosphatase, horseradish peroxidase, luciferase, β-galactosidase, glucose oxidase, lysozyme, malate dehydrogenase and the like. The enzymes may be used alone or in combination with a second enzyme that is in solution.

Suitable fluorochromes include, but are not limited to, fluorescein isothiocyanate (FITC), tetramethylrhodamine isothiocyanate (TRITC), R-Phycoerythrin (RPE), and Texas Red. Other exemplary fluorochromes include those discussed by Dower et al. (International Publication WO 93/06121). Reference also may be made to the fluorochromes described in U.S. Pat. Nos. 5,573,909 (Singer et al), 5,326,692 (Brinkley et al). Alternatively, reference may be made to the fluorochromes described in U.S. Pat. Nos. 5,227,487, 5,274,113, 5,405,975, 5,433,896, 5,442,045, 5,451,663, 5,453,517, 5,459,276, 5,516,864, 5,648,270 and 5,723,218.

In the case of an enzyme immunoassay, an enzyme is conjugated to the second antibody, generally by means of glutaraldehyde or periodate. As will be readily recognised, however, a wide variety of different conjugation techniques exist which are readily available to the skilled artisan. The substrates to be used with the specific enzymes are generally chosen for the production of, upon hydrolysis by the corresponding enzyme, a detectable colour change. Examples of suitable enzymes include those described supra. It is also possible to employ fluorogenic substrates, which yield a fluorescent product rather than the chromogenic substrates noted above. In all cases, the enzyme-labelled antibody is added to the first antibody-antigen complex. It is then allowed to bind, and excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of antigen which was present in the sample.

Alternately, fluorescent compounds, such as fluorescein, rhodamine and the lanthamide, europium (EU), may be chemically coupled to antibodies without altering their binding capacity. When activated by illumination with light of a particular wavelength, the fluorochrome-labelled antibody adsorbs the light energy, inducing a state to excitability in the molecule, followed by emission of the light at a characteristic colour visually detectable with a light microscope. The fluorescent-labelled antibody is allowed to bind to the first antibody-antigen complex. After washing off the unbound reagent, the remaining tertiary complex is then exposed to light of an appropriate wavelength. The fluorescence observed indicates the presence of the antigen of interest. Immunofluorometric assays (IFMA) are well established in the art. However, other reporter molecules, such as radioisotope, chemiluminescent or bioluminescent molecules may also be employed.

5.2. Detection of Phospholipase $A_2$

The presence of unneutralized phospholipase $A_2$ in a patient is indicative of envenomation, for instance snake-related envenomation caused e.g. by a Russell's viper species. The level of $PLA_2$ presence may be determined by isolating a biological sample from the patient, contacting the biological sample with a polypeptide, fragment variant or derivative according to the invention, and detecting the presence of a complex comprising said polypeptide, fragment variant or derivative combined with the unneutralized phospholipase $A_2$ derived from the patient.

This invention also contemplates a corresponding method of diagnosing a condition associated with an aberrant concentration of a phospholipase $A_2$ in a biological sample of a patient. The method comprises contacting the biological sample with a polypeptide, fragment variant or derivative according to the invention, measuring the concentration of a complex comprising the said polypeptide, fragment variant or derivative and the phospholipase $A_2$ in said contacted sample, and relating said measured complex concentration to the concentration of phospholipase $A_2$ in said sample, wherein the presence of said aberrant concentration is indicative of the condition. Typically, the condition is envenomation and more usually snake-related envenomation. Preferredly, the snake-related envenomation is envenomation caused by a Russell's viper species.

Any suitable technique for determining formation of the complex may be used. For example, a polypeptide, fragment, variant or derivative according to the invention, having a reporter molecule associated therewith may be utilised in solution or solid-phase assays as is known in the art, inclusive of competitive and non-competitive formats.

6. Compositions

The invention also provides a composition for use in treating envenomation, or in treating or preventing inflammatory conditions suitably associated with phospholipase $A_2$, comprising a polypeptide, biologically active fragment, variant or derivative as broadly described above ("therapeutic agents"), together with a pharmaceutically acceptable carrier. Suitably, the phospholipase $A_2$ associated inflammatory condition includes, but is not limited to, bacterial or fungal infections, osteoarthritis, rheumatoid arthritis, and osteoporosis, in which the excess activity of the phospholipases, producing arachidonic acid or diacylglycerol and contributing to the formation of eicosanoids, causes inflammation, tissue destruction, impaired function or death.

Depending upon the particular route of administration, a variety of pharmaceutically acceptable carriers, well known in the art may be used. These carriers may be selected from sugars, starches, cellulose and its derivatives, malt, gelatine, talc, calcium sulphate, vegetable oils, synthetic oils, polyols, alginic acid, phosphate buffered solutions, emulsifiers, isotonic saline, and pyrogen-free water.

Any suitable route of administration may be employed for providing a mammal or a patient with a composition of the invention. For example, oral, rectal, parenteral, sublingual, buccal, intravenous, intra-articular, intra-muscular, intra-dermal, subcutaneous, inhalational, intraocular, intraperitoneal, intracerebroventricular, transdermal and the like may be employed.

Dosage forms include tablets, dispersions, suspensions, injections, solutions, syrups, troches, capsules, suppositories, aerosols, transdermal patches and the like. These dosage forms may also include injecting or implanting controlled releasing devices designed specifically for this purpose or other forms of implants modified to act additionally in this fashion. Controlled release of an immunogenic or a therapeutic agent may be effected by coating the same, for example, with hydrophobic polymers including acrylic resins, waxes, higher aliphatic alcohols, polylactic and polyglycolic acids and certain cellulose derivatives such as hydroxypropylmethyl cellulose. In addition, controlled release may be effected by using other polymer matrices, liposomes and/or microspheres.

Compositions suitable for oral or parenteral administration may be presented as discrete units such as capsules, sachets or tablets each containing a pre-determined amount of one or more immunogenic agents of the invention, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association one or more immunogenic agents as described above with the carrier which constitutes one or more necessary ingredients. In general, the compositions are prepared by uniformly and intimately admixing the immunogenic agents of the invention with liquid carriers or finely divided solid carriers or both, and then, if necessary, shaping the product into the desired presentation.

The above compositions may be administered in a manner compatible with the dosage formulation, and in such amount as is therapeutically effective. In this regard, the dose of therapeutic agent administered to a patient should be sufficient to effect a beneficial response in the patient over time such as a reduction in the level of phospholipase $A_2$ or to ameliorate the condition (e.g., envenomation) to be treated. The quantity of the therapeutic agent(s) to be administered may depend on the subject to be treated inclusive of the age, sex, weight and general health condition thereof. In this regard, precise amounts of the therapeutic agent(s) for administration will depend on the judgement of the practitioner. In determining the effective amount of the therapeutic agent to be administered in the treatment or prophylaxis of the condition associated with aberrant levels of a phospholipase $A_2$, the physician may evaluate circulating plasma levels, and progression of the condition.

In any event, those of skill in the art may readily determine suitable dosages of the therapeutic agents of the invention. Such dosages may be in the order of nanograms to milligrams of these agents.

7. Detection Kits

The present invention also provides kits for the detection of a phospholipase $A_2$ in a biological sample. These will contain one or more agents described above depending upon the nature of the test method employed. In this regard, the kits may include one or more of a polypeptide, fragment, variant, derivative, or antigen-binding molecule according to the invention. The kits may also optionally include appropriate reagents for detection of labels, positive and negative controls, washing solutions, dilution buffers and the like.

In order that the invention may be readily understood and put into practical effect, particular preferred embodiments will now be described by way of the following non-limiting examples.

EXAMPLES

The following non-limiting Examples illustrate various aspects of the present invention.

Example 1

Neutralisation Properties of Sera Obtained from Python and Other Animals

Whole (unfractionated) sera of python and various animals were tested for their neutralising property against the lethality of Russell's viper (*Daboia russelli siamensis*) venom. The results of TABLE 1 clearly show that out of nine serum samples examined, python serum is the only specimen rendering protection against lethal doses of Russell's viper venom. 2 $LD_{50}$ intraperitoneal dose of the venom and up to 5 $LD_{50}$ intraperitoneal dose of the major lethal toxin (daboiatoxin) of Russell's viper venom can be effectively neutralised by as little as 40 µL (3 mg protein) of whole python serum. At higher doses (4$LD_{50}$) of venom, 40 µL of python serum used in the experiment is inadequate to give full protection, indicating that a corresponding increase in the amount of python serum is required to achieve complete neutralisation when higher doses of venom are used (TABLE 1).

The neutralising action of whole python serum against the other biological activities of Russell's viper venom, like neurotoxicity and indirect haemolytic activity, are shown in FIGS. 1A and 1C, respectively. With in vivo animal experiments (as shown in TABLE 1), the neurotoxic symptoms (hind limb paralysis, impaired body movement, etc) were significantly diminished in mice injected with venom pretreated with whole python serum.

With in vitro inhibition experiments using rat brain synaptosomes and $^{125}$Iodine labelled daboiatoxin ($^{125}$I-DbTx) of Russell's viper venom, python serum was equally effective as hyperimmune DbTx antisera in inhibiting $^{125}$I-DbTx specific binding to rat brain synaptosomes. Both python serum and DbTx antisera gave $IC_{50}$ values of 1:6,000 serum dilutions (i.e., 1 µg serum protein gives 50% inhibition of $^{125}$I-DbTx synaptosomal binding) whereas the $IC_{50}$ values in the vicinity of 1:500 serum dilutions (i.e., 50 µg and above required to show 50% inhibition) were obtained for other animal sera tested (FIG. 1A). Whole python serum inhibited the $PLA_2$ catalytic activity of crude Russell's viper venom and its major lethal toxin DbTx. With 0.5 mg of python serum protein, a 50% inhibition of $PLA_2$ activity was achieved whereas the other sera tested showed less than 20% inhibition even at higher serum concentrations used (3 to 4-mg protein). The inhibition potency of python serum against the $PLA_2$ activity of DbTx was the same as that of hyperimmune specific DbTx antibodies (FIG. 1B).

For completely inhibiting the in vitro indirect haemolytic activity of Russell's viper venom (200 µg), only 40 µL (3 mg python serum protein) was required while commercial specific antivenin used at double this amount (6 mg immunoglobulins) did not give complete inhibition. All other sera examined showed very little inhibition even at higher serum (4–5 mg protein) concentrations (FIG. 1C).

Example 2

Purification of an Antitoxic Agent from *P. reticulatus*

A highly active therapeutic agent against lethal venom and toxin of a viperid, Russell's viper (*Daboia russelli siamensis*), has been purified from the serum of the non-venomous snake python (*Python reticulatus*). For the purpose of the present invention, this agent has been designated Python Antitoxic Factor or PAF.

In summary, native PAF was purified as follows: (1) python serum was obtained; (2) the serum was detoxified by heating at 56° C. for 30 min; (3) the detoxified serum was fractionated; and (4) fractions comprising the neutralising activity for Russell's viper venom were identified and isolated.

In more detail, the fractionation step comprises obtaining an immunoglobulin-free fraction by 45–80% ammonium sulphate precipitation of the crude python serum and testing the in vitro $PLA_2$ inhibition activity and the in vivo lethal venom neutralisation activity. In more detail, python serum was fractionated into immunoglobulin and immunoglobulin-free components by 45–80% ammonium sulphate treatment. The precipitated immunoglobulin fractions and the immunoglobulin-free fraction, after dialysis, were tested against the lethality and local effects (oedematogenic activity and myotoxicity) of the Russell's viper venom. The effectiveness of python whole serum and its immunoglobulin-free fraction in inhibiting the toxic effects of the venom as compared with specific neutralising antibodies is presented in TABLE 2. The results clearly show that a protective factor resides in the non-immunoglobulin fraction of the python serum, indicating that the neutralisation of the toxic effects of the Russell's viper venom is not due to antigen-antibody reaction.

The immunoglobulin-free fraction exhibiting relatively higher inhibitory activity than the specific neutralising antibodies of the commercial antivenin is further rechromatographed on UNO Q1™ (Bio-Rad) anion exchange column of a fast protein liquid chromatography (FPLC) system (Pharmacia) with an aqueous gradient Tris-HCl buffer having the pH 8.2 and molarity in the gradient range of 0.025M to 0.50M. The eluted fraction with most $PLA_2$ neutralising activity, after desalting with ultrafree-15 centrifugal filter device (Millipore) and lyophilisation, is dissolved in 0.05M Tris buffer (pH 7.2) containing 8M urea and fractionated under denaturing conditions on a HiLoad 16/60 Superdex™ 75 preparative gel filtration column (Pharmacia) connected to a FPLC system. The eluted fractions are ultrafiltrated to remove the denaturant, and examined for the in vivo lethal neutralising activity in mice and in vitro $PLA_2$ inhibitory activity. The fraction having such activities was named the 'Python Antitoxic Factor' (PAF). PAF is finally purified from of traces of contaminants on a C18 Sephasil™ reverse phase HPLC column on SMART™ system with an elution gradient from 0–60% of 80% acetonitrile/0.1% TFA.

A substantially pure protein was isolated from these fractions, which was reduced and S-pyridylethylated. Amino acid sequence analysis of this protein on an Applied Biosystems Model 940 Sequencer revealed that PAF comprises the 32 residue N-terminal sequence set forth in SEQ ID NO: 9.

Figure 2:
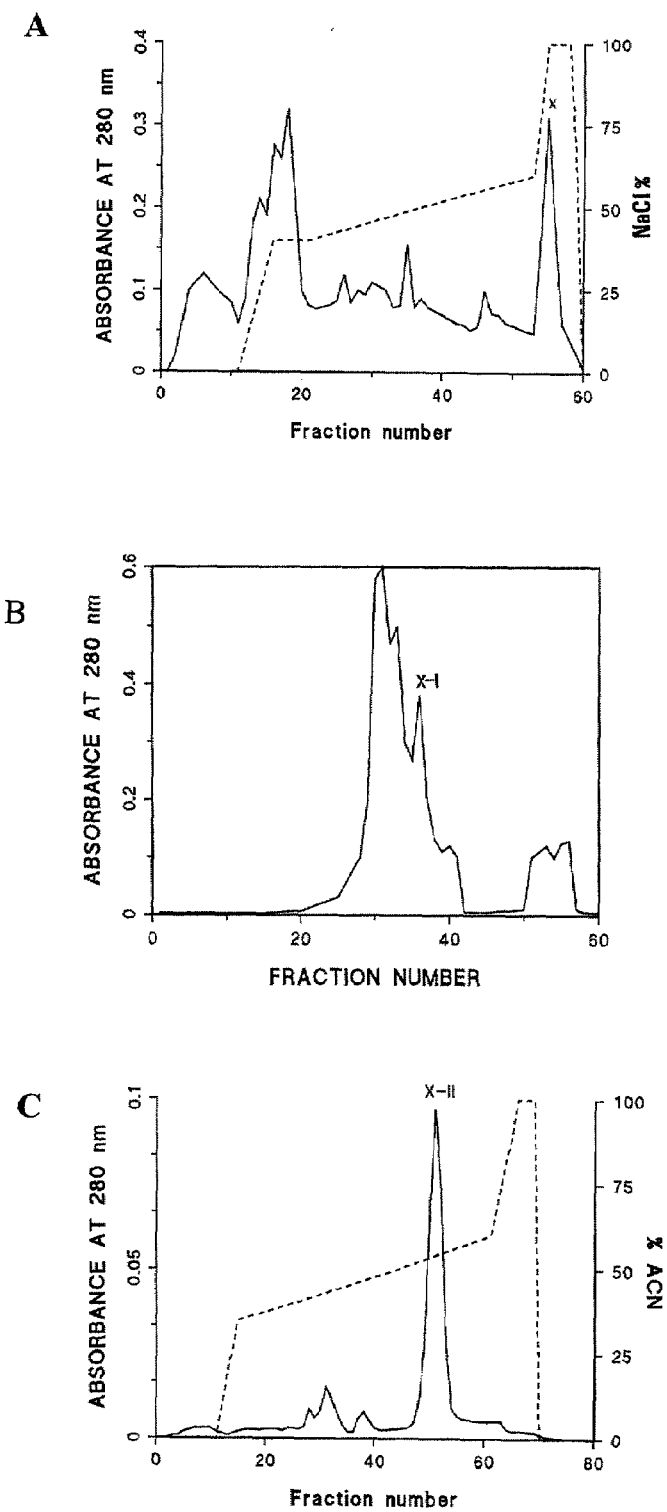

The 45–80% ammonium sulphate precipitated python serum fraction (100 mg protein) was fractionated on a FPLC system (Pharmacia) using a Bio-Rad anion exchange column (Type UNO Q1™, 7×35 mm), maintained at 20° C. Fractionation was achieved by elution of the loaded proteins (10 mg of desalted immunoglobulin-free python serum proteins in 0.025M Tris-HCl containing 0.05M NaCl, pH 8.2) at a flow rate of 2 mL/min, with a gradient Tris-HCl buffer having pH 8.2 and NaCl molarity gradient in the range 0.05 M to 0.5M (FIG. 2A). Eluted fractions were individually pooled from several FPLC runs, desalted with Ultrafree-15™ centrifugal filter device (Millipore), and the protein concentration for each fraction measured by Bio-Rad dye-based protein assay. For testing the inhibitory activity against lethality and $PLA_2$ catalytic activity, 100 µg of the protein from each fraction was used versus 20 µg of Russell's viper venom. The fraction number X, which showed the highest potency to neutralise $PLA_2$ activity and the lethal effects of venom was pooled, lyophilised, reconstituted in 0.05 M Tris-HCl buffer, pH 7.2, containing 8 M urea, and incubated at 37° C. for 30 min prior to fractionation on a Pharmacia FPLC system using a HiLoad 16/60 Superdex 75™ column. Two-milligram protein samples of urea-treated fraction X was fractionated each time, at a flow rate of 0.5 mL/min, for several FPLC runs under identical conditions (FIG. 2B) and the corresponding fractions pooled, desalted, and tested for inhibitory activity against $PLA_2$ and lethal activity of Russell's viper venom. The fraction number X-I is the purified python antitoxic factor PAF showing strong potency to neutralise the lethal effect of Russell's viper venom and its $PLA_2$ enzymatic activity.

The purified PAF was concentrated by ultracentrifugation and the sample (100 µg protein per run), after dissolving in 0.1% trifluoroacetic acid (TFA), was chromatographed on a C18 Sepbasil™ reverse phase HPLC column (5 µm SC 2.1/10), equilibrated with the same acidic solution. Elution was performed by linear gradient of 0–60% of 80% acetonitrile/0.1% TFA, at a flow rate of 0.3 mL/min, and 0.3-mL fractions were collected. The fractions under each peak were pooled and lyophilised (FIG. 2C). Corresponding fractions from several runs were pooled, concentrated and fractionated again on the same C18 Sephasil RP-HPLC column under identical conditions to give a pure PAF, which was used for N-terminal amino acid sequencing.

Inhibitory activities of the crude serum, the active pools from each purification steps and the purified factor PAF were evaluated by the residual $PLA_2$ activity of Russell's viper (*Daboia russelli siamensis*) venom or its principal toxin DbTx, after incubation with the test samples. In vivo neutralisation assays were also performed in Swiss albino mice (20–22 g) by intraperitoneal injection of 2 $LD_{50}$ doses of venom previously incubated for 30 min at 37° C. with the test samples. A summary of the purification procedure is presented in TABLE 3.

Figure 3:
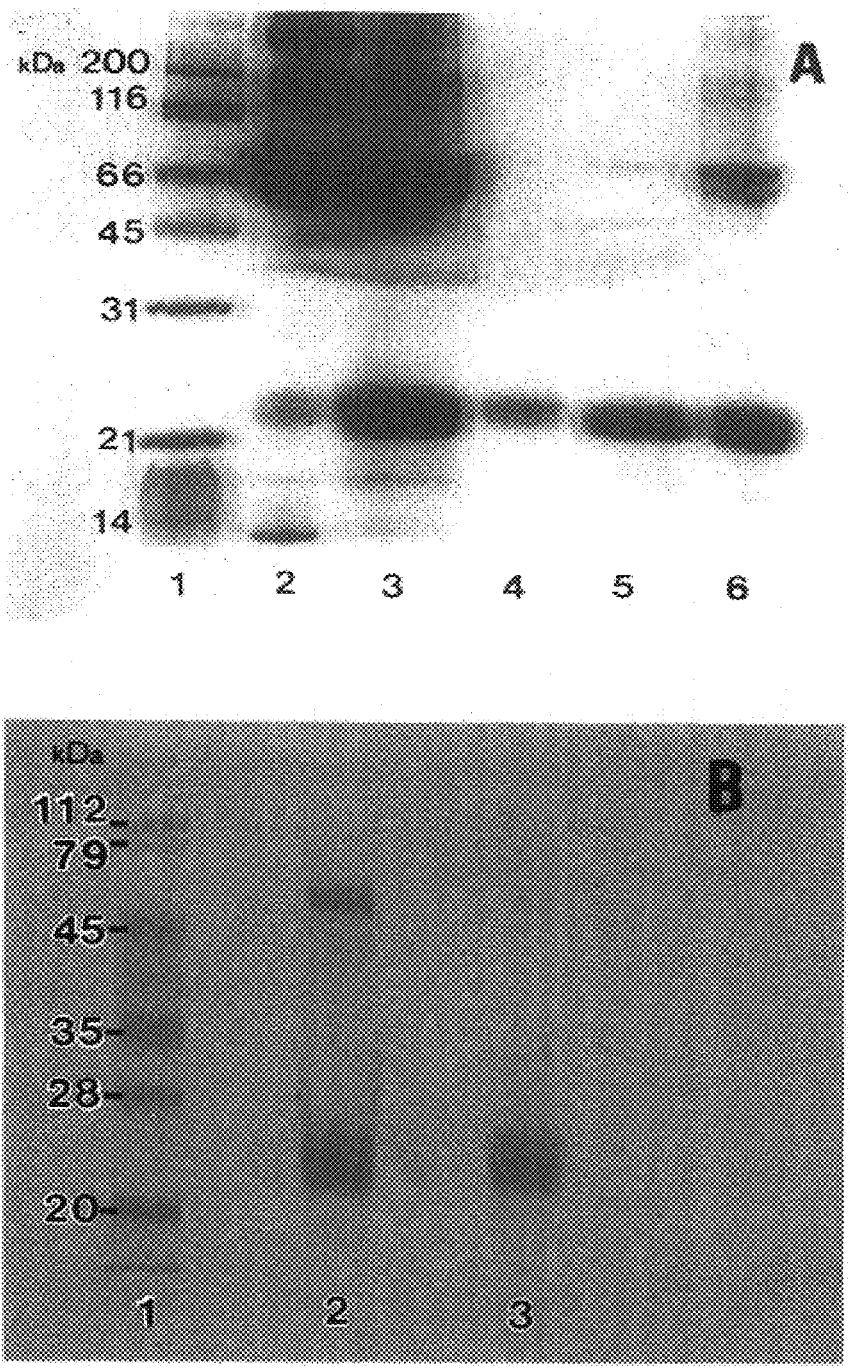
Figure 4:
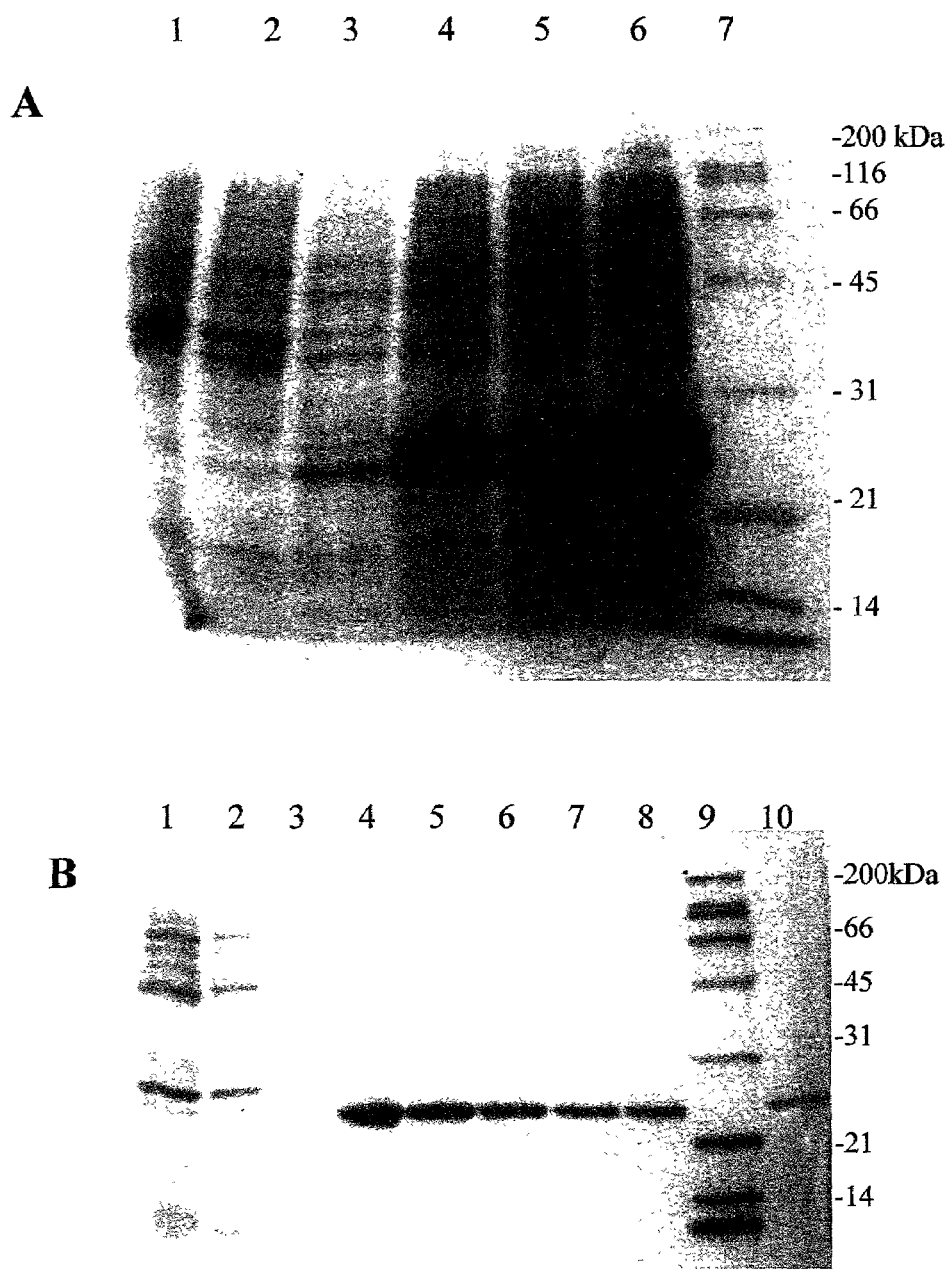
Figure 5:
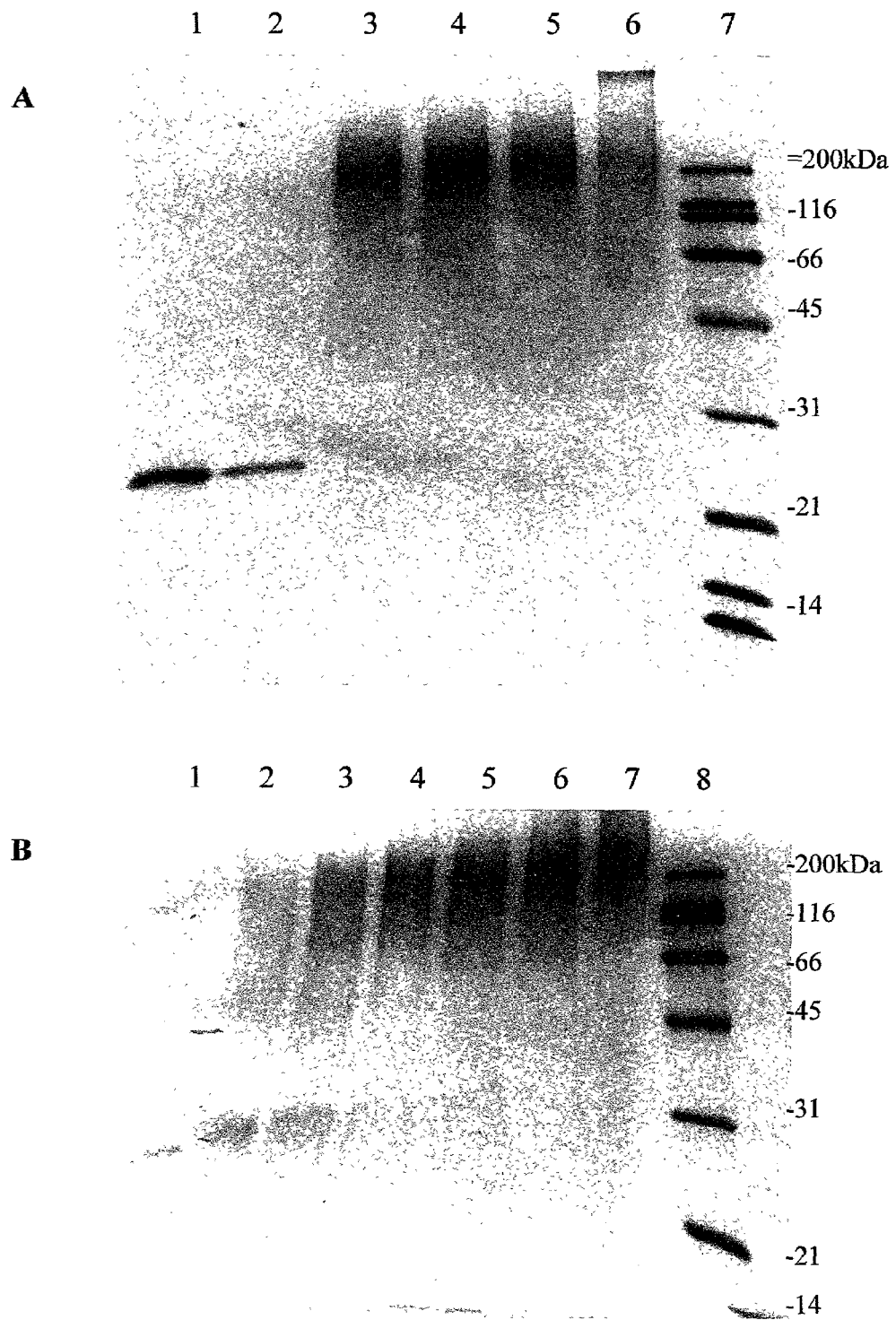

A sample of protein obtained after Sephasil C18 RP-HPLC was analysed by 12% SDS-PAGE under reducing conditions. This analysis revealed that the sample contained a single blurred protein band for PAF with an apparent molecular weight of about 23-kDa, suggesting that PAF comprises only one species of subunit molecule (FIG. 3A). This value corresponded closely with the subunit molecular weight of PAF determined by mass spectrometry (i.e., about 23-kDa). The glycosylation state of the PAF molecule was ascertained by a positive signal obtained with Western blots of PAF using the BioRad Immunoblot™ kit for glycoprotein detection (FIG. 3B). However, persons of skill in the art will understand that estimation of protein molecular weights can vary markedly depending at least in part on the method of molecular weight determination employed and the glycosylation state of the protein. Accordingly, apparent molecular weights for the antitoxic agent of the invention preferably fall within the range of between 15-kDa and 30-kDa, more preferably between 20-kDa and 26-kDa.

Example 3

Cloning and Expression of Recombinant Antitoxic Agent

In summary, cloning and expression of recombinant PAF was facilitated by: (1) isolating total RNA from the liver of *Python reticulatus*, amplifying a polynucleotide encoding PAF by RT-PCR, cloning the amplicon into a vector and sequencing the said polynucleotide; (2) amplifying the coding region for mature PAF by PCR, using primers designed from the sequence data, with restriction enzyme sites flanking the structural region of PAF; (3) cloning of the reconstructed recombinant DNA into the expression vector pQE30 in *E. coli* to produce a fusion protein with a hexa-histidine tag; (4) inducing recombinant pQE30-PAF with IPTG; and (5) affinity purifying the recombinant PAF from lysed cells by imidazole elution from a Ni-chelate column.

In more detail, total RNA was isolated from the liver of *Python reticulatus*, by the guanidinium isothiocyanate extraction method (Ullrich et al. 1977; *Science* 196: 1313) and the integrity of the total RNA was analysed by denaturing formaldehyde agarose gel electrophoresis. An uncloned library of adaptor-ligated double stranded cDNA was then obtained by RT-PCR from the total RNA. Based on the N-terminal amino acid sequence of PAF (SEQ ID NO: 9), an oligonucleotide primer was deduced using the PrimerSelect™ program from DNASTAR (USA). The deduced primer GSP-1 primer (custom synthesised by NUMI Research Services, NUS) and an adaptor primer (AP 1, Marathon cDNA Amplification kit, Clontech) were used as the forward and reverse primers, respectively to amplify the adaptor-ligated double stranded cDNA by PCR. The resulting 800-bp fragment was cloned into pT7Blue(R) vector after which the ligated products were transformed into competent *E. coli* cells (NovaBlue™) and the transformants selected on Luria Broth plate supplemented with ampicillin, IPTG and X-Gal. Putative recombinant plasmids were then subjected to Sanger dideoxy DNA sequencing (Sanger et al. 1977; *Proc. Natl. Acad. Sci. U.S.A.* 74, 5463) on an Automated DNA Sequencer, the details of which have previously been described in Jayaseelan et al (1998; *BBA* 1380, 209–222). The sequence thus obtained spanned the coding region of PAF and the 3'-flanking region. Based on this sequence data, a reverse primer (GSP-2) was prepared and used along with an adaptor primer AP 1 to amplify the adaptor-ligated double stranded cDNA by PCR. A 360-bp fragment thus obtained was subcloned and sequenced thereby providing nucleotide sequence information on the 5'-flanking region comprising the 5'-UTR, the signal sequence, and a portion of the coding region of PAF. Based on the sequence data generated from the two cloned fragments, the complete nucleotide sequence of PAF cDNA was established and the amino acid sequence deduced.

The nucleic acid and deduced amino acid sequences of PAF are given in SEQ ID NO: 1 and 2, respectively. The full-length cDNA of PAF is 816 bp with a 5'-UTR of 53 bp, followed by an open reading frame (ORF) region of 603 bp with the first initiation codon present at position 54 and the first termination codon (TAA) at position 657. The 3'-UTR is 160 bp long and contains a putative polyadenylation signal—AATAAA (SEQ ID NO:33)—at position 795, which is 16 nucleotides upstream of the poly-A tail. The ORF predicts a 201 amino acid polypeptide precursor for PAF that includes a signal peptide of 19 amino acids in length and a peptide containing 182 amino acids with an N-terminal sequence identical to that obtained from direct amino acid sequence analysis of the native PAF as described in SEQ ID NO: 9. The sequence given in SEQ ID NO: 9 infers that the monomer subunit of PAF is composed of 182 amino acid residues.

For expression of PAF, the cDNA sequence encoding the protein sequence to be expressed was amplified by PCR and cloned into the QIAexpress™ pQE-30 expression vector to produce a 6×His-tagged fusion protein in NovaBlue™ E. coli competent cells (Novagen). PCR primers with restriction enzyme sites flanking the PAF coding region were designed from the sequence data (SEQ ID NO: 1 and 2). A HindIII site was included into the 3' PCR primer, while the 5' primer incorporated a BamHI site. The reconstructed 600-bp DNA fragment was cleaved with restriction endonucleases BamHI and HindIII, gel purified and ligated to similarly prepared pQE-30 plasmid DNA. The ligated product was then transformed into competent *E. coli* cells (NovaBlue). The resulting clone PAF-pQE-30 was analysed by restriction digestion and screened for the presence of PAF sequence by PCR. Recombinant cells were grown at 37° C. in LB-Amp media until $A_{600}$~0.65, and then induced with IPTG to a final concentration of 1 mM at 37° C. Cells were harvested after 4 h, resuspended in lysis buffer [50 mM Tris-HCl (pH 8.5), 10 mM 2-mercaptoethanol, 1 mM PMSF] and lysed under denaturing conditions in 8 M urea by gentle vortexing and sonication. Cell debris was cleared by centrifugation [10,000×g, 30 min, 4° C.] and cleared cell lysates were collected for affinity purification on a column packed with 2 mL Ni-NTA agarose (QIAGEN) resin.

FIG. 4A shows the time-course analysis of the level of protein expression in optimising the expression of the PAF-pQE-30 construct. Unbound proteins were eluted from the column with buffer A [20 mM Tris-HCL (pH 8.5), 100 mM KCl, 20 mM imidazole, 10 mM 2-mercaptoethanol, 10% (v/v) glycerol], followed by two successive washes with Buffer A and Buffer B [20 mM Tris (pH 8.5), 1 M KCl, 10 mM 2-mercapethanol, 10% (v/v) glycerol], respectively. The recombinant protein was eluted with a step-wise gradient (100, 150, 200, 400, 800 mM imidazole) in Buffer C [20 mM Tris (pH 8.5), 100 mM KCl, 10 mM 2-mercapethanol, 10% (v/v) glycerol]. About 6 mg protein per liter culture was obtained from the Ni-NTA column. On SDS-PAGE (12% reducing gel) in FIG. 4B, the eluted protein shows a single sharp band at 23-kDa, which is the expected monomeric size for the recombinant PAF.

Renaturation of the eluted protein was achieved by dilution in Tris buffer (pH 7.5) containing 100 mM KCl, and removal of denaturants slowly by ultrafiltration using Centricon plus™ 80 membrane filter (Millipore). Recombinant PAF was purified further by anion exchange (UNO Q6™, FPLC) and reverse-phase (Sephasil™ C18, HPLC) chromatography, before analysis by N-terminal sequencing to confirm the amino acid sequence of the N-terminal end. After Ni-NTA chromatography, the recombinant PAF behaves very similar to the native PAF in its chromatographic profiles obtained from anion exchange and reverse-phase HPLC chromatography. The migrations of the about 23-kDa monomer subunits were also indistinguishable between the native and recombinant proteins on SDS-PAGE. Elution profiles of molecular sieve chromatography (Superdex™ 200) runs performed with the native and recombinant PAF also indicate that the molecular size of both proteins are similar and determined to be in the range of 140–150 kDa (data not shown).

Chemical cross-linking experiments show that the homogenous about 23-kDa subunits of the native or recombinant PAF can be cross-linked to form an oligomeric molecular aggregate of about 140-kDa, indicating that PAF is composed of six homogenous about 23-kDa subunits (FIG. 5). The native PAF has an apparent molecular mass of about 140-kDa as determined by Superdex™ 200 FPLC gel filtration chromatography (data not shown), thus confirming the oligomeric nature of PAF existing as a hexamer of about 23-kDa subunits.

Example 4

Neutralising Effects of Native Anti-toxic Agent

The neutralising activity of native PAF against 2 $LD_{50}$ intraperitoneal dose of *Daboia russelli siamensis* venom in mice exceeds that of the commercial specific antivenin (0.05 mg PAF vs. 6.0 mg specific neutralising immunoglobulins), indicating its life-saving utility potential (TABLE 4)

The results from TABLE 4 show that native PAF is non-toxic and is also effective in affording protection in mice against the toxicity of venoms from other Russell's viper subspecies found in this region—*Daboia russelli russelli* (India), *Daboia russelli siamensis* (Thailand), *Daboia russelli pulchella* (Sri Lanka). This therefore suggests that PAF can be an effective antidote not only for bites by one subspecies of Russell's viper (*Daboia russelli*), but can also work against envenomations caused by other subspecies found in the region. This could result in a relatively universal antivenin drug for treatment of all Russell's viper bites, irrespective of subspecies differences. Hence, the present invention encompasses the use of PAF or any pharmaceutical compositions comprising PAF for the study, prevention or treatment of bites by all types of Russell's viper, irrespective of species differences.

TABLE 5 shows the anti-lethal activity of recombinant PAF against various snake venoms and toxic $PLA_2$s. The lethal activity of the venoms and $PLA_2$ toxins from different subspecies of a Viperidae snake *Daboia russelli* was most effectively inhibited while inhibition of lethality induced in mice by other group II Crotalidae (*Agkistrodon halys blomhoffii*) venom and Viperidae (*Vipera ammodytes*) toxin, ammodytoxin A, was less remarkable. Venoms and toxins from Elapidae (*Oxyuranus scutellatus, Pseufrchis textilis*) were also inhibited to less extent. However, the overall results indicate that PAF can neutralise the lethal effects of all the group I, II, and III $PLA_2$ venoms and toxins, and can be used as an antivenin drug for treatment of snake envenomation, preferably of Russell's viper (*Daboia russelli*) bites.

Besides its potential utility as an antivenin drug for treatment of a wide range of snake envenomations, PAF may also be useful as a novel therapeutic drug for inflammatory diseases. The recombinant PAF has very potent anti-inflammatory effect on the $PLA_2$-induced mouse footpad oedema. TABLE 6 shows the anti-inflammatory effect of recombinant PAF compared to that of known anti-inflammatory peptide-2 commercially available from Sigma. Coinjection of recombinant PAF with $PLA_2$s either from *Daboia russelli siamensis* venom or its major toxic $PLA_2$ (Daboiatoxin) or from bee venom, resulted in significant reduction of oedema formation in a dose-dependent manner with maximal suppression of the inflammatory response (75–92%) observed at a dose level of 100 μg PAF. At a 50 μg dose, PAF (under the experimental conditions used) has an anti-inflammatory activity comparable to that of the Sigma anti-inflammatory peptide-2. Despite the larger doses used, the specific neutralising antibodies like *Daboia r. siamensis* antivenin (150 μg) and anti-daboiatoxin antiserum (0.8 mg protein), on the other hand, had insignificant inhibitory effect on $PLA_2$-induced mouse footpad oedema.

The PLA$_2$ inhibitory peptide of the present invention is first identified through a computer generated database search for amino acid sequence alignments using the mature PIP amino acid sequence, the full sequence of which has been initially disclosed as SEQ ID No. 2 and 6 herein, and later submitted to GenBank (Accession No. AAF73945). PSI-BLAST [Altschul S. F et al. (1997) *Nucleic Acids Res.* 25, 3389–3402] is used to search protein databases for sequences containing regions of homology to the query sequence. The parameter E, which establishes the statistically significant threshold for reporting database sequence matches was set at 0.001 such that only the sequences with E-value higher than the threshold are included in the database sequence matches.

Mature PIP is an oligomeric glycoprotein formed by six identical subunits of 182 amino acids each [Thwin, M.-M. et al (2000) Biochemistry (in press)]. FIG. 6 shows the alignment of the mature PIP monomer with the database sequences whose match satisfies the pre-set E-value of 0.001. The mature PIP protein contains 16 cysteine residues which all of them align perfectly well in the database matched sequences. It has the highest sequence identity (57–61%) to the mature PLI molecules from the sera of Crotalidae snakes, *Agkistrodon blomhoffii siniticus, Crotalus d. terrificus,* and *Trimeresurus flavoviridis* (*Protobothrops flavoviridis*), with sequence identities of 61, 60 and 57%, respectively. PIP also has a significant (57%) homology to the sequences of mature PLIs of a non-venomous snake *Elaphe quadrivirgata,* and also to those of the PLIs from the sera of Australian Elapidaes, *Notechis ater, Notechis scutatus,* and *Oxyuranus scutellatus,* with sequence identities in the vicinity of 56%.

Furthermore, PSI-BLAST searches are carried out on different regions of the mature PIP amino acid sequence to look for the region of highest similarity matches. When compared with the database amino acid sequences, the highest density of identities is located in the central region of PIP. Thus, the most homologous region among the snake PLIs can be precisely identified as the region spanning residues 81–120 on PIP and corresponding region of matched sequences (TABLE 7).

Interestingly, within this region of highest local amino acid sequence similarity, we recognize a proline-rich cluster corresponding to residues 85–100 of PIP and other database sequences in the alignment. Proline has several distinct properties that could be used for recognition, including its unusually shaped pyrrolidine side chain and the conformational constraints that result from its cyclic structure. Protein-protein interaction domains, such as Src homology 3 (SH3) and WW domains, participate in diverse signaling pathways and are important targets in drug design [Cohen G. B. et al. (1995) *Cell* 80, 237; Nguyen J. T. et al. *Science* 282, 2088–2092]. These domains have been reported to specifically recognize unique proline-rich peptide motifs [Xu, W. et al. *Nature* 385, 595]. In PIP, this proline-rich cluster is identified within the region of the highest density of identities, which seems to represent a crucial component of the PLI pharmacophore. Since the proline-rich segment is highly conserved amongst members of the snake serum PLI family, it is a distinguishing feature, and is therefore believed to contribute to the biological activity specifically associated with the snake PLI family. Hence, based on this premise, we have synthesized oligopeptides corresponding to this region of high amino acid sequence homology between PIP and related snake PLI sequences that contain unique proline-rich peptide motifs (FIG. 7), and examined them for PLA$_2$-inhibitory activity.

All the peptides used in our experiments were custom-synthesized at the Biotechnology Processing Centre (BTC), NUS, by conventional solid phase techniques using automated ABI 4338 Peptide Synthesizer, purified by RP-HPLC using Vydac RP-C8 (2.1×150 mm) columns, and the sequences validated by MALDI mass spectrometry (Voyager-DE STR BioSpectrometry Workstation). PLA$_2$-inhibitory activity of the peptides was assayed using the venoms and PLA$_2$ toxins of the Viperid snake *Daboia russelli siamensis* and of the bee (*Apis mellifera*) as enzymes, and [$^3$H]-arachidonate-labelled *E. coli* as substrate [Elsbach, P. and Weiss, J.(1991), *Methods Enzymol.* 197, 24–31].

To compare inhibitory potencies, the dose-response relationships for all the synthetic peptides and the full-length recombinant PIP were determined and shown in FIG. 8. The amino acid sequences and PLA$_2$ inhibitory properties of a family of synthetic peptides derived from the proline-rich domain is shown in TABLE 8, along with the IC$_{50}$ values (concentration of the protein/peptide that inhibits PLA$_2$ activity by 50%) estimated from the dose-response curves from FIG. 8.

A decapeptide P-0029, which corresponds to PIP residues 87–96, is a very potent inhibitor of PLA$_2$ showing 90% inhibition toward the catalytic activity of daboiatoxin at a peptide concentration of 400 μg [4×10$^{-5}$ M], under the experimental conditions used in our $^3$H-labeled *E. coli* assay system. A similar decapeptide P-0009, which is constructed on the basis of a segment taken from PIP residues 85–94, in which leucine 93 is replaced by a lysine and glutamine 94 substituted with a proline, still retains the inhibitory activity under similar experimental conditions, but shows less activity than P-0029. The nonapeptide P-0006, corresponding to PIP residues 91–98, lacks the core tetrapeptide PGLP that is common to the previous two active peptides, P-0029 and P-0009, but contains an extra lysine residue added at position 99 to improve solubility. Although it shows some PLA$_2$-inhibitory activity, the potency is much less than that of the former two peptides, indicating that the tetrapeptide PGLP seems crucially important for the PLA$_2$-inhibitory activity, the removal of which from the sequence may result in the loss of some biological activity. Another peptide P-0008, which corresponds to PIP residues 85–98, with extra lysine residue added in position 99, is a relatively longer peptide with 15-residues. Since the PLA$_2$-inhibitory activity of P-0008 is insignificant, it seems possible that the length of the peptide is critical, probably for conformational reasons. An even more longer peptide P-0036 with 22-residues has been found to be devoid of PLA$_2$-inhibitory activity, while the peptide P-0005, corresponding to PIP residues 101–102, with an additional 113 lysine fails to inhibit PLA$_2$ activity, but instead enhances the enzyme activity to some extent, the reason for which is unknown.

The two synthetic peptides (P-0029 and P-0009) that show strong in vitro PLA$_2$-inhibitory activity are then tested for anti-inflammatory activity in vivo, and is evident that the peptide P-0029 has very potent anti-inflammatory effect on the PLA$_2$-induced mouse footpad oedema, whereas P-0009 is less potent. TABLE 9 shows the anti-inflammatory effects of P-0029 and P-0009 in comparison to those of the full length recombinant PIP and the known anti-inflammatory peptide AIP-2 (also known as anti-flammin-2) from Sigma Chemicals.

Co-injection of P-0029, either with the venom or its enzymatically active PLA$_2$ (Daboiatoxin, DbTx), or with the bee venom PLA$_2$ into the mouse footpad significantly (P<0.01) inhibits the formation of inflammatory oedema over two different dose ranges of 50 and 100 μg, with a higher suppression of the inflammatory response seen at 100 µg dose. In contrast, neither the peptide P-0009 nor the Sigma anti-inflammatory peptide AIP-2, is as potent as P-0029. Comparison of the dose-responses of P-0029 and the recombinant protein PIP at both 50 and 100 µg doses by one-way ANOVA shows that there is no significant difference (P<0.05) between the two forms of inhibitor. At 100 µg dose, both the recombinant protein PIP, and the decapeptide P-0029 that is deduced from its parent protein sequence, cause nearly complete suppression of the inflammatory response, thus providing evidence that the peptide P-0029 retains almost all the anti-inflammatory property of the intact parent PIP molecule.

The potential therapeutic application of the active peptide P-0029 was further examined in male Sprague-Dawley rats (250–320 g) using an in vivo incisional hernia model. The peptide was administered to the site of injury to assess its effectiveness in reducing the formation of intra-peritoneal adhesions, which is a major source of post-operation morbidity and mortality [diZerega G. S. et al (1992) In: *The peritoneum*, New York, Springer; 274–306]. A ventral abdominal defect (15×25 mm) was created in each of the 30 rats, which were divided into four groups. A polypropylene mesh was stitched to the defect in each animal, and prior to closure of the skin, a hyaluronate-based gel (Hylan GF 20), either alone or with an anti-inflammatory peptide, was administered intra-peritoneally. Group I (n=12) contained only the mesh to serve as a control. Group II (n=6) contained exclusively the gel, while Groups III and IV contained the gel spiked with 168 µg each of the anti-inflammatory peptides, P-0029 and AIP-2, respectively. After one week, adhesions between the mesh and the caecum in the abdominal cavity of the sacrificed rats were scored according to the classification method described elsewhere [Rodgers K. E. et al (1992) *J. Invest. Surg*. 215, 285–293].

Figure 10:
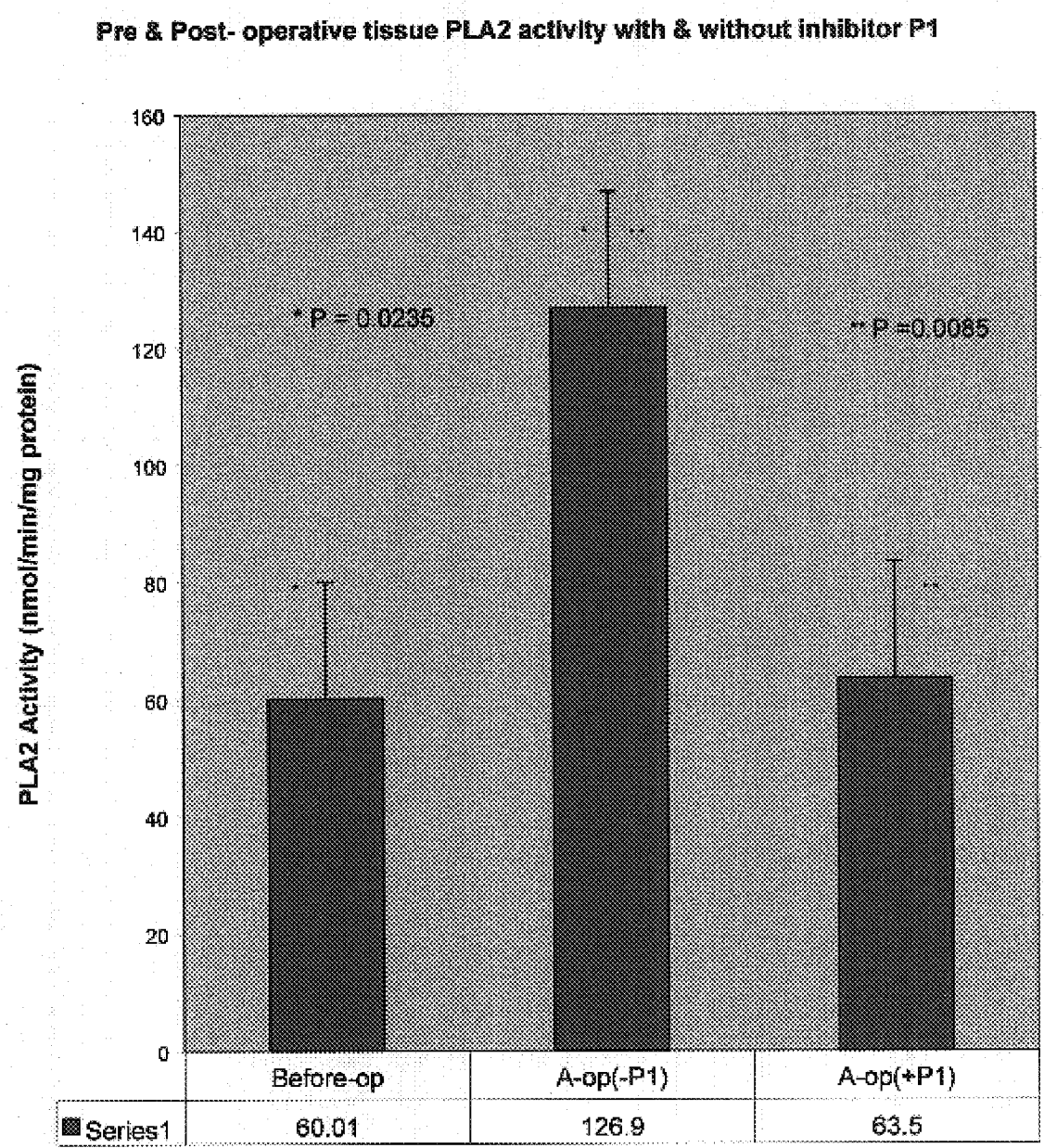

In TABLE 10, the overall adhesion scores for each rats are presented as grades. All the animals (n=12) of the control (Group I) developed maximal degree of adhesions (Grade 4), whereas in the remaining groups (II–IV), adhesion grades varied from as low as 1 to as high as 3 (FIG. 9). This experimental model demonstrates that administration of the active peptide P-0029 along with the gel, significantly reduces (P<0.05) the overall adhesion grade, whereas either the gel alone or the gel with the Sigma Anti-flammin-2 is relatively less potent in reducing the intra-peritoneal adhesion. A parallel decrease in post-operative tissue $PLA_2$ levels of P-0029-treated rats was also observed (FIG. 10). As compared to tissue $PLA_2$ activity of post-operated rats treated with gel alone, those treated with the gel and P-0029 had significantly lower (P<0.05) tissue $PLA_2$ activity after surgery, indicating that the peptide P-0029 is potent enough to effectively reduce the post-operative tissue $PLA_2$ levels, that surges significantly (P<0.05) after surgery, thereby minimizing or preventing the formation of intra-peritoneal adhesions.

The present findings highlight the importance of the core domain PGLP, as a highly conserved sequence present in all the active peptides, and confirm the decapeptide, herein designated P-0029, as a potent anti-inflammatory peptide that has potential therapeutic applications, especially for $PLA_2$-related inflammatory diseases.

Included within the scope of the present invention are those sequences and fragments of the polypeptides as described in SEQ ID NO:10, SEQ ID NO:11, and SEQ ID NO:12, or functional equivalents thereof, which can be used for treating or preventing inflammatory conditions. In yet another aspect, the invention contemplates a method of producing a polypeptide variant of a parent polypeptide comprising the sequences set forth in SEQ ID NO:10, SEQ ID NO:11, and SEQ ID NO:12, or biologically active fragments thereof, comprising the steps of:

(a) replacing at least one amino acid of the parent polypeptide, with a different amino acid to produce a modified polypeptide;

(b) deleting and/or adding the parent polypeptide, modifying the side chains, incorporating unnatural amino acids and/or their derivatives during peptide, polypeptide synthesis and the use of crosslinkers and other methods which impose conformational constraints on the polypeptides, fragments and variants of the invention;

(c) modifying the polypeptides, fragments or variants of the invention using ordinary molecular biological techniques to improve their resistance to proteolytic degradation or to optimize solubility properties or to render them more suitable as an immunogenic agent.

All references patents and patent applications referred to above are incorporated herein by reference.

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appended claims.

TABLE 1

NEUTRALISATION OF *DABOIA RUSSELLI SIAMENSIS* VENOM AND DABOIATOXIN LETHAL ACTIVITY BY VARIOUS ANIMAL SERA.

| | Survival (mice alive/total) | | |
|---|---|---|---|
| Origin of serum | Daboiatoxin ($5LD_{50}$) | *Daboia russelli siamensis* venom ($2LD_{50}$) | ($4LD_{50}$) |
| Venom/daboiatoxin alone + snake serum | 0/4 | 0/4 | 0/4 (11 ± 3) |
| Python *reticulatus* | 3/4 | 4/4 | 1/4 (>24) |
| Naja naja *sputatrix* | 0/4 | 0/4 | 0/4 (12 ± 2) |
| Notechis *scutatus* | n.t | 0/4 | 0/4 (20 ± 2) |
| Pseudechis *australis* | n.t | 1/4 | 0/4 (22 ± 2) |
| Pseudechis *porphyriacus* | n.t | 1/4 | 0/4 (22 ± 1) |
| Pseudonaja *texilis* + animal serum | n.t | 0/4 | 0/4 (18 ± 2) |
| Little civet cat (*Viverricula indica*) | 0/4 | 0/4 | 0/4 (12 ± 3) |
| Peafowl (*Pavo cristatus*) | 0/4 | 0/4 | 0/4 (10 ± 1) |
| Monkey (*Macaca fasicularis*) | 0/4 | 0/4 | 0/4 (11 ± 2) |

Figures in parentheses = mean survival time (± SD) after 4 $LD_{50}$ intraperitoneal venom dose. n.t. = not tested. Mice (n = 4) were injected intraperitoneally with a 0.2 mL mixture containing indicated doses of crude venom or Daboiatoxin (DbTx) in saline previously incubated (1 h, 37° C.) with 40 µL of various serum samples (3–3.5 mg serum protein) or saline only. Survival was recorded after 24 h.

TABLE 2

NEUTRALIZING POTENCY OF PYTHON SERUM AND ITS IMMUNOGLOBULIN-FREE FRACTION

| Treatment | Lethality (Alive/total) | Oedema activity Myotoxicity | (Oedema ratio) (Serum CK level) |
|---|---|---|---|
| *Daboia russelli siamensis* venom | 0/4 (0) | 162 ± 6 (0) | 1224 ± 132 (0) |
| + commercial antivenin | 5/6 (83) | 169 ± 2 (0) | 317 ± 13 (74) |
| + anti-daboiatoxin | 4/6 (66) | 140 ± 3 (14) | 209 ± 7 (83) |
| + Python *reticulatus* serum | 4/6 (66) | 128 ± 5 (21) | 146 ± 12 (88) |
| + ammonium sulphate precipitated fraction (immunoglobulin-free) | 6/6 (100) | 110 ± 9 (32) | 108 ± 6 (91) |
| + normal human serum (control) | 0/4 (0) | 165 ± 10 (0) | 1123 ± 23 (9) |

Figures in parentheses = % neutralisation; values are the mean ± SD (n = 4). Serum samples were preincubated at 37° C. for 1 hr with the venom before injection into mice. 5, 10, and 20 μg venom protein respectively, were used to induce oedema, myonecrosis, and lethality in mice.

TABLE 3

SUMMARY OF PURIFICATION OF PAF FROM PYTHON *RETICULATUS* CRUDE SERUM

| Purification step | Total Protein (mg) | Inhibitory activity* ($IC_{50}$) | Yield (%) | Purification Factor |
|---|---|---|---|---|
| Crude serum (30 mL) | 800 | 8 | 100 | 1.0 |
| 45–80% $(NH_4)_2SO_4$ ppt. | 100 | 5 | 12.50 | 1.6 |
| UNO Q1 anion exchange | 10 | 2.2 | 1.25 | 3.6 |
| Superdex 75 gel filtration | 2 | 0.2 | 0.25 | 40 |
| Sephasil C18 RP-HPLC | 1.4 | — | 0.17 | 80 |

Expressed as IC50 units, the inhibitor concentration (mg) required to inhibit 50% of the original $PLA_2$ activity of 1 $LD_{50}$ dose-equivalent (20 μg) of *Daboia russelli siamensis* venom, under the test conditions. The smaller the number of $IC_{50}$ units, the higher is the $PLA_2$ inhibitory activity.

TABLE 4

NEUTRALISATION ACTIVITY OF NATIVE PAF AND MONOSPECIFIC ANTIVENIN AGAINST LETHALITY OF *DABOIA RUSSELLI* VENOM

| Type of treatment | Protection against lethality Survival/total | % neutralisation |
|---|---|---|
| Antitoxic factor PAF alone | 3/3 | — |
| *Daboia russelli siamensis* venom (Burma) alone | 0/3 | 0 |
| *Daboia r. siamensis* venom (Burma) + antivenin | 5/6 | 83 |
| *Daboia r. siamensis* venom (Burma) + python serum | 4/6 | 66 |
| *Daboia r. siamensis* venom (Burma) + PAF | 4/4 | 100 |
| *Daboia r. siamensis* venom (Thailand) + PAF | 3/3 | 100 |
| *Daboia r. siamensis* venom (Sri Lanka) + PAF | 3/3 | 100 |
| *Daboia r. siamensis* venom (India) ) + PAF | 3/3 | 100 |

2 $LD_{50}$ intraperitoneal dose (40 μg) of *Daboia russelli* venoms from different locality (Burma, Sri Lanka, Thailand, India) were used for lethality and in vivo neutralisation assays in mice, Doses of neutralisation agents used: python serum (3.2 mg), PAF (0.05 mg), antivenin (6 mg). Neutralising agents were preincubated at 37° C. for 30 min with the respective venoms before intraperitoneal injection into Swiss albino mice, and survival was recorded 24 hr post-injection.

TABLE 5

NEUTRALISING EFFECT OF RECOMBINANT PAF ON SNAKE VENOMS AND $PLA_2$ TOXINS

| Venom/$PLA_2$ toxin | Death/survival | % Neutralisation |
|---|---|---|
| Group I | | |
| *Oxyuranus s. scutellatus* venom[1] | 2/2 | 50 |
| *Pseudechis textilis* venom[2] | 1/3 | 75 |
| Taipoxin (*Oxyuranus scutellatus* $PLA_2$)[a] | 2/2 | 50 |
| 3-Bungarotoxin (*Bungarus multicinctus* $PLA_2$)[b] | 0/3 | 100 |
| Group II | | |
| *Agkistrodon halys blomhoffi* venom[3] | 1/3 | 75 |
| *Daboia russelli siamensis* (Myanmar) venom[4] | 0/4 | 100 |
| *Daboia russelli siamensis* (Thailand) venom[5] | 0/4 | 100 |
| *Daboia russelli pulchella* (Sri Lanka) venom[6] | 0/4 | 100 |
| *Daboia russelli russelli* (India) venom[7] | 0/4 | 100 |
| Daboiatoxin (Myanmar *Daboia r. siamensis* $PLA_2$)[c] | 0/4 | 100 |
| VRV-PL-VIII[a] (Sri Lankan *Daboia r. pulchella* $PLA_2$)[d] | 0/4 | 100 |
| VRV-PL-V (Indian *Daboia r. russelli* $PLA_2$)[e] | 0/4 | 100 |
| Ammodytoxin A (*Vipera a. ammodytes* $PLA_2$)[f] | 1/3 | 75 |
| Crotoxin (*Crotalus d. terrificus* $PLA_2$)[g] | 0/3 | 100 |
| Mojave toxin-B (*Crotalus s. scutellatus* $PLA_2$)[h] | 1/3 | 75 |
| Group III | | |
| *Apis melifera* (bee venom) $PLA_2$[i] | 0/3 | 100 |

Swiss albino mice (25 g) were injected intraperitoneally with 200 μL of saline containing predetermined lethal doses (~$2LD_{50}$ i.p doses) of various venoms (20 μg[1]; 25 μg[4]; 40 μg[2, 3, 5–7]) and $PLA_2$ toxins (1 μg[1]; 5 μg[b, f]; 10 μg[a, c, g]; 15 μg[h]; 50 μg[c]; 200 μg[d]) previously incubated with recombinant PAF (100 μg for Group II venoms/toxic$PLA_{2S}$; 150 μg for Group I and III venoms/toxins) for 30 min at 37° C. Survival was recorded after 24 hr.

TABLE 7

PSI-BLAST SEARCH DATA ON DIFFERENT REGIONS OF
PIP FOR HIGHEST IDENTITY MATCHES WITH
DATABASE SEQUENCES

| | Percentage Identities | | | | | |
|---|---|---|---|---|---|---|
| Source of PLI | Full-length [1–182] | Region I [1–40] | Region II [41–80] | Region III [81–120] | Region IV [121–160] | Region V [161–182] |
| Python reticulatus | 100 | 100 | 100 | 100 | 100 | 100 |
| Agkistrodon blomhoffii siniticus | 61 | 55 | 60 | 75 | 60 | 62 |
| Crotalus d. Terrificus | 60 | 60 | 60 | 72 | 61 | 57 |
| Protobothrops flavoviridis | 57 | 52 | 55 | 67 | 57 | 59 |
| Elaphe quadrivirgata | 57 | 61 | 52 | 58 | 62 | 66 |
| Notechis ater α isoform NAI-3A | 57 | 58 | 56 | 62 | 57 | 61 |
| Notechis scutatus α$_{iii}$ isoform | 56 | 53 | 59 | 62 | 57 | 59 |
| Oxyuranus scutellatus α OSI-1A | 56 | 56 | 52 | 62 | 57 | 59 |

Figures in brackets represent amino acid residue positions on the Python inhibitor PIP and corresponding regions of matched sequences. The column showing the highest density of identities is high-lighted.

TABLE 6

EFFECT OF PAF ON PLA$_2$-INDUCED OEDEMA IN MICE

| Treatment | Paw oedema (mg)* | % Inhibition (mean) |
|---|---|---|
| Daboia russelli siamensis venom (5 μg) | 116 ± 16 | — |
| +PAF (25 μg) | 107 ± 20 | 7.8 |
| + PAF (50 μg) | 62 ± 2.2 | 46.5 |
| + PAF (100 μg) | 29 ± 0.8 | 74.6 |
| + AIP-2 (50 μg) | 79 ± 6.1 | 31.9 |
| + Daboia russelli siamensis antivenin (150 μg) | 106 ± 2.5 | n.s. |
| Daboiatoxin PLA$_2$ (1.5 μg) | 167 ± 12 | |
| + PAF (50 μg) | 18 ± 6.0 | 89.4 |
| + PAF (100 μg) | 13 ± 0.4 | 92.1 |
| + Anti-daboiatoxin immune serum (0.8 mg) | 99 ± 5.8 | 14.0 |
| Bee venom (Apis melifera) PLA$_2$ (1 μg) | 87 ± 3.8 | |
| + PAF (50 μg) | 55 ± 0.5 | 36.8 |
| + PAF (100 μg) | 19 ± 0.3 | 78.2 |
| + AIP-2 (50 μg) | 49 ± 0.2 | 43.7 |
| PAF alone (100 μg) | 10 ± 5.2 | n.s. |
| AIP-2 alone (50 μg) | 7.7 ± 3.4 | n.s. |

*mean ± S.D (n = 3). n.s. = not significant. Mice (20–25 g) were injected subplantarly into the left paw with the indicated amounts of venom or PLA$_2$ toxins with or without the inhibitors (PAF = Python Antitoxic Factor; AIP-2 = anti-inflammatory Peptide-2 from Sigma) in a total volume of 25 μL of sterile solution. Hind limbs from animals sacrificed at 45 min post-injection were removed at the ankle joint and weighed individually. The increase in weight (mg) due to oedema was calculated by subtracting the weight of each saline injected right hind limb. Inhibitory effects were assessed by comparing the paw oedema of animals receiving PLA$_2$ + inhibitor to those receiving PLA$_2$ alone.

TABLE 8

AMINO ACID SEQUENCES AND PROPERTIES OF PLA$_2$ -
INHIBITORY SYNTHETIC PEPTIDES

| Code No. | Sequence | Length | Mol. Wt. | PLA$_2$ inhibition* (%) | IC$_{50}$ [μg] | Anti-Inflammatory Activity |
|---|---|---|---|---|---|---|
| PP-0036 (SEQ ID NO:30) | PLPGLPLSLQNGLYCPGAFGIF | 22 | 2275 | −3.0 | — | Negative |
| PP-0008 (SEQ ID NO:31) | PLPGLPLSLQNGLYK | 15 | 1610 | 18 | — | Negative |
| PP-0009 (SEQ ID NO:11) | PLPGLPSKP | 10 | 1018 | 80 | 125 | (+) weak |
| PP-0029 (SEQ ID NO:10) | - - PGLPLSLQNG | 10 | 995 | 90 | 40 | (++) strong |
| PP-0006 (SEQ ID NO:12) | - - - - - - LSLQNGLYK | 9 | 1035 | 70 | 250 | Not tested |
| PP-0005 (SEQ ID NO:32) | - - - - - - - - - GAFGIFTEDSTEK | 13 | 1401 | −13 | — | Negative |

*Maximal enzyme inhibition towards daboiatoxin, the major PLA$_2$ toxin of Daboia russelli siamensis venom seen at a fixed peptide concentration (400 μg). IC$_{50}$ values were estimated from the corresponding dose-response curves. Anti-inflammatory activity was assessed by daboiatoxin-induced mouse paw oedema experiments.

TABLE 9

ANTI-INFLAMMATORY EFFECT OF INHIBITORS ON PLA$_2$-INDUCED PAW OEDEMA

| Treatment | Oedema (mg) | % Inhibition |
|---|---|---|
| DRS venom (5 μg) Control A | 117 ± 20 | — |
| + 25 μg PIP | 107 ± 20 | 11.7 ± 13.6 (P > 0.1)* |
| + 50 μg PIP | 61 ± 2 | 47.6 ± 1.9 (P < 0.01) |
| + 100 μg PIP | 29 ± 1 | 74.7 ± 0.8 (P < 0.01) |
| + 50 μg P-0009 | 92 ± 17 | 21.1 ± 14.8 (P > 0.1)* |
| + 100 μg P-0009 | 82 ± 5 | 29.3 ± 4.6 (P < 0.05) |
| + 50 μg P-0029 | 48 ± 3 | 58.9 ± 2.9 (P < 0.01) |
| + 100 μg P-0029 | 33 ± 6 | 71.1 ± 5.5 (P < 0.01) |
| + 100 μg AIP-2 | 76 ± 11 | 35.0 ± 9.7 (P < 0.05) |
| DbTx (1 μg) Control B | 166 ± 9 | — |
| + 50 μg PIP | 18 ± 5 | 89.2 ± 3.0 (P < 0.01) |
| + 100 μg PIP | 13 ± 3 | 92.2 ± 1.8 (P < 0.01) |
| + 50 μg P-0009 | 124 ± 10 | 25.7 ± 5.9 (P < 0.01) |
| + 100 μg P-0009 | 110 ± 19 | 33.6 ± 11.2 (P < 0.01) |
| + 50 μg P-0029 | 63 ± 7 | 62.1 ± 4.0 (P < 0.01) |
| + 100 μg P-0029 | 35 ± 6 | 79.0 ± 3.6 (P < 0.01) |
| + 100 μg AIP-2 | 108 ± 11 | 35.3 ± 6.5 (P < 0.01) |
| Bee venom PLA$_2$ (1 μg) Control C | 89 ± 6 | — |
| + 50 μg PIP | 52 ± 3 | 39.9 ± 3.8 (P < 0.01) |
| + 100 μg PIP | 19 ± 2 | 78.1 ± 2.1 (P < 0.01) |
| + 50 μg P-0009 | 82 ± 5 | 6.3 ± 5.1 (P > 0.1)* |
| + 100 μg P-0009 | 72 ± 5 | 16.6 ± 5.6 (P < 0.01) |
| + 50 μg P-0029 | 42 ± 4 | 51.7 ± 4.2 (P < 0.01) |
| + 100 μg P-0029 | 31 ± 4 | 63.8 ± 4.8 (P < 0.01) |
| + 100 μg AIP-2 | 60 ± 7 | 33.6 ± 3.9 (P < 0.01) |
| PIP alone (100 μg) | 19 ± 8 | — |
| P-0009 alone (100 μg) | 17 ± 6 | — |
| P-0029 alone (100 μg) | 13 ± 2 | — |
| AIP-2 alone (100 μg) | 9 ± 4 | — |

DRS, *Daboia russelli siamensis;* PIP, phospholipase A$_2$ inhibitor from python; P-, synthetic peptide; AIP-2, anti-inflammatory peptide-2 from Sigma; DbTx, daboiatoxin PLA$_2$. Values are given as mean ± SD (n = 4). Inhibitory effects, expressed as percentage inhibition of paw oedema, were assessed by comparing the paw oedema (increase of wt. in mg) of mice receiving (PLA$_2$ + inhibitor) to those receiving PLA$_2$ alone. The results were analysed by a one-tailed Student's t test for groups of unpaired observations (significance taken at minimum of P < 0.05).
*indicates figures that were not statistically significant from the control values.

TABLE 10

EFFECTS OF ANTI-INFLAMMATORY PEPTIDES ON INTRAPERITONEAL ADHESION FORMATION IN INDIVIDUAL RATS

| Group No. | Rat No. | Grade | Adhesion Score Mean ± SD |
|---|---|---|---|
| I (Control) | (255–266) | 4 | 4.0 ± 0[a] (n = 12) |
| II (with gel only) | 267 | 4 | 3.16 ± 2.82[b] (n = 6) |
|  | 268 | 4 |  |
|  | 271 | 4 |  |
|  | 270 | 3 |  |
|  | 269 | 2 |  |
|  | 272 | 2 |  |
| III (with gel + P-0029) | 275 | 1 | 2.00 ± 0.82[c] (n = 6) |
|  | 276 | 1 |  |
|  | 278 | 2 |  |
|  | 273 | 2 |  |
|  | 274 | 3 |  |
|  | 277 | 3 |  |
| IV (with gel + AIP-2) | 279 | 4 | 3.30 ± 1.07[d] (n = 6) |
|  | 284 | 4 |  |
|  | 281 | 4 |  |
|  | 280 | 3 |  |
|  | 283 | 3 |  |
|  | 282 | 2 |  |

One-tailed Student's t test for groups of unpaired observations was done with significance tested at P < 0.05: a vs b, not significant (P > 0.05); a vs c, significant (P < 0.05); a vs d, not significant (P > 0.05). The effects of P-0029 and AIP-2 were confirmed by one-way ANOVA.

---

What is claimed is:

1. An isolated polypeptide comprising the sequence set forth in SEQ ID NO:6, or a fragment thereof having at least 10 contiguous amino acids including the tetrapeptide proline-glycine-leucine-proline and having activity as a phospholipase $A_2$ inhibitor, or a variant thereof having one or more conservative amino acid substitutions while retaining the tetrapeptide proline-glycine-leucine-proline, said variant having activity as a phospholipase $A_2$ inhibitor, wherein said polypeptide is at least 85% homologous to the polypeptide of SEQ ID NO:6.

2. The polypeptide of claim 1, wherein the polypeptide further comprises a leader peptide comprising the sequence set forth in SEQ ID NO:8.

3. The polypeptide of claim 2, wherein the polypeptide comprises the sequence set forth in SEQ ID NO:2.

4. A polypeptide consisting essentially of the amino acid sequence set forth in SEQ ID NO:10.

5. A polypeptide consisting essentially of the amino acid sequence set forth in SEQ ID NO:11.

6. A method of producing a polypeptide variant of a parent polypeptide comprising the sequence set forth in SEQ ID NO:2 or SEQ ID NO:6, comprising the steps of:
   (a) replacing at least one amino acid of the parent polypeptide, with a different amino acid to produce a modified polypeptide;
   (b) combining the modified polypeptide with a phospholipase $A_2$; and
   (c) detecting the presence of a complex comprising the modified polypeptide and the phospholipase $A_2$, which is indicative of the modified polypeptide being said polypeptide variant.

7. A pharmaceutical composition for use in treating envenomation or for use in treating or preventing inflammatory conditions, comprising the polypeptide or fragment or variant thereof of claim 1, together with a pharmaceutically acceptable carrier.

8. A method for treatment of envenomation, comprising administering to a patient in need of such treatment a therapeutically effective amount of a composition comprising the polypeptide or fragment or variant thereof of claim 1, together with a pharmaceutically acceptable carrier.

9. A method for treatment or prophylaxis of an inflammatory condition, comprising administering to a patient in need of such treatment a therapeutically effective amount of a composition comprising the polypeptide or fragment or variant thereof of claim 1, together with a pharmaceutically acceptable carrier.

10. The method of claim 9, wherein the inflammatory condition is an inflammatory condition instigated by phospholipase $A_2$.

11. The polypeptide of claim 1, having an $IC_{50}$ for inhibition of 400 µg of daboiatoxin of 125 µg or less.

12. The isolated polypeptide fragment of claim 1, having at least 20 contiguous amino acids.

13. The isolated polypeptide fragment of claim 1, having at least 30 contiguous amino acids.

14. The polypeptide of claim 1, comprising the sequence set forth in SEQ ID NO:6.

* * * * *